United States Patent
Tumer et al.

(10) Patent No.: US 8,026,410 B2
(45) Date of Patent: Sep. 27, 2011

(54) TRANSGENIC PLANTS EXPRESSING L3 DELTA PROTEINS ARE RESISTANT TO TRICHOTHECENE FUNGAL TOXINS

(75) Inventors: Nilgun E. Tumer, Belle Mead, NJ (US); Rong Di, East Brunswick, NJ (US)

(73) Assignee: Rutger, The State University, New Brunswick, NJ (US)

( * ) Notice: Subject to any disclaimer, the term of this patent is extended or adjusted under 35 U.S.C. 154(b) by 0 days.

(21) Appl. No.: 12/384,050

(22) Filed: Mar. 30, 2009

(65) Prior Publication Data

US 2010/0146667 A1   Jun. 10, 2010

Related U.S. Application Data

(63) Continuation of application No. 11/010,795, filed on Dec. 13, 2004, now abandoned.

(60) Provisional application No. 60/529,348, filed on Dec. 12, 2003.

(51) Int. Cl.
C12N 15/09 (2006.01)
C12N 15/82 (2006.01)
A01H 5/00 (2006.01)
A01H 5/10 (2006.01)

(52) U.S. Cl. ........ 800/279; 800/278; 800/298; 800/295; 800/320.1; 800/320.2; 800/320.3; 800/317; 435/468; 435/419

(58) Field of Classification Search ....................... None
See application file for complete search history.

(56) References Cited

U.S. PATENT DOCUMENTS 6,060,646 A   5/2000   Harris et al.

FOREIGN PATENT DOCUMENTS

WO   00/39291   7/2000

OTHER PUBLICATIONS

Khachatourians, Canad. J. Physiol. Pharm. 68:1004-1008 (1990).
Miller et al., Nat. Toxins 5:234-237 (1997).
Hampl et al., J. Biol. Chem. 256:2284-2288 (1981).
Noller, J. Bacteriol. 175:5297-5300 (1993).
Green et al., Annu. Rev. Biochem. 66:679-716 (1997).
Fried et al., Proc. Natl. Acad. Sci. USA 78:238-242 (1981).
Muhitch et al., Plant Science 157:201-207 (2000).
Harris et al., Physiol. Mol. Plant Path. 58:173-181 (2001).
Peltz, et al., Molecular and Cell Biology 19(1):384-391 (1999).

*Primary Examiner* — Medina A Ibrahim
(74) *Attorney, Agent, or Firm* — Lerner, David, Littenberg, Krumholz & Mentlik, LLP

(57) ABSTRACT

Disclosed are specific mutants of L3 and transgenic plants that produce them. The plants exhibit increased resistance to fungal toxins that target ribosomal L3 protein. Also disclosed are transgenic plants that co-produce L3 mutant and an RIP protein, and exhibit increased resistance to various fungal toxins and viruses, while reducing toxicity normally associated with production of the RIP. Uses of the L3 mutants in animals are further disclosed.

23 Claims, 45 Drawing Sheets

FIG. 9A
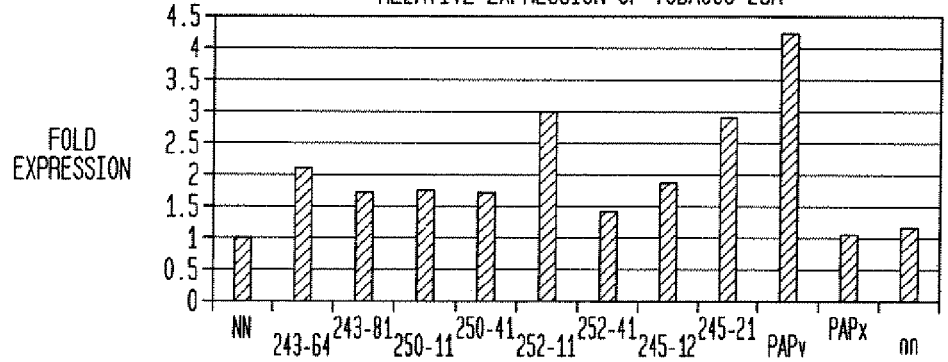
FIG. 9B
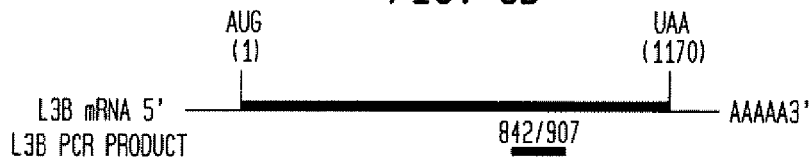
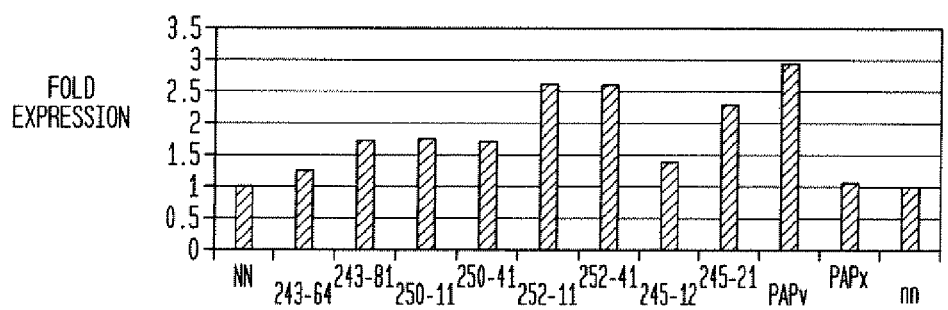
FIG. 9C
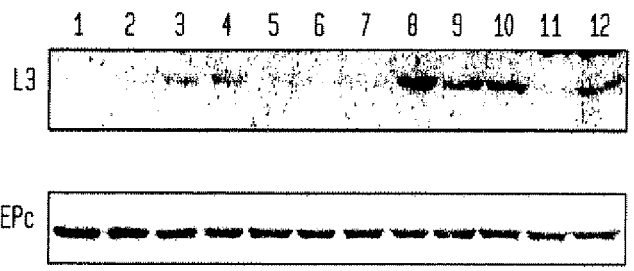

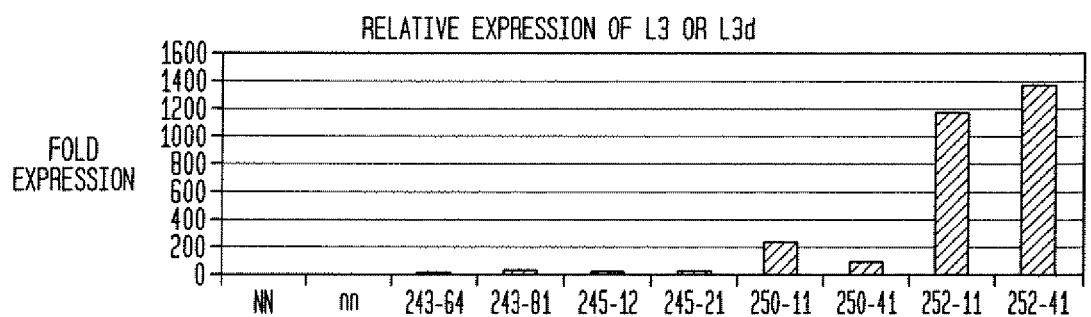
FIG. 10A
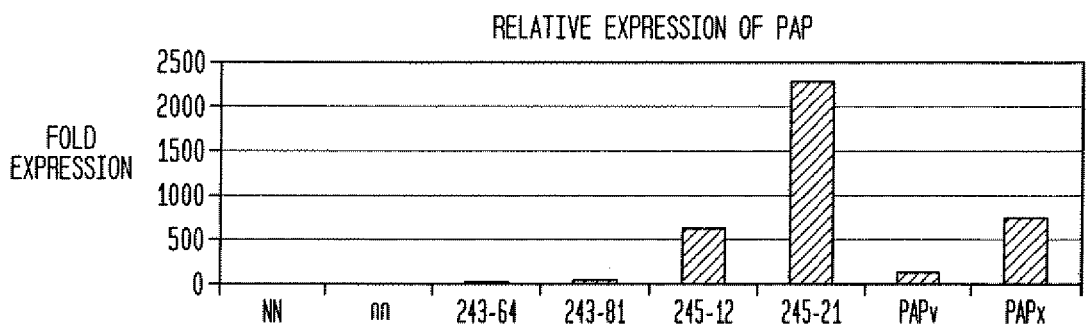
FIG. 10B
FIG. 10C
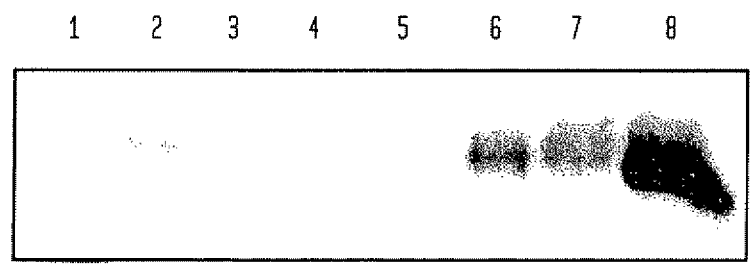

FIG. 11B

```
              1          11         21         31         41         51         61
              +----+----+----+----+----+----+----+----+----+----+----+----+
AtRPL3A       MSHRKFEHPRHGSLGFLPRKRANRHPGKVRAFPKDDQTKPCKFTAFHGYKHGHIVRDLVL
AthRPL3B      MSHRKFEHPRHGSLGFLPRKRHNSRHHGKVRAFPKDDPTKPCRLTSFLGYKHGHIVRIVE
NtRPL3-8d     MSIRKFEHPRHGSLGFLPRKRHARHPGKVKAFPKDDPNKFCKLTAFLGYKHGHTHLVRIVE
NtRPL3-10d    MSIRKFEHPRHGSLGFLPRKRHASIRARVKAFPKDDTTKPCRLTAFLGYKHGHTBTVRSVE
YRPL3         MSIRKYEHPRHGHLGFLPRKRHASIRARVKAFPKDIRSKPVALTSFLGYKHGMTIVRDLIA
HvRPL3        NYIKGRREKMSHRKKEHPRTGSLGFLPRKRHPGKCKSFPKDHKTKPVHLTAFLGYKHGHIVRDLI
fivRPL3       ----------MSHRKZEhPRhGgsLGFLPRKRq.rhhgkvkafPKDd.tKPv.lTaFlGYKhGHIVR.1.
Consensus 71         81         91         100
              +----+----+----+----+----+----+
AtRPL3A       KPGSKLHKKETCERVITIETPAHVVVGVVAYVKTFRGLR
AthRPL3B      KPGSKLHKKETCEAVITIETPPHVVVGVVGYVKTFRGLR
NtRPL3-8d     KPGSKLIKKETCELVTTIETPPHIVVGVVGYVKTFRGLE
NtRPL3-10d    RPGSKFHKREVVEAVIVVDTPVVVGVVGYVETPRGLR
YRPL3         RPGSKMHKKEVVEAVITEIPPIVVGVVGYVETPRGLR
HvRPL3        rpgsk.hkkevveqviiiettp.vvvGvVgYVetfPRGLR
fivRPL3
Consensus
```

FIG. 12

The nucleotide sequence and corresponding amino acid sequence of the yeast wild-type L3 protein (known as rpl3) are set forth below.

```
ATGTCTCACAGAAAGTACGAAGCACCACGTCACGGTCATTTAGGTTTCTTGCCA
AGAAAG
 1 ---------+---------+---------+---------+---------+---------+ 60
TACAGAGTGTCTTTCATGCTTCGTGGTGCAGTGCCAGTAAATCCAAAGAACGGT
TCTTTC
``` a    M  S  H  R  K  Y  E  A  P  R  H  G  H  L  G  F  L  P  R  K -

```
AGAGCTGCCTCCATCAGAGCTAGAGTTAAGGCTTTTCCAAAGGATGACAGATCC
AAGCCA
 61 ---------+---------+---------+---------+---------+---------+ 120
TCTCGACGGAGGTAGTCTCGATCTCAATTCCGAAAAGGTTTCCTACTGTCTAGG
TTCGGT
``` a    R  A  A  S  I  R  A  R  V  K  A  F  P  K  D  D  R  S  K  P -

```
GTTGCTCTAACTTCCTTCTTGGGTTACAAGGCTGGTATGACCACCATTGTCAGAG
ATTTG
121 ---------+---------+---------+---------+---------+---------+ 180
CAACGAGATTGAAGGAAGAACCCAATGTTCCGACCATACTGGTGGTAACAGTC
TCTAAAC
``` a    V  A  L  T  S  F  L  G  Y  K  A  G  M  T  T  I  V  R  D  L -

```
GACAGACCAGGTTCTAAGTTCCACAAGCGTGAAGTTGTCGAAGCTGTCACCGTT
GTTGAC
181 ---------+---------+---------+---------+---------+---------+ 240
CTGTCTGGTCCAAGATTCAAGGTGTTCGCACTTCAACAGCTTCGACAGTGGCAA
CAACTG
``` a    D  R  P  G  S  K  F  H  K  R  E  V  V  E  A  V  T  V  V  D -

```
ACTCCACCAGTTGTCGTTGTTGGTGTTGTCGGTTACGTCGAAACCCCAAGAGGT
TTGAGA
241 ---------+---------+---------+---------+---------+---------+ 300
TGAGGTGGTCAACAGCAACAACCACAACAGCCAATGCAGCTTTGGGGTTCTCC
AAACTCT
``` a    T  P  P  V  V  V  V  G  V  V  G  Y  V  E  T  P  R  G  L  R -

FIG. 12 (CONT'D)

```
      TCTTTGACCACCGTCTGGGCTGAACATTTGTCTGACGAAGTCAAGAGAAGATTC
      TACAAG
         301 ----+----+----+----+----+----+ 360
      AGAAACTGGTGGCAGACCCGACTTGTAAACAGACTGCTTCAGTTCTCTTCTAAG
      ATGTTC a    S  L  T  T  V  W  A  E  H  L  S  D  E  V  K  R  R  F  Y  K  -

AACTGGTACAAGTCTAAGAAGAAGGCTTTCACCAAATACTCTGCCAAGTACGCT
      CAAGAT
         361 ----+----+----+----+----+----+ 420
      TTGACCATGTTCAGATTCTTCTTCCGAAAGTGGTTTATGAGACGGTTCATGCGA
      GTTCTA a    N  W  Y  K  S  K  K  K  A  F  T  K  Y  S  A  K  Y  A  Q  D  -

GGTGCTGGTATTGAAAGAGAATTGGCTAGAATCAAGAAGTACGCTTCCGTCGTC
      AGAGTT
         421 ----+----+----+----+----+----+ 480
      CCACGACCATAACTTTCTCTTAACCGATCTTAGTTCTTCATGCGAAGGCAGCAG
      TCTCAA a    G  A  G  I  E  R  E  L  A  R  I  K  K  Y  A  S  V  V  R  V  -

TTGGTCCACACTCAAATCAGAAAGACTCCATTGGCTCAAAAGAAGGCTCATTTG
      GCTGAA
         481 ----+----+----+----+----+----+ 540
      AACCAGGTGTGAGTTTAGTCTTTCTGAGGTAACCGAGTTTTCTTCCGAGTAAAC
      CGACTT a    L  V  H  T  Q  I  R  K  T  P  L  A  Q  K  K  A  H  L  A  E  -

ATCCAATTGAACGGTGGTTCCATCTCTGAAAAGGTTGACTGGGCTCGTGAACAT
      TTCGAA
         541 ----+----+----+----+----+----+ 600
      TAGGTTAACTTGCCACCAAGGTAGAGACTTTTCCAACTGACCCGAGCACTTGTA
      AAGCTT
```

```
AAGACTGTTGCTGTCGACAGCGTTTTTGAACAAAACGAAATGATTGACGCTATT
GCTGTC
   601 ---------+---------+---------+---------+---------+---------+ 660
TTCTGACAACGACAGCTGTCGCAAAAACTTGTTTTGCTTTACTAACTGCGATAA
CGACAG
``` a    K T V A V D S V F E Q N E M I D A I A V -

```
ACCAAGGGTCACGGTTTCGAAGGTGTTACCCACAGATGGGGTACTAAGAAATT
GCCAAGA
   661 ---------+---------+---------+---------+---------+---------+ 720
TGGTTCCCAGTGCCAAAGCTTCCACAATGGGTGTCTACCCCATGATTCTTTAAC
GGTTCT
``` a    T K G H G F E G V T H R W G T K K L P R -

```
AAGACTCACAGAGGTCTAAGAAAGGTTGCTTGTATTGGTGCTTGGCATCCAGCC
CACGTT
   721 ---------+---------+---------+---------+---------+---------+ 780
TTCTGAGTGTCTCCAGATTCTTTCCAACGAACATAACCACGAACGGTAGGTCGG
GTGCAA
``` a    K T H R G L R K V A C I G A W H P A H V -

```
ATGTGGAGTGTTGCCAGAGCTGGTCAAAGAGGTTACCATTCCAGAACCTCCATT
AACCAC
   781 ---------+---------+---------+---------+---------+---------+ 840
TACACCTCACAACGGTCTCGACCAGTTTCTCCAATGGTAAGGTCTTGGAGGTAA
TTGGTG
``` a    M W S V A R A G Q R G Y H S R T S I N H -

```
AAGATTTACAGAGTCGGTAAGGGTGATGATGAAGCTAACGGTGCTACCAGCTT
CGACAGA
   841 ---------+---------+---------+---------+---------+---------+ 900
TTCTAAATGTCTCAGCCATTCCCACTACTACTTCGATTGCCACGATGGTCGAAGC
TGTCT
```

```
ACCAAGAAGACTATTACCCCAATGGGTGGTTTCGTCCACTACGGTGAAATTAAG
AACGAC
 901 ---------+---------+---------+---------+---------+---------+ 960
TGGTTCTTCTGATAATGGGGTTACCCACCAAAGCAGGTGATGCCACTTTAATTC
TTGCTG
``` a    T K K T I T P M G G F V H Y G E I K N D -

```
TTCATCATGGTTAAAGGTTGTATCCCAGGTAACAGAAAGAGAATTGTTACTTTG
AGAAAG
 961 ---------+---------+---------+---------+---------+---------+ 1020
AAGTAGTACCAATTTCCAACATAGGGTCCATTGTCTTTCTCTTAACAATGAAAC
TCTTTC
``` a    F I M V K G C I P G N R K R I V T L R K -

```
TCTTTGTACACCAACACTTCTAGAAAGGCTTTGGAAGAAGTCAGCTTGAAGTGG
ATTGAC
 1021 ---------+---------+---------+---------+---------+---------+ 1080
AGAAACATGTGGTTGTGAAGATCTTTCCGAAACCTTCTTCAGTCGAACTTCACC
TAACTG
``` a    S L Y T N T S R K A L E E V S L K W I D -

```
ACTGCTTCTAAGTTCGGTAAGGGTAGATTCCAAACCCCAGCTGAAAAGCATGCT
TTCATG
 1081 ---------+---------+---------+---------+---------+---------+ 1140
TGACGAAGATTCAAGCCATTCCCATCTAAGGTTTGGGGTCGACTTTTCGTACGA
AAGTAC
``` a    T A S K F G K G R F Q T P A E K H A F M -

```
GGTACTTTGAAGAAGGACTTGTAA
 1141 ---------+---------+---- 1164
CCATGAAACTTCTTCCTGAACATT
``` a    G T L K K D L * -

FIG. 13

L3 nucleic acids cloned from Arabidopsis and rice are described in Kim, et al., Gene 93:177-182 (1990), and Nishi, et al., Biochim. Biophys. Acta 1216:110-112 (1993) respectively. Tobacco contains two L3 genes. The nucleotide sequence and corresponding amino acid sequence for one tobacco L3 protein (the tobacco "8d" L3 protein) are set forth below:

```
ATGTCTCACAGGAAGTTTGAGCATCCAAGACACGGTTCTTTGGGATTTCTGCCC
AGGAAG
    1 ---------+---------+---------+---------+---------+---------+ 60
TACAGAGTGTCCTTCAAACTCGTAGGTTCTGTGCCAAGAAACCCTAAAGACGGG
TCCTTC a    M  S  H  R  K  F  E  H  P  R  H  G  S  L  G  F  L  P  R  K -

CGTGCTGCCAGACACAGGGGAAAGGTGAAGGCATTCCCAAAAGATGATCCAAA
CAAGCCC
   61 ---------+---------+---------+---------+---------+---------+ 120
GCACGACGGTCTGTGTCCCCTTTCCACTTCCGTAAGGGTTTTCTACTAGGTTTGT
TCGGG a    R  A  A  R  H  R  G  K  V  K  A  F  P  K  D  D  P  N  K  P -

TGCAAGCTAACTGCCTTCTTGGGCTACAAAGCTGGCATGACTCACATTGTCAGA
GATGTT
  121 ---------+---------+---------+---------+---------+---------+ 180
ACGTTCGATTGACGGAAGAACCCGATGTTTCGACCGTACTGAGTGTAACAGTCT
CTACAA a    C  K  L  T  A  F  L  G  Y  K  A  G  M  T  H  I  V  R  D  V -

GAAAAACCTGGATCAAAACTCCACAAGAAAGAGACATGTGAAGCTGTCACCAT
CATTGAA
  181 ---------+---------+---------+---------+---------+---------+ 240
CTTTTTGGACCTAGTTTTGAGGTGTTCTTTCTCTGTACACTTCGACAGTGGTAGT
AACTT a    E  K  P  G  S  K  L  H  K  K  E  T  C  E  A  V  T  I  I  E -
```

FIG. 13 (CONT'D)

```
ACACCTCCAATGGTGATTGTTGGTGTTGTTGGGTATGTGAAGACACCTCGTGGT
CTTCGT
    241 ---------+---------+---------+---------+---------+---------+ 300

TGTGGAGGTTACCACTAACAACCACAACAACCCATACACTTCTGTGGAGCACCA
GAAGCA a    T  P  P  M  V  I  V  G  V  V  G  Y  V  K  T  P  R  G  L  R -

TGCCTGAACACTGTCTGGGCTCAACATCTCAGTGAAGAGCTTAAGAGGAGGTTC
TACAAG
    301 ---------+---------+---------+---------+---------+---------+ 360

ACGGACTTGTGACAGACCCGAGTTGTAGAGTCACTTCTCGAATTCTCCTCCAAG
ATGTTC a    C  L  N  T  V  W  A  Q  H  L  S  E  E  L  K  R  R  F  Y  K -

AACTGGTGCAAGTCCAAGAAGAAGGCCTTCTTGAAATACTCCAAGAAATATGA
ATCTGAT
    361 ---------+---------+---------+---------+---------+---------+ 420

TTGACCACGTTCAGGTTCTTCTTCCGGAAGAACTTTATGAGGTTCTTTATACTTA
GACTA a    N  W  C  K  S  K  K  K  A  F  L  K  Y  S  K  K  Y  E  S  D -

GAAGGGAAAAAGGACATCCAGACACAGCTGGAGAAATTGAAGAAGTATGCAT
GCGTCATC
    421 ---------+---------+---------+---------+---------+---------+ 480

CTTCCCTTTTTCCTGTAGGTCTGTGTCGACCTCTTTAACTTCTTCATACGTACGCA
GTAG a    E  G  K  K  D  I  Q  T  Q  L  E  K  L  K  K  Y  A  C  V  I -

CGTGTTTTGGCTCACACTCAGATAAGGAAGATGAAGGGTCTGAAACAGAAGAA
AGCCCAT
    481 ---------+---------+---------+---------+---------+---------+ 540

GCACAAAACCGAGTGTGAGTCTATTCCTTCTACTTCCCAGACTTTGTCTTCTTTC
GGGTA a    R  V  L  A  H  T  Q  I  R  K  M  K  G  L  K  Q  K  K  A  H -
```

FIG. 13 (CONT'D)

```
TTGATGGAGATACAGGTGAATGGAGGGACAATTGCTCAGAAGGTTGACTTTGC
ATATGGT
   541 ---------+---------+---------+---------+---------+---------+ 600
AACTACCTCTATGTCCACTTACCTCCCTGTTAACGAGTCTTCCAACTGAAACGTA
TACCA a    L M E I Q V N G G T I A Q K V D F A Y G -

TTCTTCGAGAAGCAGGTTCCAGTTGATGCTGTTTTTCAGAAGGATGAGATGATT
GACATC
   601 ---------+---------+---------+---------+---------+---------+ 660
AAGAAGCTCTTCGTCCAAGGTCAACTACGACAAAAAGTCTTCCTACTCTACTAA
CTGTAG a    F F E K Q V P V D A V F Q K D E M I D I-

ATTGGTGTCACCAAGGGTAAGGGTTATGAAGGTGTTGTAACTCGTTGGGGTGTG
ACACGT
   661 ---------+---------+---------+---------+---------+---------+ 720
TAACCACAGTGGTTCCCATTCCCAATACTTCCACAACATTGAGCAACCCCACAC
TGTGCA a    I G V T K G K G Y E G V V T R W G V T R -

CTTCCTCGCAAAACCCACAGGGGTCTGCGTAAGGTTGCTTGTATTGGAGCCTGG
CACCCT
   721 ---------+---------+---------+---------+---------+---------+ 780
GAAGGAGCGTTTTGGGTGTCCCCAGACGCATTCCAACGAACATAACCTCGGACC
GTGGGA a    L P R K T H R G L R K V A C I G A W H P -

GCTAGAGTTTCCTACACAGTTGCCCGTGCTGGTCAAAATGGATACCATCACCGT
ACCGAG
   781 ---------+---------+---------+---------+---------+---------+ 840
CGATCTCAAAGGATGTGTCAACGGGCACGACCAGTTTTACCTATGGTAGTGGCA
TGGCTC
```

```
ATGAACAAGAAGGTTTACAAACTAGGGAAGGCTGGCCAAGAGTCCCATGCTGC
TGTAACT
   841 ---------+---------+---------+---------+---------+---------+ 900
TACTTGTTCTTCCAAATGTTTGATCCCTTCCGACCGGTTCTCAGGGTACGACGAC
ATTGA
``` a    M N K K V Y K L G K A G Q E S H A A V T -

```
GATTTTGACAGGACCGAGAAGACATTACTCCCATGGGTGGATTTCCCCATTAT
GGTGTG
   901 ---------+---------+---------+---------+---------+---------+ 960
CTAAAACTGTCCTGGCTCTTTCTGTAATGAGGGTACCCACCTAAAGGGGTAATA
CCACAC
``` a    D F D R T E K D I T P M G G F P H Y G V -

```
GTGAAGGATGATTACCTGTTGATCAAGGGATGCTGTGTTGGTCCTAAGAAGAGG
GTTGTA
   961 ---------+---------+---------+---------+---------+---------+ 1020
CACTTCCTACTAATGGACAACTAGTTCCCTACGACACAACCAGGATTCTTCTCC
CAACAT
``` a    V K D D Y L L I K G C C V G P K K R V V -

```
ACCCTTCGTCAGTCCCTGCTCAACCAGACCTCTCGTGTCGCTCTTGAGGAGATTA
AGCTG
  1021 ---------+---------+---------+---------+---------+---------+ 1080
TGGGAAGCAGTCAGGGACGAGTTGGTCTGGAGAGCACAGCGAGAACTCCTCTA
ATTCGAC
``` a    T L R Q S L L N Q T S R V A L E E I K L -

```
AAGTTCATCGATACATCCTCAAAGTTTGGACATGGTCGCTTCCAGACCACTCAA
GAGAAG
  1081 ---------+---------+---------+---------+---------+---------+ 1140
TTCAAGTAGCTATGTAGGAGTTTCAAACCTGTACCAGCGAAGGTCTGGTGAGTT
CTCTTC
```

```
       CAGAAATTCTATGGCCGGTTGAAGGGTTAA
1141 ----+----+----+----+ 1170
       GTCTTTAAGATACCGGCCAACTTCCCAATT
``` a    Q K F Y G R L K G * -

The nucleotide sequence and corresponding amino acid sequence for the second tobacco L3 protein (the tobacco "10d" L3 protein) are set forth below.

```
ATGTCGCATCGCAAGTTTGAGCACCCAAGACACGGTTCTTTGGGATTTCTTCCA
AGGAAA
   1 ----+----+----+----+----+----+ 60
TACAGCGTAGCGTTCAAACTCGTGGGTTCTGTGCCAAGAAACCCTAAAGAAGGT
TCCTTT
``` a    M S H R K F E H P R H G S L G F L P R K -

```
AGAGCAGCACGACACAGGGGCAAAGTGAAGGCTTTTCCCAAAGATGATACAAC
AAAACCT
  61 ----+----+----+----+----+----+ 120
TCTCGTCGTGCTGTGTCCCCGTTTCACTTCCGAAAAGGGTTTCTACTATGTTGTT
TTGGA
``` a    R A A R H R G K V K A F P K D D T T K P -

```
TGCAGGTTGACAGCTTTCCTTGGCTACAAAGCTGGTATGACTCATATTGTCAGA
GATGTT
 121 ----+----+----+----+----+----+ 180
ACGTCCAACTGTCGAAAGGAACCGATGTTTCGACCATACTGAGTATAACAGTCT
CTACAA
``` a    C R L T A F L G Y K A G M T H I V R D V -

```
GAAAAACCAGGGTCAAAACTCCATAAGAAAGAAACATGCGAACTGGTTACCAT
AATTGAA
 181 ----+----+----+----+----+----+ 240
CTTTTTGGTCCCAGTTTTGAGGTATTCTTTCTTTGTACGCTTGACCAATGGTATTA
ACTT
```

```
ACGCCTCCTATGATTGTTGTTGGGGTTGTTGGCTATGTGAAAACACCACGTGGC
CTTCGC
    241 ---------+---------+---------+---------+---------+---------+ 300
TGCGGAGGATACTAACAACAACCCCAACAACCGATACACTTTTGTGGTGCACCG
GAAGCG
``` a    T P P M I V V G V V G Y V K T P R G L R -

```
TGCCTTAGCACGGTCTGGGCTCAACATCTTAGTGAAGAGATTAAAAGGAGATTC
TACAAG
    301 ---------+---------+---------+---------+---------+---------+ 360
ACGGAATCGTGCCAGACCCGAGTTGTAGAATCACTTCTCTAATTTTCCTCTAAG
ATGTTC
``` a    C L S T V W A Q H L S E E I K R R F Y K -

```
AACTGGTGCATGTCCAAAAAGAAGGCCTTTGCAAAGTACTCGAAGAAGTATGA
AACTGAT
    361 ---------+---------+---------+---------+---------+---------+ 420
TTGACCACGTACAGGTTTTTCTTCCGGAAACGTTTCATGAGCTTCTTCATACTTT
GACTA
``` a    N W C M S K K K A F A K Y S K K Y E T D -

```
GATGGTAAGAAGGATATTAATGCGCAATTGGAGAAGATGAAGAAGTATTGTTG
TGTCATT
    421 ---------+---------+---------+---------+---------+---------+ 480
CTACCATTCTTCCTATAATTACGCGTTAACCTCTTCTACTTCTTCATAACAACAC
AGTAA
``` a    D G K K D I N A Q L E K M K K Y C C V I -

```
CGTGTTTTGGCCCATACTCAGATTAGAAAAATGAAAGGTCTCAAGCAAAAGAA
GGCACAT
    481 ---------+---------+---------+---------+---------+---------+ 540
GCACAAAACCGGGTATGAGTCTAATCTTTTTACTTTCCAGAGTTCGTTTTCTTCC
GTGTA
```

```
CTGATGGAGATTCAGGTTAATGGTGGGGATGTTTCCCAGAAGGTTGATTATGCT
TATGGC
   541 ------+---------+---------+---------+---------+---------+ 600

GACTACCTCTAAGTCCAATTACCACCCCTACAAAGGGTCTTCCAACTAATACGA
ATACCG
``` a     L M E I Q V N G G D V S Q K V D Y A Y G -

```
TTCTTTGAGAAGCAGATTCCTGTTGATGCTATTTTCCAAAAGGATGAGATGATC
GATATT
   601 ------+---------+---------+---------+---------+---------+ 660

AAGAAACTCTTCGTCTAAGGACAACTACGATAAAAGGTTTTCCTACTCTACTAG
CTATAA
``` a     F F E K Q I P V D A I F Q K D E M I D I -

```
ATTGGTGTGACCAAAGGTAAGGGTTATGAGGGTGTGGTGACTCGTTGGGGTGTA
ACCCGT
   661 ------+---------+---------+---------+---------+---------+ 720

TAACCACACTGGTTTCCATTCCCAATACTCCCACACCACTGAGCAACCCCACAT
TGGGCA
``` a     I G V T K G K G Y E G V V T R W G V T R -

```
CTCCCACGTAAGACCCATCGTGGTCTTAGAAAGGTGGCTTGTATTGGTGCTTGG
CATCCA
   721 ------+---------+---------+---------+---------+---------+ 780

GAGGGTGCATTCTGGGTAGCACCAGAATCTTTCCACCGAACATAACCACGAACC
GTAGGT
``` a     L P R K T H R G L R K V A C I G A W H P -

```
GCACGGGTGTCATACACTGTAGCTAGGGCTGGGCAGAATGGTTATCACCATCGC
ACTGAG
   781 ------+---------+---------+---------+---------+---------+ 840
```

FIG. 13 (CONT'D)

```
CGTGCCCACAGTATGTGACATCGATCCCGACCCGTCTTACCAATAGTGGTAGCG
TGACTC
``` a   A R V S Y T V A R A G Q N G Y H H R T E -

```
CTGAACAAGAAAGTCTACAGGCTGGGCAAGGCTGGTCAGGAGTCTCATTCTGC
AATAACT
   841 ---------+---------+---------+---------+---------+---------+ 900
```

```
GACTTGTTCTTTCAGATGTCCGACCCGTTCCGACCAGTCCTCAGAGTAAGACGT
TATTGA
``` a   L N K K V Y R L G K A G Q E S H S A I T -

```
GAGTTTGACAGGACTGAGAAGGATATCACGCCAATGGGTGGATTTCCTCATTAT
GGTATT
   901 ---------+---------+---------+---------+---------+---------+ 960
```

```
CTCAAACTGTCCTGACTCTTCCTATAGTGCGGTTACCCACCTAAAGGAGTAATA
CCATAA
``` a   E F D R T E K D I T P M G G F P H Y G I -

```
GTGAAAGAAGACTTTCTGTTGATTAAGGGCTGCTGTGTTGGACCAAAGAAGCGT
GTTGTG
   961 ---------+---------+---------+---------+---------+---------+ 1020
```

```
CACTTTCTTCTGAAAGACAACTAATTCCCGACGACACAACCTGGTTTCTTCGCA
CAACAC
``` a   V K E D F L L I K G C C V G P K K R V V -

```
ACTCTGAGGCAGTCTCTGTTGAATCAGACATCTAGGGTTGCATTGGAGGAGATC
AAGCTC
  1021 ---------+---------+---------+---------+---------+---------+ 1080
```

```
TGAGACTCCGTCAGAGACAACTTAGTCTGTAGATCCCAACGTAACCTCCTCTAG
TTCGAG
``` a   T L R Q S L L N Q T S R V A L E E I K L -

```
AAGTTCATTGACACATCCTCCAAGTTTGGCCATGGACGCTTCCAGACTACACAG
GAGAAG
```

FIG. 14

The nucleotide sequence and corresponding amino acid sequence for a spontaneously occurring mutant L3 gene obtained from the yeast *Saccharomyces cerevisiae* (the L3 trichodermin resistance mutant (tcm1)) are set forth below. One nucleotide change G765C results in the amino acid change W255C (Trp255Cys). See, Schultz, et al., J. Bacteriol. *155*:8-14 (1983).

```
ATGTCTCACAGAAAGTACGAAGCACCACGTCACGGTCATTTAGGTTTCTTGCCA
AGAAAG
  1 ---------+---------+---------+---------+---------+---------+ 60
TACAGAGTGTCTTTCATGCTTCGTGGTGCAGTGCCAGTAAATCCAAAGAACGGT
TCTTTC a   M S H R K Y E A P R H G H L G F L P R K -

AGAGCTGCCTCCATCAGAGCTAGAGTTAAGGCTTTTCCAAAGGATGACAGATCC
AAGCCA
 61 ---------+---------+---------+---------+---------+---------+ 120
TCTCGACGGAGGTAGTCTCGATCTCAATTCCGAAAAGGTTTCCTACTGTCTAGG
TTCGGT a   R A A S I R A R V K A F P K D D R S K P -

GTTGCTCTAACTTCCTTCTTGGGTTACAAGGCTGGTATGACCACCATTGTCAGAG
ATTTG
121 ---------+---------+---------+---------+---------+---------+ 180
CAACGAGATTGAAGGAAGAACCCAATGTTCCGACCATACTGGTGGTAACAGTC
TCTAAAC a   V A L T S F L G Y K A G M T T I V R D L -
```

FIG. 14 (CONT'D)

```
GACAGACCAGGTTCTAAGTTCCACAAGCGTGAAGTTGTCGAAGCTGTCACCGTT
GTTGAC
   181 ---------+---------+---------+---------+---------+---------+ 240

CTGTCTGGTCCAAGATTCAAGGTGTTCGCACTTCAACAGCTTCGACAGTGGCAA
CAACTG a    D  R  P  G  S  K  F  H  K  R  E  V  V  E  A  V  T  V  V  D  -

ACTCCACCAGTTGTCGTTGTTGGTGTTGTCGGTTACGTCGAAACCCCAAGAGGT
TTGAGA
   241 ---------+---------+---------+---------+---------+---------+ 300

TGAGGTGGTCAACAGCAACAACCACAACAGCCAATGCAGCTTTGGGGTTCTCC
AAACTCT a    T  P  P  V  V  V  G  V  V  G  Y  V  E  T  P  R  G  L  R  -

TCTTTGACCACCGTCTGGGCTGAACATTTGTCTGACGAAGTCAAGAGAAGATTC
TACAAG
   301 ---------+---------+---------+---------+---------+---------+ 360

AGAAACTGGTGGCAGACCCGACTTGTAAACAGACTGCTTCAGTTCTCTTCTAAG
ATGTTC a    S  L  T  T  V  W  A  E  H  L  S  D  E  V  K  R  R  F  Y  K  -

AACTGGTACAAGTCTAAGAAGAAGGCTTTCACCAAATACTCTGCCAAGTACGCT
CAAGAT
   361 ---------+---------+---------+---------+---------+---------+ 420

TTGACCATGTTCAGATTCTTCTTCCGAAAGTGGTTTATGAGACGGTTCATGCGA
GTTCTA a    N  W  Y  K  S  K  K  K  A  F  T  K  Y  S  A  K  Y  A  Q  D  -

GGTGCTGGTATTGAAAGAGAATTGGCTAGAATCAAGAAGTACGCTTCCGTCGTC
AGAGTT
   421 ---------+---------+---------+---------+---------+---------+ 480

CCACGACCATAACTTTCTCTTAACCGATCTTAGTTCTTCATGCGAAGGCAGCAG
TCTCAA
```

```
TTGGTCCACACTCAAATCAGAAGACTCCATTGGCTCAAAAGAAGGCTCATTTG
GCTGAA
   481 ---------+---------+---------+---------+---------+---------+ 540

AACCAGGTGTGAGTTTAGTCTTTCTGAGGTAACCGAGTTTTCTTCCGAGTAAAC
CGACTT
``` a   L V H T Q I R K T P L A Q K K A H L A E -

```
ATCCAATTGAACGGTGGTTCCATCTCTGAAAAGGTTGACTGGGCTCGTGAACAT
TTCGAA
   541 ---------+---------+---------+---------+---------+---------+ 600

TAGGTTAACTTGCCACCAAGGTAGAGACTTTTCCAACTGACCCGAGCACTTGTA
AAGCTT
``` a   I Q L N G G S I S E K V D W A R E H F E -

```
AAGACTGTTGCTGTCGACAGCGTTTTTGAACAAAACGAAATGATTGACGCTATT
GCTGTC
   601 ---------+---------+---------+---------+---------+---------+ 660

TTCTGACAACGACAGCTGTCGCAAAAACTTGTTTTGCTTTACTAACTGCGATAA
CGACAG
``` a   K T V A V D S V F E Q N E M I D A I A V -

```
ACCAAGGGTCACGGTTTCGAAGGTGTTACCCACAGATGGGGTACTAAGAAATT
GCCAAGA
   661 ---------+---------+---------+---------+---------+---------+ 720

TGGTTCCCAGTGCCAAAGCTTCCACAATGGGTGTCTACCCCATGATTCTTTAAC
GGTTCT
``` a   T K G H G F E G V T H R W G T K K L P R -

```
AAGACTCACAGAGGTCTAAGAAAGGTTGCTTGTATTGGTGCTTGCCATCCAGCC
CACGTT
   721 ---------+---------+---------+---------+---------+---------+ 780

TTCTGAGTGTCTCCAGATTCTTTCCAACGAACATAACCACGAACGGTAGGTCGG
GTGCAA
```

```
ATGTGGAGTGTTGCCAGAGCTGGTCAAAGAGGTTACCATTCCAGAACCTCCATT
AACCAC
    781 ---------+---------+---------+---------+---------+---------+ 840
```

```
TACACCTCACAACGGTCTCGACCAGTTTCTCCAATGGTAAGGTCTTGGAGGTAA
TTGGTG
``` a     M W S V A R A G Q R G Y H S R T S I N H -

```
AAGATTTACAGAGTCGGTAAGGGTGATGATGAAGCTAACGGTGCTACCAGCTT
CGACAGA
    841 ---------+---------+---------+---------+---------+---------+ 900
```

```
TTCTAAATGTCTCAGCCATTCCCACTACTACTTCGATTGCCACGATGGTCGAAGC
TGTCT
``` a     K I Y R V G K G D D E A N G A T S F D R -

```
ACCAAGAAGACTATTACCCCAATGGGTGGTTTCGTCCACTACGGTGAAATTAAG
AACGAC
    901 ---------+---------+---------+---------+---------+---------+ 960
```

```
TGGTTCTTCTGATAATGGGGTTACCCACCAAAGCAGGTGATGCCACTTTAATTC
TTGCTG
``` a     T K K T I T P M G G F V H Y G E I K N D -

```
TTCATCATGGTTAAAGGTTGTATCCCAGGTAACAGAAAGAGAATTGTTACTTTG
AGAAAG
    961 ---------+---------+---------+---------+---------+---------+ 1020
```

```
AAGTAGTACCAATTTCCAACATAGGGTCCATTGTCTTTCTCTTAACAATGAAAC
TCTTTC
``` a     F I M V K G C I P G N R K R I V T L R K -

```
TCTTTGTACACCAACACTTCTAGAAAGGCTTTGGAAGAAGTCAGCTTGAAGTGG
ATTGAC
   1021 ---------+---------+---------+---------+---------+---------+ 1080
```

FIG. 14 (CONT'D)

```
AGAAACATGTGGTTGTGAAGATCTTTCCGAAACCTTCTTCAGTCGAACTTCACC
TAACTG a   S L Y T N T S R K A L E E V S L K W I D ·

ACTGCTTCTAAGTTCGGTAAGGGTAGATTCCAAACCCCAGCTGAAAAGCATGCT
TTCATG
1081 ---------+---------+---------+---------+---------+---------+ 1140

TGACGAAGATTCAAGCCATTCCCATCTAAGGTTTGGGGTCGACTTTTCGTACGA
AAGTAC a   T A S K F G K G R F Q T P A E K H A F M ·

GGTACTTTGAAGAAGGACTTGTAA
1141 ---------+---------+--- 1164
    CCATGAAACTTCTTCCTGAACATT a   G T L K K D L
```

FIG. 15

PAP

5'CTATGAAGTCGGGTCAAAGCATATACAGGCTATGCATTGTTAGAAACATTGATGCCTCTGATCC
CGATAAACAATACAAATTAGACAATAAGATGACATACAAGTACCTAAACTGTGTATGGGGGAGT
GAAACCTCAGCTGCTAAAAAAACGTTGTAAGAAAAAAAGAAAGTTGTGAGTTAACTACAGGGCG
AAAGTATTGGAACT

AGCTAGTAGGAAGGGAAG ATG AAG TCG ATG CTT GTG GTG ACA ATA TCA ATA
         Met Lys Ser Met Leu Val Val Thr Ile Ser Ile
                (67)
TGG CTC ATT CTT GCA CCA ACT TCA ACT TGG GCT GTG AAT ACA ATC ATC TAC
Trp Leu Ile Leu Ala Pro Thr Ser Thr Trp Ala Val Asn Thr Ile Ile Tyr
             (1)
   (100)
AAT GTT GGA AGT ACC ACC ATT AGC AAA TAC GCC ACT TTT CTG AAT GAT CTT
Asn Val Gly Ser Thr Thr Ile Ser Lys Tyr Ala Thr Phe Leu Asn Asp Leu
    (10)         (20)
CGT AAT GAA GCG AAA GAT CCA AGT TTA AAA TGC TAT GGA ATA CCA ATG CTG
Arg Asn Glu Ala Lys Asp Pro Ser Leu Lys Cys Tyr Gly Ile Pro Met Leu
     (30)         (40)

CCC AAT ACA AAT ACA AAT CCA AAG TAC GTG TTG GTT GAG CTC CAA GGT TCA
Pro Asn Thr Asn Thr Asn Pro Lys Tyr Val Leu Val Glu Leu Gln Gly Ser
         (50)
AAT AAA AAA ACC ATC ACA CTA ATG CTG AGA CGA AAC AAT TTG TAT GTG ATG
Asn Lys Lys Thr Ile Thr Leu Met Leu Arg Arg Asn Asn Leu Tyr Val Met
   (60)         (70)
GGT TAT TCT GAT CCC TTT GAA ACC AAT AAA TGT CGT TAC CAT ATC TTT AAT
Gly Tyr Ser Asp Pro Phe Glu Thr Asn Lys Cys Arg Tyr His Ile Phe Asn
     (80)         (90)
GAT ATC TCA GGT ACT GAA CGC CAA GAT GTA GAG ACT ACT CTT TGC CCA AAT
Asp Ile Ser Gly Thr Glu Arg Gln Asp Val Glu Thr Thr Leu Cys Pro Asn
        (100)
GCC AAT TCT CGT GTT AGT AAA AAC ATA AAC TTT GAT AGT CGA TAT CCA ACA
Ala Asn Ser Arg Val Ser Lys Asn Ile Asn Phe Asp Ser Arg Tyr Pro Thr
   (110)         (120)
TTG GAA TCA AAA GCG GGA GTA AAA TCA AGA AGT CAG GTC CAA CTG GGA ATT
Leu Glu Ser Lys Ala Gly Val Lys Ser Arg Ser Gln Val Gln Leu Gly Ile
    (130)        (140)
CAA ATA CTC GAC AGT AAT ATT GGA AAG ATT TCT GGA GTG ATG TCA TTC ACT
Gln Ile Leu Asp Ser Asn Ile Gly Lys Ile Ser Gly Val Met Ser Phe Thr
     (150)
GAG AAA ACC GAA GCC GAA TTC CTA TTG GTA GCC ATA CAA ATG GTA TCA GAG
Glu Lys Thr Glu Ala Glu Phe Leu Leu Val Ala Ile Gln Met Val Ser Glu
(160)          (170)
GCA GCA AGA TTC AAG TAC ATA GAG AAT CAG GTG AAA ACT AAT TTT AAC AGA
Ala Ala Arg Phe Lys Tyr Ile Glu Asn Gln Val Lys Thr Asn Phe Asn Arg
   (180)         (190)
GCA TTC AAC CCT AAT CCC AAA GTA CTT AAT TTG CAA GAG ACA TGG GGT AAG
Ala Phe Asn Pro Asn Pro Lys Val Leu Asn Leu Gln Glu Thr Trp Gly Lys
     (200)        (210)
ATT TCA ACA GCA ATT CAT GAT GCC AAG AAT GGA GTT TTA CCC AAA CCT CTC
Ile Ser Thr Ala Ile His Asp Ala Lys Asn Gly Val Leu Pro Lys Pro Leu
        (220)

FIG. 15 (CONT'D)

```
GAG CTA GTG GAT GCC AGT GGT GCC AAG TGG ATA GTG TTG AGA GTG GAT GAA
Glu Leu Val Asp Ala Ser Gly Ala Lys Trp Ile Val Leu Arg Val Asp Glu
       (230)                                   (240)
ATC AAG CCT GAT GTA GCA CTC TTA AAC TAC GTT GGT GGG AGC TGT CAG ACA
Ile Lys Pro Asp Val Ala Leu Leu Asn Tyr Val Gly Gly Ser Cys Gln Thr
            (250)                                    (260)
ACT TAT AAC CAA AAT GCC ATG TTT CCT CAA CTT ATA ATG TCT ACT TAT TAT
Thr Tyr Asn Gln Asn Ala Met Phe Pro Gln Leu Ile Met Ser Thr Tyr Tyr
(262)                          (270)
AAT TAC ATG GTT AAT CTT GGT GAT CTA TTT GAA GGA TTC TGATCATAAACA
Asn Tyr Met Val Asn Leu Gly Asp Leu Phe Glu Gly Phe
     (280)                                (290)
TAATAAGGAGTATATATATATTACTCCAACTATATTATAAAGCTTAAATAAGAGGCCGTGTTAATT
AGTACTTGTTGCCTTTTGCTTTATGGTGTTGTTTATTATGCCTTGTATGCTTGTAATATTATCTAGA
GAACAAGATGTACTGTGTAATAGTCTTGTTTGAAATAAAACTTCCAATTATGATGCAAAAAAAAA
AAAAAA3
```

FIG. 16
PAPII

```
     ATGAAGATGAAGGTGTTAGAAGTAGTTGGGTTGGCAATATCGAT ATGGCTGATGCTTACA
 55  ----+---------+---------+---------+---------+---------+---- 114
     TACTTCTACTTCCACAATCTTCATCAACCCAACCGTTATAGCTATACCGACTACGAATGT

M  K  M  K  V  L  E  V  V  G  L  A  I  S  I  W  L  M  L  T   -

CCACCAGCTTCTTCAAACATAGTGTTTGAC GTTGAGAATGCCACACCAGAAACCTACTCT
115  ----+---------+---------+---------+---------+---------+---- 174
     GGTGGTCGAAGAAGTTTGTATCACAAACTGCAACTCTTACGGTGTGGTCTTTGGATGAGA

P  P  A  S  S  N  I  V  F  D  V  E  N  A  T  P  E  T  Y  S   -

AATTTTCTGACTA GTTTGCCAGAAGCTGTGAAAGACAAGAAATTGACATGCCATGGAATG
175  ----+---------+---------+---------+---------+---------+---- 234
     TTAAAAGACTGATCAAACGCTCTTCGACACTTTCTGTTCTTTAACTGTACGGTACCTTAC

N  F  L  T  S  L  R  E  A  V  K  D  K  K  L  T  C  H  G  M   -

ATAATGGCCACAACCCTCACTGAACAACCCAAGTATGTGTTGGTTGACCTCAAATTCGGA
235  ----+---------+---------+---------+---------+---------+---- 294
     TATTACCGGTGTTGGGAGTGACTTGTTGGGTTCATACACAACCAACTGGAGTTTAAGCCT

I  M  A  T  T  L  T  E  Q  P  K  Y  V  L  V  D  L  K  F  G   -

TCTGGAACATTCACATTAGCAATCAGAAGGGGAAACTTATATTTGGAGGGCTATTCTGAC
295  ----+---------+---------+---------+---------+---------+---- 354
     AGACCTTGTAAGTGTAATCGTTAGTCTTCCCCTTTGAATATAAACCTCCCGATAAGACTG

S  G  T  F  T  L  A  I  R  R  G  N  L  Y  L  E  G  Y  S  D   -

ATTTACAATGGAAAATGTCGTTATCGGATCTTCAAGGATTCAGAATCCGATGCCCAAGAG
355  ----+---------+---------+---------+---------+---------+---- 414
     TAAATGTTACCTTTTACAGCAATAGCCTAGAAGTTCCTAAGTCTTAGGCTACGGGTTCTC

I  Y  N  G  K  C  R  Y  R  I  F  K  D  S  E  S  D  A  Q  E   -

ACCGTTTGCCCCGGGGACAAAAGCAAGCCTGGCACTCAGAATAATATCCCCTATGAAAAG
415  ----+---------+---------+---------+---------+---------+---- 474
     TGGCAAACGGGGCCCCTGTTTTCGTTCGGACCGTGAGTCTTATTATAGGGGATACTTTTC

T  V  C  P  G  D  K  S  K  P  G  T  Q  N  N  I  P  Y  E  K   -

AGTTACAAAGGGATGGAATCAAAGGGTGGGCTAGAACTAAATTAGGGTTAGGAAAGATA
475  ----+---------+---------+---------+---------+---------+---- 534
     TCAATGTTTCCCTACCTTAGTTTCCCACCCCGATCTTGATTTAAT CCCAATCCTTTCTAT

S  Y  K  G  M  E  S  K  G  G  A  R  T  K  L  G  L  G  K  I   -

ACACTCAAGAGTCGAATGGGTAAAATCTACGGCAAGGATGCAACGGATCAGAAGCAGTAT
535  ----+---------+---------+---------+---------+---------+---- 594
     TGTGAGTTCTCAGCTTACCCATTTTAGATGCCGTTCCTACGTTGCCTAGTCTTCGTCATA

```
         CAAAAAAATGAGGCTGAATTTCTTCTTATAGCCGTTCAAATGGTTACTGAGGCATCAAGG
595      ------+---------+---------+---------+---------+---------+----654
         GTTTTTTTACTCCGACTTAAAGAAGAATATCGGCAAGTTTACCAATGACTCCGTAGTTCC

Q  K  N  E  A  E  F  L  L  I  A  V  Q  M  V  T  E  A  S  R    -

TTCAAATACATTGAGAACAAAGTGAAGGCTAAATTTGATGATGCCAATGGGTATCAGCCA
655      ------+---------+---------+---------+---------+---------+----714
         AAGTTTATGTAACTCTTGTTTCACTTCCGATTTAAACTACTACGGTTACCCATAGTCGGT

F  K  Y  I  E  N  K  V  K  A  K  P  D  D  A  N  G  Y  Q  P    -

GATCCTAAAGCTATTTCCCTAGAGAAAAATTGGGACAGTGTTTCTAAGGTCATTGCAAAA
715      ------+---------+---------+---------+---------+---------+----774
         CTAGGATTTCGATAAAGGGATCTCTTTTTAACCCTGTCACAAAGATTCCAGTAACGTTTT

D  P  K  A  I  S  L  E  K  N  W  D  S  V  S  K  V  I  A  K    -

GTTGGCACCTCCGGTGATAGTACTGTTACTTTACCTGGAGACCTAAAAGATGAGAATAAT
775      ------+---------+---------+---------+---------+---------+----834
         CAACCGTGGAGGCCACTATCATGACAATGAAATGGACCTCTGGATTTTCTACTCTTATTA

V  G  T  S  G  D  S  T  V  T  L  P  G  D  L  K  D  E  N  N    -

AAACCTTGGACTACGGCCACCATGAACGACCTTAAGAACGACATTATGGCACTCCTAACC
835      ------+---------+---------+---------+---------+---------+----894
         TTTGGAACCTGATGCCGGTGGTACTTGCTGGAATTCTTGCTGTAATACCGTGAGGATTGG

K  P  W  T  T  A  T  M  N  D  L  K  N  D  I  M  A  L  L  T    -

CACGTTACTTGCAAGGTTAAAAGTTCCATGTTCCCTGAAATTATGTCCTATTATTAT AGG
895      ------+---------+---------+---------+---------+---------+----954
         GTGCAATGAACGTTCCAATTTTCAAGGTACAAGGGACTTTAATACAGGATAATAATATCC

H  V  T  C  K  V  K  S  S  M  F  P  E  I  M  S  Y  Y  Y  R    -

ACTAGTATTAGTAACCTTGGTGAATTCGAGTGAT
955      ------+---------+---------+-------- 988
         TGATCATAATCATTGGAACCACTTAAGCTCACTA

```
NT777 seq                                                                    1/1
        1         11        21        31        41        51        61
    1 ATGATATTCCCCAAACAATACCCAATTATAAACTTTACCACAGCGGGTGCCACTGTGCAAAGCTACACAA
  1(+1) M  I  F  P  K  Q  Y  P  I  I  N  F  T  T  A  G  A  T  V  Q  S  Y  T 71 ACTTTATCAGAGCTGTTCGCGGTCGTTTAACAACTGGAGCTGATGTGAGACATGAAATACCAGTGTTGCC
 24(+1) N  F  I  R  A  V  R  G  R  L  T  T  G  A  D  V  R  H  E  I  P  V  L  P 141 AAACAGAGTTGGTTTGCCTATAAACCAACGGTTTATTTTAGTTGAACTCTCAAATCATGCAGAGCTTTCT
 48(+1) N  R  V  G  L  P  I  N  Q  R  F  I  L  V  E  L  S  N  H  A  E  L  S 211 GTTACATTAGCGCTGGATGTCACCAATGCATATGTGGTAGGCTACCGTGCTGGAAATAGCGCATATTTCT
 71(+1) V  T  L  A  L  D  V  T  N  A  Y  V  V  G  Y  R  A  G  N  S  A  Y  F 281 TTCATCCTGACAATCAGGAAGATGCAGAAGCAATCACTCATCTTTTCACTGATGTTCAAAATCGATATAC
 94(+1) F  H  P  D  N  Q  E  D  A  E  A  I  T  H  L  F  T  D  V  Q  N  R  Y  T 351 ATTCGCCTTTGGTGGTAATTATGATAGACTTGAACAACTTGCTGGTAATCTGAGAGAAAATATCGAGTTG
116(+1)  F  A  F  G  G  N  Y  D  R  L  E  Q  L  A  G  N  L  R  E  N  I  E  L 421 GGAAATGGTCCACTAGAGGAGGCTATCTCAGCGCTTTATTATTACAGTACTGGTGGCACTCAGCTTCCAA
141(+1) G  N  G  P  L  E  E  A  I  S  A  L  Y  Y  Y  S  T  G  G  T  Q  L  P 491 CTCTGGCTCGTTCCTTTATAATTTGCATCCAAATGATTTCAGAAGCAGCAAGATTCCAATATATTGAGGG
164(+1) T  L  A  R  S  F  I  I  C  I  Q  M  I  S  E  A  A  R  F  Q  Y  I  E  G 561 AGAAATGCGCACGAGAATTAGGTACAACCGGAGATCTGCACCAGATCCTAGCGTAATTACACTTGAGAAT
188(+1)  E  M  R  T  R  I  R  Y  N  R  R  S  A  P  D  P  S  V  I  T  L  E  N 631 AGTTGGGGGAGACTTTCCACTGCAATTCAAGAGTCTAACCAAGGAGCCTTTGCTAGTCCAATTCAACTGC
211(+1) S  W  G  R  L  S  T  A  I  Q  E  S  N  Q  G  A  F  A  S  P  I  Q  L 701 AAAGACGTAATGGTTCCAAATTCAGTGTGTACGATGTGAGTATATTAATCCCTATCATAGCTCTCATGGT
234(+1) Q  R  R  N  G  S  K  F  S  V  Y  D  V  S  I  L  I  P  I  I  A  L  M  V 771 GTATAGATGCGCACCTCCACCATCGTCACAGTTTTAA
258(+1) Y  R  C  A  P  P  P  S  S  Q  F  *
```

FIG. 18

```
NT782 stx2 seq                                                        1/1
            1         11        21        31        41        51        61
       1 ATGAAGTGTATATTATTTAAATGGGTACTGTGCCTGTTACTGGGTTTTTCTTCGGTATCCTATTCCCGGG
   1(+1)  M  K  C  I  L  F  K  W  V  L  C  L  L  L  G  F  S  S  Y  S  Y  S  R 71 AGTTTACGATAGACTTTTCGACCCAACAAAGTTATGTCTCTTCGTTAAATAGTATACGGACAGAGATATC
  24(+1)  E  F  T  I  D  F  S  T  Q  Q  S  Y  V  S  S  L  N  S  I  R  T  E  I  S 141 GACCCCTCTTGAACATATATCTCAGGGGACCACATCGGTGTCTGTTATTAACCACACCCCACCGGGCAGT
  48(+1)  T  P  L  E  H  I  S  Q  G  T  T  S  V  S  V  I  N  H  T  P  P  G  S 211 TATTTTGCTGTGGATATACGAGGGCTTGATGTCTATCAGGCGCGTTTTGACCATCTTCGTCTGATTATTG
  71(+1)  Y  F  A  V  D  I  R  G  L  D  V  Y  Q  A  R  F  D  H  L  R  L  I  I 281 AGCAAAATAATTTATATGTGGCCGGGTTCGTTAATACGGCAACAAATACTTTCTACCGTTTTTCAGATTT
  94(+1)  E  Q  N  N  L  Y  V  A  G  F  V  N  T  A  T  N  T  F  Y  R  F  S  D  F 351 TACACATATATCAGTGCCCGGTGTGACAACGGTTTCCATGACAACGGACAGCAGTTATACCACTCTGCAA
 118(+1)  T  H  I  S  V  P  G  V  T  T  V  S  M  T  T  D  S  S  Y  T  T  L  Q 421 CGTGTCGCAGCGCTGGAACGTTCCGGAATGCAAATCAGTCGTCACTCACTGGTTTCATCATATCTGGCGT
 141(+1)  R  V  A  A  L  E  R  S  G  M  Q  I  S  R  H  S  L  V  S  S  Y  L  A 491 TAATGGAGTTCAGTGGTAATACAATGACCAGAGATGCATCCAGAGCAGTTCTGCGTTTTGTCACTGTCAC
 164(+1)  L  M  E  F  S  G  N  T  M  T  R  D  A  S  R  A  V  L  R  F  V  T  V  T 561 AGCAGAAGCCTTACGCTTCAGGCAGATACAGAGAGAATTTCGTCAGGCACTGTCTGAAACTGCTCCTGTG
 188(+1)  A  E  A  L  R  F  R  Q  I  Q  R  E  F  R  Q  A  L  S  E  T  A  P  V 631 TATACGATGACGCCGGGAGACGTGGACCTCACTCTGAACTGGGGGCGAATCAGCAATGTGCTTCCGGAGT
 211(+1)  Y  T  M  T  P  G  D  V  D  L  T  L  N  W  G  R  I  S  N  V  L  P  E 701 ATCGGGGAGAGGATGGTGTCAGAGTGGGGAGAATATCCTTTAATAATATATCAGCGATACTGGGGACTGT
 234(+1)  Y  R  G  E  D  G  V  R  V  G  R  I  S  F  N  N  I  S  A  I  L  G  T  V 771 GGCCGTTATACTGAATTGCCATCATCAGGGGGCGCGTTCTGTTCGCGCCGTGAATGAAGAGAGTCAACCA
 258(+1)  A  V  I  L  N  C  H  H  Q  G  A  R  S  V  R  A  V  N  E  E  S  Q  P 841 GAATGTCAGATAACTGGCGACAGGCCTGTTATAAAAATAAACAATACATTATGGGAAAGTAATACAGCTG
 281(+1)  E  C  Q  I  T  G  D  R  P  V  I  K  I  N  N  T  L  W  E  S  N  T  A 911 CAGCCGTTTCTGAACAGAAAGTCACAGTTTTTTATATACAACGGGTAAATAA
 304(+1)  A  A  F  L  N  R  K  S  Q  F  L  Y  T  T  G  K  *
```

FIG. 19

```
NT819 stx1 seq                                                         1/1
            1          11         21         31         41         51         61
       1  ATGAAAATAATTATTTTTAGAGTGCTAACTTTTTTCTTTGTTATCTTTTCAGTTAATGTGGTTGCGAAGG
  1(+1)    M  K  I  I  I  F  R  V  L  T  F  F  F  V  I  F  S  V  N  V  V  A  K 71  AATTTACCTTAGACTTCTCGACTGCAAAGACGTATGTAGATTCGCTGAATCTCATTCGCTCTGCAATAGG
 24(+1)    E  F  T  L  D  F  S  T  A  K  T  Y  V  D  S  L  N  V  I  R  S  A  I  G 141  TACTCCATTACAGACTATTTCATCAGGAGGTACGTCTTTACTGATGATTGATAGTGGCACAGGGGATAAT
 48(+1)    T  P  L  Q  T  I  S  S  G  G  T  S  L  L  M  I  D  S  G  T  G  D  N 211  TTGTTTGCAGTTGATGTCAGAGGGATAGATCCAGAGGAAGGGCGGTTTAATAATCTACGGCTTATTGTTG
 71(+1)    L  F  A  V  D  V  R  G  I  D  P  E  E  G  R  F  N  N  L  R  L  I  V 281  AACGAAATAATTTATATCTGACAGGATTTGTTAACAGGACAAATAATGTTTTTTATCGCTTTGCTGATTT
 94(+1)    E  R  N  N  L  Y  V  T  G  F  V  N  R  T  N  N  V  F  Y  R  F  A  D  F 351  TTCACATGTTACCTTTCCAGGTACAACAGCGGTTACATTGTCTGGTGACAGTAGCTATACCACGTTACAG
118(+1)    S  H  V  T  F  P  G  T  T  A  V  T  L  S  G  D  S  S  Y  T  T  L  Q 421  CGTGTTGCAGGGATCAGTCGTACGGGGATGCAGATAAATCGCCATTCGTTGACTACTTCTTATCTGGATT
141(+1)    R  V  A  G  I  S  R  T  G  M  Q  I  N  R  H  S  L  T  T  S  Y  L  D 491  TAATGTCGCATAGTGGAACCTCACTGACGCAGTCTGTGGCAAGAGCGATGTTACGGTTTGTTACTGTGAC
164(+1)    L  M  S  H  S  G  T  S  L  T  Q  S  V  A  R  A  M  L  R  F  V  T  V  T 561  AGCTGAAGCTTTACGTTTTCGGCAAATACAGAGGGGATTTCGTACAACACTGGATGATCTCAGTGGGCGT
188(+1)    A  E  A  L  R  F  R  Q  I  Q  R  G  F  R  T  T  L  D  D  L  S  G  R 631  TCTTATGTAATGACTGCTGAAGATGTTGATCTTACATTGAACTGGGGAAGGTTGAGTAGTGTCCTGCCTG
211(+1)    S  Y  V  M  T  A  E  D  V  D  L  T  L  N  W  G  R  L  S  S  V  L  P 701  ATTATCATGGACAAGACTCTGTTCGTGTAGGAAGAATTTCTTTTGGAAGCATTAATGCAATTCTGGGAAG
234(+1)    D  Y  H  G  Q  D  S  V  R  V  G  R  I  S  F  G  S  I  N  A  I  L  G  S 771  CGTGGCATTAATACTGAATTGTCATCATCATGCATCGCGAGTTGCCAGAATGGCATCTGATGAGTTTCCT
258(+1)    V  A  L  I  L  N  C  H  H  H  A  S  R  V  A  R  M  A  S  D  E  F  P 841  TCTATGTGTCCGGCAGATGGAAGAGTCCGTGGGATTACGCACAATAAAATATTGTGGGATTCATCCACTC
281(+1)    S  M  C  P  A  D  G  R  V  R  G  I  T  H  N  K  I  L  W  D  S  S  T 911  TGGGGGCAATTCTGATGCGCAGAACTATTAGCAGTTGA
304(+1)    L  G  A  I  L  M  R  R  T  I  S  S  *
```

TOXICITY OF NT760/NT188 AND NT771/NT188 YEAST CELLS UNDER THE INDUCTION OF GALACTOSE

IMMUNOBLOT ANALYSIS OF NT760/NT188 AND NT771/NT188 YEAST CELL EXTRACTS

DEPURINATION ASSAY OF NT760/NT188 YEAST CELLS BY DUAL PRIMER EXTENSION

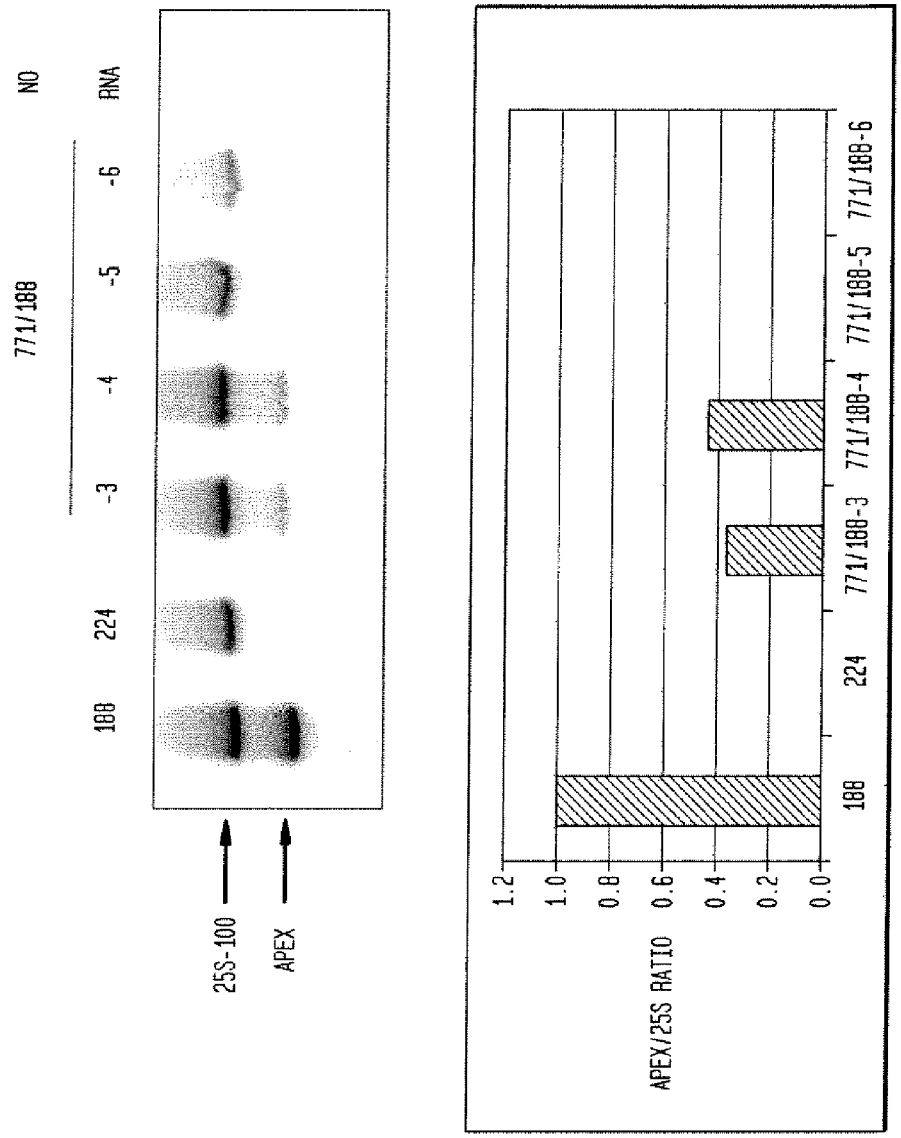
FIG. 22B DEPURINATION ASSAY OF NT771/NT188 YEAST CELLS BY DUAL PRIMER EXTENSION IN VITRO DEPURINATION ASSAY FOR PAP PROTEINS ISOLATED FROM YEAST CONTAINING NT771/NT188 BY DUAL PRIMER EXTENSION REAL-TIME PCR ANALYSIS OF PAP GENE LEVEL IN NT771/NT188 YEAST CELLS AFTER GALACTOSE INDUCTION

STEM LOOP STRUCTURE AT THE 5' END OF L3 plt22gif by D. Stewart and M. Zuker
© 2004 Washington University dG= -8.41 [initially -11.9]  , 66bp.

TOXICITY OF NT803 (L3A21)/NT188 (PAP) YEAST CELLS UNDER THE INDUCTION OF GALACTOSE

TRANSGENIC PLANTS EXPRESSING L3 DELTA PROTEINS ARE RESISTANT TO TRICHOTHECENE FUNGAL TOXINS

CROSS-REFERENCE TO RELATED APPLICATIONS

This application is a continuation of U.S. application Ser. No. 11/010,795, filed on Dec. 13, 2004, now abandoned, which application claims the benefit of the filing date of U.S. Provisional Patent Application No. 60/529,348 filed Dec. 12, 2003, the disclosures of which are hereby incorporated herein by reference.

STATEMENT REGARDING FEDERALLY SPONSORED RESEARCH

The development of this invention was supported in part by the United States Department of Agriculture grant USDA-RS-58-5325-758. Therefore, the Government may have certain rights in the invention.

BACKGROUND OF THE INVENTION

The subject of plant protection against pathogens remains the area of utmost importance in agriculture. Many commercially valuable agricultural crops are prone to infection by plant viruses and fungi capable of inflicting significant damage to a crop in a given season, and drastically reducing its economic value. The reduction in economic value to the farmer in turn results in a higher cost of goods to ultimate purchasers.

Fungal pathogens contribute significantly to the most severe pathogen outbreaks in plants. Plants have developed a natural defense system, including morphological modifications in their cell walls, and synthesis of various anti-pathogenic compounds. See, e.g. Boller, et al., Plant Physiol. 74:442-444 (1984); Bowles, Annu. Rev. Biochem. 59:873-907 (1990); Joosten, et al., Plant Physiol. 89:945-951 (1989); Legrand, et al., Proc. Natl. Acad. Sci. USA 84:6750-6754 (1987); and Roby, et al., Plant Cell 2:999-1007 (1990). Several pathogenesis-related (PR) proteins have been shown to have anti-fungal properties and are induced following pathogen infection. These are different forms of hydrolytic enzymes, such as chitinases and β-1,3-glucanases that inhibit fungal growth in vitro by destroying fungal cell walls. See, e.g. Boller, et al., supra; Grenier, et al., Plant Physiol. 103:1277-123 (1993); Leah, et al., J. Biol. Chem. 266:1464-1573 (1991); Mauch, et al., Plant Physiol. 87:325-333 (1988); and Sela-Buurlage Buurlage, et al., Plant Physiol. 101:857-863 (1993).

Several attempts have been made to enhance the pathogen resistance of plants via recombinant methodologies using genes encoding pathogenesis-related proteins (such as chitinases and β-1,3-glucanases) with distinct lytic activities against fungal cell walls. See, e.g., Broglie, et al., Science 254:1194-1197 (1991); Vierheilig, et al., Mol. Plant-Microbe Interact. 6:261-264 (1993); and Zhu, et al., Bio/Technology 12:807-812 (1994). Recently, two other classes of genes have been shown to have potential in conferring disease resistance in plants. Wu, et al., Plant Cell 7:1357-1368 (1995), reports that a transgenic potato expressing the *Aspergillus niger* glucose oxidase gene exhibited increased resistance to *Erwinia carotovora* and *Phytophthora infestans*. The hypothesis is that the glucose oxidase-catalyzed oxidation of glucose produces hydrogen peroxide, which when accumulates in plant tissues, leads to the accumulation of active oxygen species, which in turn, triggers production of various anti-pathogen and anti-fungal mechanisms such as phytoalexins (see Apostol, et al., Plant Physiol. 90:109-116 (1989) and Degousee, Plant Physiol. 104:945-952 (1994)), pathogenesis-related proteins (Klessig, et al., Plant Mol. Biol. 26:1439-1458 (1994)), strengthening of the plant cell wall, (Brisson, et al., Plant Cell 6:1703-1712 (1994)), induction of systemic acquired resistance by salicylic acid (Chen, et al., Science 162:1883-1886 (1993)), and hypersensitive defense response (Levine, et al., Cell 79:583-593 (1994)).

In addition to the studies on virus resistance in plants, ribosome inactivating proteins (RIPs) have been studied in conjunction with fungal resistance. For example, Logeman, et al., Bio/Technology 10:305-308 (1992), report that an RIP isolated from barley endosperm provided protection against fungal infection to transgenic tobacco plants. The combination of barley endosperm RIP and barley class-II chitinase has provided synergistic enhancement of resistance to *Rhizoctonia solani* in tobacco, both in vitro and in vivo. See, e.g., Lea, et al., supra; Mauch, et al., supra; Zhu, et al., supra; and Jach, et al., The Plant Journal 8:97-109 (1995). PAP, however, has not shown antifungal activity in vitro. See Chen, et al., Plant Pathol. 40:612-620 (1991), which reports that PAP has no effect on the growth of the fungi *Phytophthora infestans, Colletotrichum coccodes, fusarium solani, fusarium sulphureum, Phoma foreata* and *Rhizoctonia solani* in vitro.

Lodge, et al., Proc. Natl. Acad. Sci. USA 90:7089-7093 (1993), report the *Agrobacterium tumefaciens*-mediated transformation of tobacco with a cDNA encoding wild-type pokeweed antiviral protein (PAP) and the resistance of the transgenic tobacco plants to unrelated viruses. Pokeweed antiviral protein (PAP) is a 29-kDa ribosome inactivating protein that catalytically removes two adenines and a guanine from the sarcin/ricin (S/R) loop of the large rRNA (Endo et al., J. Biol. Chem. 263:8735-8739 (1988); Hudak et al., J. Biol. Chem. 274:3859-3864 (2000) and disrupts binding of elongation factors to the ribosome (Montanaro et al., Biochemical J. 146:127-131 (1975); Osborn et al., European J. of Biocham. 193:401-407 (1990)). Aside from this demonstration of broad spectrum resistance to viruses, it has been demonstrated that when expressed in transgenic plants, PAP also confers broad spectrum antifungal (Zoubenko et al., Nature Biotechnol. 15:922-996 (1997); Zoubenko et al., Plant Mol. Biol. 44:219-229 (2000)) activity. It has also been shown that PAP recognizes its ribosomal substrate by binding to L3 (Hudak et al., J. Biol. Chem. 274:3858-3864 (1999)).

Lodge also reports, however, that the PAP-expressing tobacco plants (i.e., above 10 ng/mg protein) tended to have a stunted, mottled phenotype, and that other transgenic tobacco plants that accumulated the highest levels of PAP were sterile. U.S. Pat. Nos. 5,756,322 and 5,880,322 teach PAP mutants that when produced in plants exhibit less toxicity than wild-type PAP and exhibit biological activities (e.g., resistance to viruses, fungi and other pests) akin to wild-type PAP. It has also been reported that PAP II and PAP II mutants exhibit reduced phytotoxicity compared to wild-type PAP. See Wang, et al., Plant Mol. Biol. 38:957-964 (1998).

The trichothecenes are a family of low molecular weight sesquiterpenoid mycotoxins synthesized by various *Fusarium* species of fungi. Deoxynivalenol (DON) produced by *F. graminearum* or *F. culmorum* that causes *fusarium* head scab of wheat is a worldwide problem for human health concern and poses a major impact on animal production if present in feeds (Miller et al., Nat. Toxins 5:234-237 (1997)). Other trichothecenes include fusarenon X, trichothecin, verrucarin A, nivalenol, trichodermin, T-2 toxin and diacetoxyscirpenol (DAS). Trichothecenes inhibit peptidyl transferase reaction of protein synthesis by binding to the 60S ribosomal subunit. In addition, they cause membrane damage (Feinberg et al., C. S. 1989. Biochemical mechanism of actions of trichothecene mycotoxins. Pages 27-36 in: Trichothecene mycotoxixosis: Pathophysiological effects, Vol. 1. V. R. Beasley, ed. Boca Raton, Fla., CRC Press. Khachatourians, Canad. J. Physiol. Pharm. 68:1004-1008 (1990); Miller et al., Nat. Toxins 5:234-237 (1997)). Mitterbauer et al., 7$^{th}$ International Congress of Plant Pathology, Edinburgh, Scotland, 5.4.6. (1998) demonstrate that trichothecene resistance in the yeast, Saccharomyces cerevisiae, could result from either alterations in the target of trichothecenes, the ribosomal protein L3 or the increased drug efflux due to over-expression of a membrane transporter protein encoded by the PDR5 gene.

L3 is a highly conserved ribosomal protein that participates in the formation of the peptidyltransferase center that in turn allows elongation of the ribosome along the messenger RNA (mRNA). Hampl, et al., J. Biol. Chem. 256:2284-2288 (1981); Noller, J. Bacteriol. 175:5297-5300 (1993). L3 also plays an essential role in the catalysis of peptide bond formation. See, Green, et al., Annu. Rev. Biochem. 66:679-716 (1997). This is an essential step in protein synthesis in yeast, animals and higher plants. L3 is encoded by the rpl3 gene. Trichodermin, a substituted 12,13-epoxytrichothecene, is known to inhibit peptide bond formation by binding to the peptidyl transferase center. A mutation in the Rpl3 gene, designated tcm-1, which contains a single amino acid substitution of tryptophan to cysteine at position 255 (i.e., W255C) was initially identified in yeast by conferring resistance to trichodermin (Fried, et al., Proc. Natl. Acad. Sci. USA 78:238-242 (1981)). U.S. Pat. No. 6,060,646 to Harris, et al., teaches modified peptidyl transferase (L3) genes that provide resistance to trichothecene mycotoxins, such as the tcm-1 gene. Transgenic plants transformed with genes encoding L3 proteins are disclosed in WO 00/39291. The L3 proteins include wild-type L3, spontaneously occurring mutants and other non-naturally occurring mutants. It also teaches plants transformed with L3 genes and genes encoding ribosome inactivating proteins such as PAP.

Studies by Muhitch et al., Plant Science 157:201-207 (2000) demonstrated that tobacco plants transformed with either the Saccharomyces cerevisiae gene PDR5, which encodes a multi-drug transporter, or with the Fusarium sporotrichioides gene TRI101, which encodes a trichothecene 3-O-acetyltransferase, showed increased tolerance to the trichothecene 4,15-diacetoxyscirpenol (DAS). Even more recently, Harris et al., Physiol. Mol. Plant. Path. 58:173-181 (2001), showed that transgenic tobacco tissues transformed with a modified Rpl3 gene from rice displayed resistance to DON.

SUMMARY OF THE INVENTION

U.S. Pat. No. 6,060,646 to Harris, et al., teaches that the entire area between amino acid residues 240-263 of the L3 gene (which Harris refers to as the peptidyl transferase gene) is highly conserved in rice, Arabidopsis, yeast, bovines, humans, mice and rats, and is critical from the standpoint of conferring resistance to trichothecenes. It also teaches an L3 mutant, tcm-1, which results in an amino acid change at position 255 (W255C) in L3 that confers resistance to the trichothecene mycotoxin, thus substantiating this belief.

Applicants have discovered that N-terminal fragments of L3 that do not contain this region, when produced in plants, provide increased resistance to fungi, especially Fusarium, that produce trichothecenes. The N-terminal fragments of L3 do not contain the tcm-1 mutation (resulting in the amino acid change, W255C) in L3 that confers resistance to the trichothecene mycotoxin. Applicants have also discovered that expression of the N-terminal L3 fragments in transgenic plants confers better resistance to trichothecene mycotoxins than the full length L3 gene, and that co-expression of these fragments and a ribosome inactivating protein (RIP) such as pokeweed antiviral protein (PAP) serves to reduce or eliminate the toxicity associated with expression of the RIP. As a result, RIPs such as wild type PAP protein can be expressed at much higher levels in plants containing the N-terminal fragments of L3 than in plants containing the wild type PAP gene alone. Applicants discovered in the presence of the L3 N-terminal polypeptides, PAP does not auto-regulate i.e., degrade, its own mRNA, which results in higher expression levels and thus greater resistance to diseases caused by fungi, and that PAP does not depurinate the RNA of the cell, resulting in less toxicity to the cell.

Accordingly, a first aspect of the present invention is directed to a transgenic plant comprising an exogenous nucleic acid (i.e., a nucleic acid in addition to the native genome of the host) comprising a transgene functional therein and that encodes a polypeptide having at least the first 21 to about 99 N-terminal amino acid residues of a full-length eucaryotic L3 protein, or an analog of said polypeptide, wherein said plant exhibits increased resistance to toxins that target eucaryotic ribosomal L3 protein compared to a non-transgenic control plant. Such toxins include trichothecene mycotoxins, e.g., deoxynivalenol (DON) and 4,15-diacetoxyscirpenol (DAS). In some embodiments, the plant is cereal crop plant, e.g., maize, wheat, barley, rice and oat. In some embodiments, the polypeptide contains from at least the first 21 to 99 N-terminal amino acids, and in other embodiments, the polypeptide contains the first 100 N-terminal amino acids of a eurcaryotic ribosomal L3 protein. In some embodiments, the polypeptide has an amino acid sequence that corresponds to the yeast, rice, Arabidopsis or a tobacco L3 protein. In some embodiments, the exogenous nucleic acid further contains another transgene that encodes a RIP that targets a euraryotic ribosomal L3 protein, such as PAP, PAP-v, PAP II, ricin or a Shiga toxin. Seed generated from the transgenic plants are also provided.

A second aspect of the present invention is directed to a protoplast transformed with an exogenous nucleic acid having a transgene encoding a polypeptide having at least the first 21 to about 99 N-terminal amino acid residues of a full-length eucaryotic L3 protein or an analog thereof, wherein expression of the transgene in a transgenic plant generated from the transformed protoplast provides greater resistance to toxins that target a eucaryotic ribosomal L3 protein compared to a non-transgenic control plant. In some embodiments, the exogenous nucleic acid further comprises a transgene encoding a RIP protein that targets a eurcaryotic L3 ribosomal protein. The two transgenes can be introduced into the protoplast together by way of a single vector, or separately. Compositions containing the protoplasts and a suitable (e.g., culture or regeneration) medium, and callus derived from the protoplasts are also provided.

A third aspect of the present invention is directed to plant tissue transformed with an exogenous nucleic acid having a transgene encoding a polypeptide having at least the first 21 to about 99 N-terminal amino acid residues of a full-length eucaryotic L3 protein or an analog thereof, wherein expression of the nucleic acid in a transgenic plant generated from the transformed plant tissue provides greater resistance to toxins that target a eucaryotic ribosomal L3 protein compared to a non-transgenic control plant. In some embodiments, the exogenous nucleic acid further comprises a transgene encoding a RIP protein that targets a eurcaryotic L3 ribosomal protein. Compositions containing the plant tissue and a suitable (e.g., culture or regeneration) medium are also provided.

A fourth aspect of the present invention is directed to a vector functional in plant cells (e.g., suitable for use in transforming plants, or parts thereof such as protoplasts and plant tissue and which is replicable and viable therein), comprising a first nucleic acid fragment comprising a first promoter functional in a plant cell in operable association with a first nucleic acid encoding a polypeptide having at least the first 21 to about 99 N-terminal amino acid residues of a full-length eucaryotic L3 protein or an analog thereof. In some embodiments, the vector further contains a second nucleic acid fragment encoding an RIP protein e.g., PAP, that targets a eurcaryotic ribosomal L3 protein, in operable association with a second promoter functional in a plant cell, wherein the first and second promoters may be the same or different.

A fifth aspect of the present invention is directed to a method of making a transgenic plant having increased resistance to infestation by fungi that produce toxins that target a eurcaryotic L3 protein, e.g., trichothecene-producing fungi that produce deoxynivalenol (DON) or 4,15-diacetoxyscirpenol (DAS), comprising preparing a transgenic plant having a genome that contains an exogenous nucleic acid comprising a transgene encoding a polypeptide having at least the first 21 to about 99 N-terminal amino acid residues of a full-length eucaryotic L3 protein or an analog thereof, wherein expression of the transgene in the transgenic plant confers increased resistance to toxins that target a eucaryotic ribosomal L3 protein compared to a non-transgenic control plant.

A sixth aspect of the present invention is directed to a method of making a transgenic plant having resistance to infestation by fungi that produce toxins that target a eurcaryotic L3 protein, e.g., trichothecene mycotoxins deoxynivalenol (DON) and 4,15-diacetoxyscirpenol (DAS), comprising preparing a transgenic plant having a genome that contains a first exogenous nucleic acid having a first transgene encoding a polypeptide having at least the first 21 to about 99 N-terminal amino acid residues of a full-length eucaryotic L3 protein or an analog thereof, and a second exogenous nucleic acid having a second transgene encoding an RIP protein that targets a eucaryotic ribosomal L3 protein, wherein expression of the first and second transgenes in the transgenic plant confers increased resistance to the fungi, and with less toxicity to the plant compared to a transgenic control plant that contains the second transgene but does not contain the first transgene.

A further aspect of the present invention is directed to a transgenic non-human animal comprising an exogenous nucleic acid having a transgene encoding a polypeptide having at least the first 21 to about 99 N-terminal amino acid residues of a full-length eucaryotic L3 protein or an analog thereof, wherein expression of the transgene in the animal provides increased resistance toxins that target a eucaryotic ribosomal L3 protein e.g., trichothecene mycotoxins deoxynivalenol (DON) and 4,15-diacetoxyscirpenol (DAS), compared to a non-transgenic control non-human animal.

A further aspect of the present invention is directed to a pharmaceutical composition for treating fungal infections caused or mediated by a fungal toxin that targets a eucaryotic L3 ribosomal protein, comprising an anti-fungal effective amount of a polypeptide having at least the first 21 to about 99 N-terminal amino acid residues of a full-length eucaryotic L3 protein or an analog thereof, and a pharmaceutically acceptable carrier.

A further aspect of the present invention is directed to a method of reducing toxicity associated with a ribosome inactivating protein (RIP) that targets a eucaryotic ribosomal L3 protein, in an animal in need thereof, comprising administering to an animal in need thereof, a composition comprising an effective amount of a polypeptide having at least the first 21 to about 99 N-terminal amino acid residues of a full-length eucaryotic L3 protein, or an analog thereof. In some embodiments, the RIP is PAP, e.g., wild type PAP. The L3 polypeptide or analog thereof can be administered prior to, simultaneous with or after administration of the RIP, such that it is present in animal or human to exert its anti-cytotoxic effect of or on the RIP. In some embodiments, the RIP is conjugated to a ligand that binds a receptor present on or in the target cell. The methods are particularly useful in the treatment of cancer and viral infections (e.g., HIV) in mammals, preferably humans.

A further aspect of the present invention is directed to a polypeptide or analog thereof, comprising at least the first 21 to about 99 N-terminal amino acid residues of a full-length eucaryotic L3 protein.

A further aspect of the present invention is directed to a polynucleotide having a sequence encoding a polypeptide having at least the first 21 to 99 N-terminal amino acid residues of a full-length eucaryotic L3 protein. Constructs containing the polynucleotides, e.g., vectors such as plasmids functional (e.g., replicable and viable) in a host cell such as a bacterial, yeast or animal cell, wherein the polynucleotide is operably associated with a promoter functional in the cell or non-cellular system in which the polynucleotide is intended to be expressed, and host cells transformed with the polynucleotide, are further provided. The phrase "targets a eucaryotic ribosomal L3 protein", as used herein, includes interaction between the L3 protein and a toxin such as DON or DAS, or a RIP such as PAP, that results in depurination of ribosomes and toxicity to the cell. By the term "about 99", it is meant to include polypeptides having the first 100 N-terminal amino acid residues of a eucaryotic L3 ribosomal protein.

These and other aspects of the present invention are more fully described in the sections that follow.

BRIEF DESCRIPTION OF THE DRAWINGS

FIGS. 9A, B and C show gene expression of tobacco ribosomal protein L3A and L3B analyzed by real-time quantitative PCR and Western blot. In real-time PCR (A. and B.), Oligo d(T) was used to prime the total RNA to synthesize the first-strand cDNA with SuperScript RT. Real-time PCR was performed with specific primers for tobacco L3A and L3B. The gene expression level was calculated as ddCT using tobacco tubulin gene as an internal control. The experiment was repeated three times. In Western blot (C.), 10 μg protein of each cytosolic sample was electrophoresed on 10% SDS-PAGE gel and transferred to nitrocellulose membrane. The blot was probed with L3 polyclonal antibody and PEPc to show equal loading. Lanes 1-12: wt nn, wt NN, NT243-64, NT243-81, NT245-12, NT245-21, NT250-11, NT250-41, NT252-11, NT252-41, PAPx and PAPv.

FIGS. 10A, B and C show gene expression of yeast L3 or L3(1-100) and PAP was analyzed by real-time quantitative and Western blot. In real-time PCR (A. and B.), oligo d(T) was used to prime the total RNA to synthesize the first-strand cDNA with SuperScript RT. Real-time PCR was performed with L3Δ- and PAP-specific primers. The gene expression level was calculated as ddCT using tobacco tubulin as an internal control. In Western blot (C.), 10 μg protein of each ribosomal sample was electrophoresed on 10% SDS-PAGE gel and transferred to nitrocellulose membrane. The blot was probed with PAP polyclonal antibody. Lanes 1-8: wt nn, PAPx, PAPv, NT243-64, NT243-81, NT245-12, NT245-21 and PAP standard.

FIGS. 12 (SEQ ID NOS 13 and 14), 13 (SEQ ID NOS 15-16 and 42-44) and 14 (SEQ ID NOS 17 and 18) show nucleotide and corresponding amino acids sequences of the yeast wild-type L3 gene (rpl3), the tobacco "8d" L3 and "10d") proteins, and the mutant tcm1 gene.

FIGS. 15 and 16 show polynucleotide and corresponding amino acid sequences of a wild-type PAP (SEQ ID NOS 19 and 20) and PAP II (SEQ ID NOS 21 and 22), respectively.

FIGS. 17, 18 and 19 show the polynucleotide and corresponding amino acid sequences of ricin (SEQ ID NOS 23 and 24) and two different Shiga toxins (SEQ ID NOS 25-26 and 27-28), respectively.

DETAILED DESCRIPTION OF THE INVENTION

Figure 11A:
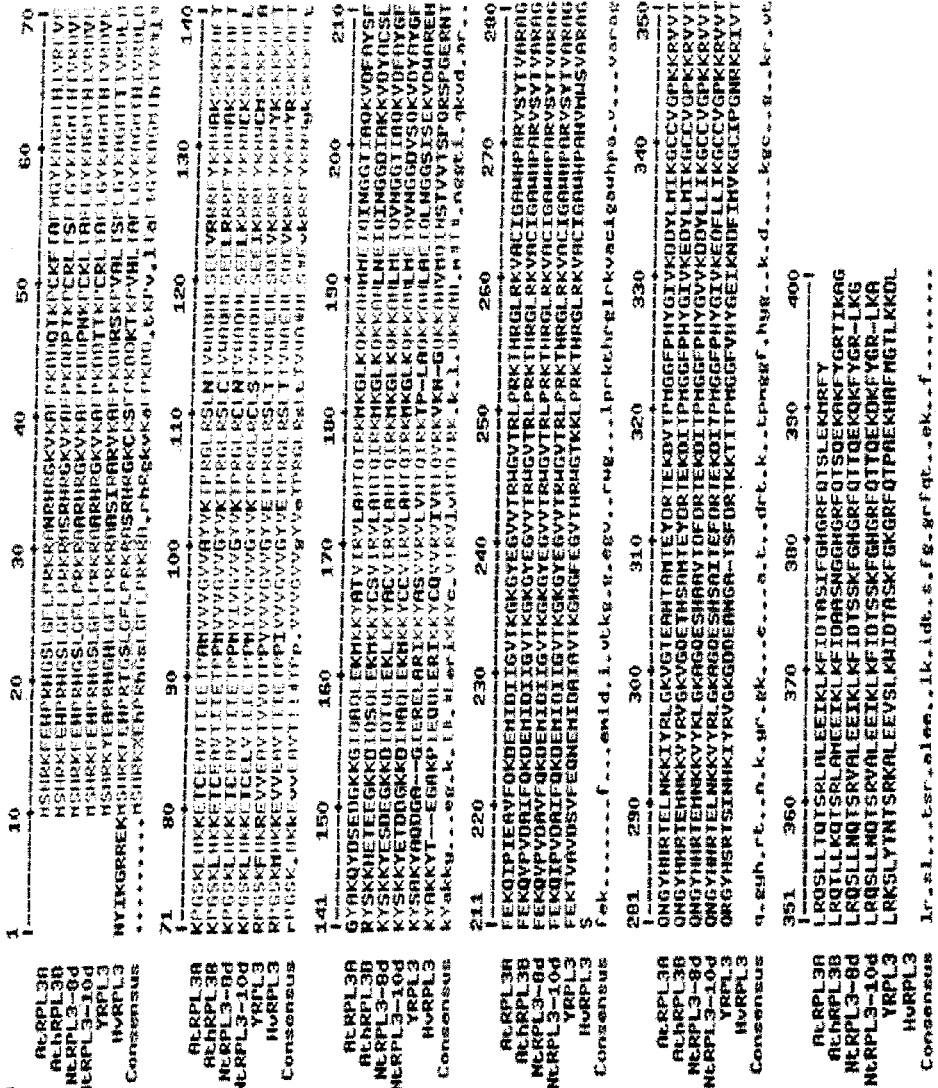
FIGS. 11A and B show alignments of the amino acid sequences of full-length L3 proteins from *Arabidopsis* (i.e., AtRPL3A and AthRPL3B), *Nicotiana tabacum* (i.e., NtRPL3-8d and NtRPL3-10d), yeast (i.e., YRPL3), and rice (i.e., HvRPL3) various L3 proteins, and their first 100 amino acid residues, respectively (SEQ ID NOS 1-12).

A primary aspect of the present invention is directed to DNA sequence that encodes a polypeptide having at least the first 21 to about 99 N-terminal amino acid residues of a full-length eucaryotic L3 protein (hereinafter "L3 N-terminal polypeptides", or "L3 N-terminal polypeptide fragments," or an analog of the L3 polypeptide. Eucaryotic L3 proteins include, but are not limited to human, yeast, bovine, mice, rat and higher plant (e.g., rice wheat, barley, and tobacco) and *Arabidopsis* L3 proteins. An alignment of the amino acid sequences of full-length L3 proteins from *Arabidopsis* (i.e., AtRPL3A and AthRPL3B), *Nicotiana tabacum* (i.e., NtRPL3-8d and NtRPL3-10d), yeast (i.e., YRPL3), and rice (i.e., HvRPL3) various L3 proteins, and their first 100 amino acid residues, are illustrated in FIGS. 11A and B. Nucleotide and corresponding amino acids sequences of the yeast wild-type L3 gene (rpl3), the tobacco "8d" L3 and "10d) proteins, and the mutant tcm1 gene, are illustrated in FIGS. 12, 13 and 14.

The polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of a eurcaryotic L3 protein. These polypeptides are referred to herein as L3(1-21), L3(1-22), L3(1-23), L3(1-24), L3(1-25), L3(1-26), L3(1-27), L3(1-28), L3(1-29), L3(1-30), L3(1-31), L3(1-32), L3(1-33), L3(1-34), L3(1-35), L3(1-36), L3(1-37), L3(1-38), L3(1-39), L3(1-40), L3(1-41), L3(1-42), L3(1-43), L3(1-44), L3(1-45), L3(1-46), L3(1-47), L3(1-48), L3(1-49), L3(1-50), L3(1-51), L3(1-52), L3(1-53), L3(1-54), L3(1-55), L3(1-56), L3(1-57), L3(1-58), L3(1-59), L3(1-60), L3(1-61), L3(1-62), L3(1-63), L3(1-64), L3(1-65), L3(1-66), L3(1-67), L3(1-68), L3(1-69), L3(1-70), L3(1-71), L3(1-72), L3(1-73), L3(1-74), L3(1-75), L3(1-76), L3(1-77), L3(1-78), L3(1-79), L3(1-80), L3(1-81), L3(1-82), L3(1-83), L3(1-84), L3(1-85), L3(1-86), L3(1-87), L3(1-88), L3(1-89), L3(1-90), L3(1-91), L3(1-92), L3(1-93), L3(1-94), L3(1-95), L3(1-96), L3(1-97), L3(1-98) and L3(1-99), respectively. L3(1-99) is also referred to herein, particularly in the working examples, as "L3Δ1-99" or L3Δ99". By way of specific example, as shown in FIG. 11B, L3(1-99) in yeast has an amino acid (and corresponding nucleotide) sequence as set forth below.

Yeast L3(1-99):

```
                                        (SEQ ID NO: 30)
+1 MSHRKYEAPRHGHLGFLPRKRAASIRARVKAFPKDDRSKPVALTSFL

GYKAGMTIVRDLDRPGSKFHKREVVEAVTVVDTPPVVVVGVVGYVETPRG

L +99

Yeast L3 (1-99) nucleotide
                                        (SEQ ID NO: 31)
+1 ATGTCTCACAGAAAGTACGAAGCACCACGTCACGGTCATTTAGGTTT

CTTGCCAAGAAAGAGAGCTGCCTCCATCAGAGCTAGAGTTAAGGCTTTTC

CAAAGGATGACAGATCCAAGCCAGTTGCTCTAACTTCCTTCTTGGGTTAC

AAGGCTGGTATGACCACCATTGTCAGAGATTTGGACAGACCAGGTTCTAA

GTTCCACAAGCGTGAAGTTGTCGAAGCTGTCACCGTTGTTGACACTCCAC

CAGTTGTCGTTGTTGGTGTTGTCGGTTACGTCGAAACCCCAAGAGGTTTG

A +298.
```

Thus, the amino acid sequences corresponding to yeast L3(1-21) to L3(1-99) may be easily ascertained, as follows:

```
L3 (1-21)
MSHRKYEAPRHGHLGFLPRKR;              (SEQ ID NO: 32)

L (1-22)
MSHRKYEAPRHGHLGFLPRKRA;             (SEQ ID NO: 33)

L3 (1-23)
MSHRKYEAPRHGHLGFLPRKPAA;            (SEQ ID NO: 34)

L3 (1-24
MSHRKYEAPRHGHLGFLPRKRAAS;           (SEQ ID NO: 35)

L3 (1-25)
MSHRKYEAPRHGHLGFLPRKRAASI, etc.     (SEQ ID NO: 36)
```

It is readily apparent that although the L3 proteins illustrated in FIGS. 11A and B possess a high level of sequence similarity, there are differences in various first 99 residues. Such differences occur at positions 6 (F or Y), 8 (H or A), 11 (H or T), 13 (S or H), 23 (N, S or A), 24 (R or S), 25 (H or I), 27 (G or A) 28 (K or R), 29 (V or C), 31 (A or S), 37(Q, P, T, R or K), 38 (T, N, or S), 41 (C or V), 42 (K, R, A, or H), 43 (F or L) 45 (A or S), 47 (M or L), 55 (H or T), 60 (V or L), 61 (E or D), 62 (K or R), 67, (L, F or M), (K or R), 72 (T or V), 73 (C or V), 75 (A or L), 78 (I or V), 79 (I or V), 80 (E or D) 83 (A or P), 84 (M, V or I), 85 (V or I), 86 (V or I), 91 (A or G) and 94 (K or E). Thus, L3(1-21)-L3(1-99) from yeast, as well as from rice, Arabidopsis, and tobacco L3 proteins illustrated in FIG. 11B constitute specific examples of polypeptides of the present invention. Yet other polypeptides of the present invention may be based on amino acid sequences of L3 proteins not specifically disclosed herein in accordance by resort to the literature or standard techniques (e.g., probing genomic or cDNA libraries with probes corresponding to conserved regions of L3 proteins as shown in FIGS. 11A and B.

In certain embodiments, depending on the nature of the restriction enzyme and the vector, use of L3(1-99) will result in expression of L3(1-100). This would occur, for instance, when L3 DNA starting material is produced by treating yeast L3 DNA with BglII, inserting the DNA encoding L3(1-99) into a vector with a BamHI or BglII site, and then transforming a cell with the vector. In this case, an "R" codon would be added. Since native yeast L3 contains an R at residue 100, the corresponding expression product would be L3 (1-100). Thus, the polypeptides of the present invention include L3(1-100). L3(1-100) is also referred to herein, particularly in the working examples, as "L3Δ100" or L3Δ1-100".

Figure 25:
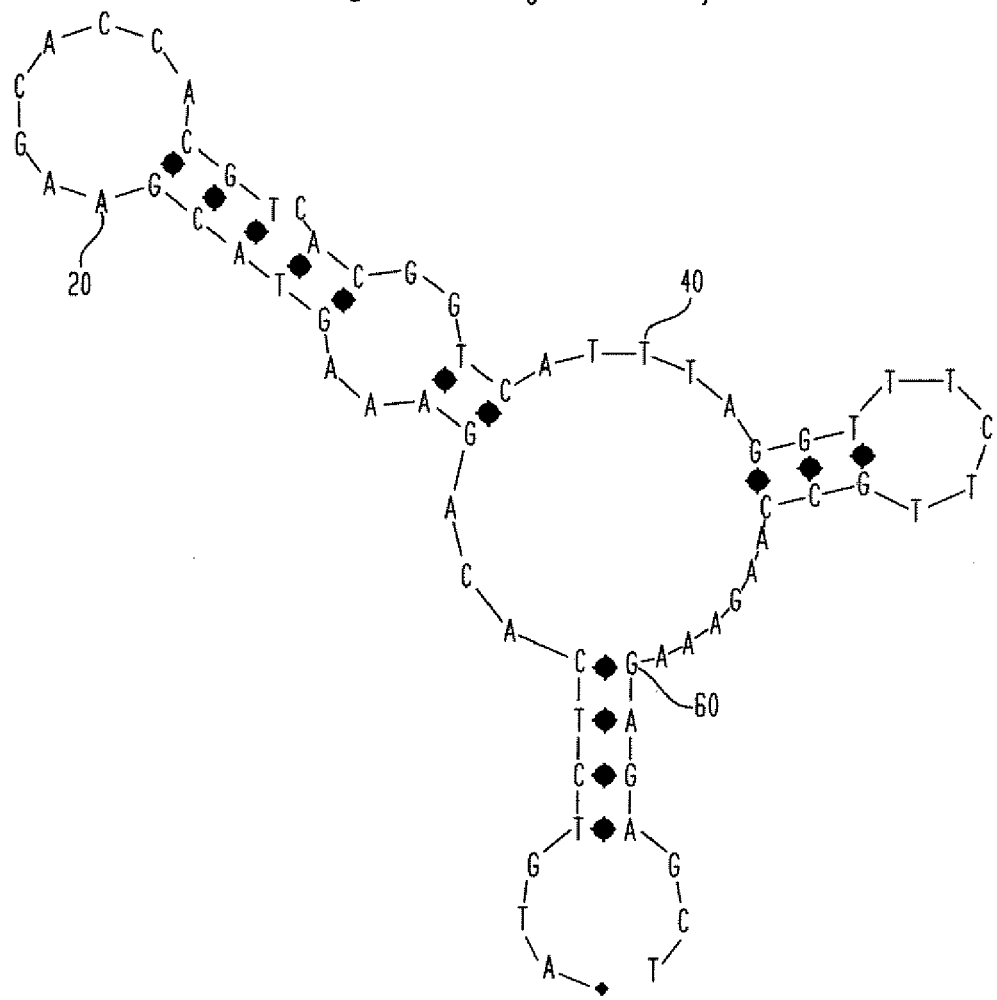
FIG. 25 schematically shows the stem loop structure (SEQ ID NO: 29) of the 5' end of L3 mRNA that encodes amino acid residues 1-21.

The present invention also includes analogs of the L3 N-terminal polypeptides. In general, analogs differ from the native sequences of the L3 N-terminal polypeptides In general, analogs of the polypeptides in terms of amino acid alterations or modifications, substitutions, insertions or deletions, and preferably in terms of one or more conservative or non-conservative amino acid substitutions. In preferred embodiments, the analogs differ in terms of one or more conservative amino acid substitutions, particularly in any of amino acids 1-21, which as illustrated in FIG. 25, the mRNA of which forms a secondary stem loop structure. Referring again to FIG. 11B, L3(1-21) from yeast may have an "H" residue substituted for the "A" residue at position 8. There is relatively more latitude for analogs of L3 N-terminal polypeptides that contain additional amino acids, i.e., having from at least the first 22 to about 99 amino acids, and amino acids substitutions may be conservative or non-conservative in nature. Analogs of the present invention also possess the desired properties, e.g., providing increased resistance to toxins (e.g., trichodermin toxins) that target eurcaryotic L3 ribosomal proteins when present in a given host, and when present along with an RIP that targets a eurcaryotic L3 ribosomal protein, serves to reduce toxicity associated with the RIP.

It is also well understood by the skilled artisan that there is a limit to the number of changes that may be made within a portion of the molecule and still result in a molecule with an acceptable level of equivalent biological activity of function. There are several general guidelines to consider in determining whether a given change in an amino acid sequence will result in an unacceptable change in the desired activity. First, tolerance to change increases with the length of the peptide or protein. It is also well understood that where certain residues are shown to be particularly important to the biological or structural properties of a polyamino acid, such residues may not generally be exchanged. Amino acid substitutions are generally based on the relative similarity of the various types of amino acid side-chains, for example, their hydrophobicity, hydrophilicity, charge, size, and the like. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Therefore, based upon these considerations, arginine, lysine and histidine; alanine, glycine and serine; and phenylalanine, tryptophan and tyrosine; are defined herein as biologically functional equivalents. To effect more quantitative changes, the hydropathic index of amino acids may be considered. Each amino acid has been assigned a hydropathic index on the basis of its hydrophobicity and charge characteristics, which are as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein, and correspondingly a polyamino acid, is generally understood in the art. It is known that certain amino acids may be substituted for other amino acids having a similar hydropathic index or score and still retain a similar biological activity. In making changes based upon the hydropathic index, the substitution of amino acids whose hydropathic indices are within 2 is preferred, those which are within approximately 1 are particularly preferred, and those within approximately 0.5 are even more particularly preferred.

It is also understood in the art that the substitution of like amino acids can be made effectively on the basis of hydrophilicity. As disclosed in U.S. Pat. No. 4,554,101, the following hydrophilicity values have been assigned to amino acid residues: arginine (+3.0); lysine (+3.0); aspartate (+3.0±1); glutamate (+3.0±I); serine 5 (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. In some embodiments, analogs of the polypeptides contain amino acid substitutions in the positions where as shown in FIGS. 11A and B, variability exists.

Expression of a transgene encoding the polypeptide or analog in a plant (transformed with the transgene) confers increased resistance to toxins and antibiotics that target eurcaryotic ribosomal protein L3, and which are toxic to and cause disease in plants. Such toxins include trichothecene mycotoxins (also referred to as sesquiterpene antibiotics) such as fusarenon X, trichothecin, verrucarin A, nivalenol, trichodermin, T-2 toxin, diacetoxyscirpenol (DAS) and deoxynivalenol (DON). Trichothecenes are a class of toxic, sesquiterpenoid secondary metabolites that are produced mainly by plant pathogenic fungi (Fernandez-Lobato et al., Biochem. J. 267:709-713 (1990)). *Fusarium graminearum* and *F. culmorum* produce the trichothecene mycotoxins deoxynivalenol (DON), also known as vomitoxin, which contaminates a substantial portion of agricultural crops such as wheat, barley and maize, and 4,15-diacetoxyscirpenol (DAS). The resistance to these toxins and the diseases they cause will be greater than the level of resistance exhibited by a non-transgenic control plant. Transgenic plants of the present invention particularly show greater resistance to at least two trichothecene mycotoxins, DON and DAS (and thus the diseases they cause), than a non-transgenic control plant of the same species. Resistance may also be about equal to or greater than a transgenic control plant that expresses an exogenous transgene that encodes wild type yeast L3 (as shown in FIG. 12). This determination can be made in accordance with the protocols described in the working examples.

Thus, plants transformed with nucleic acids encoding L3 N-terminal polypeptide or an analog thereof exhibit increased resistance to diseases and infections or infestations caused or mediated by trichothecene mycotoxins, particularly DON and DAS. Thus, in general, transgenic plants of the present invention will exhibit resistance against diseases caused by *Fusarium* infection (e.g., root rot of bean, dry rot of potatoes, head blight (scab) in wheat), *Pythium* (one of the causes of seed rot, seedling damping off and root rot), *Phytophthora* (the cause of late blight of potato and of root rots, and blights of many other plants), *Bremia, Peronospora, Plasmopara, Pseudoperonospora* and *Sclerospora* (causing downy mildews), *Erysiphe graminis* (causing powdery mildew of cereals and grasses), *Verticillium* (causing vascular wilts of vegetables, flowers, crop plants and trees), *Rhizoctonia* (causing damping off disease of many plants and brown patch disease of turfgrasses), *Cochliobolus* (causing root and foot rot, and also blight of cereals and grasses), *Giberella* (causing seedling blight and foot or stalk rot of corn and small grains), *Gaeumannomyces* (causing the take-all and whiteheads disease of cereals), *Sclerotinia* (causing crown rots and blights of flowers and vegetables and dollar spot disease of turfgrasses), *Puccinia* (causing the stem rust of wheat and other small grains), *Ustilago* (causing corn smut), *Magnaporthae* (causing summer patch of turfgrasses), and *Schlerotium* (causing southern blight of turfgrasses). Other important fungal diseases include those caused by *Cercospora, Septoria, Mycosphoerella, Glomerella, Colletotrichum, Helminthosporium, Alterneria, Botrytis, Cladosporium* and *Aspergillus*. Since the L3 N-terminal polypeptides also affect viral frameshifting, the plants might also exhibit resistance to certain plant viruses e.g., barley yellow dwarf virus, potato leafroll virus, citrus tristeza virus and beet western yellows virus.

Nucleic acids encoding the L3 N-terminal polypeptides and analogs thereof of the present invention can be prepared in accordance with standard procedures such as cloning or synthetic synthesis. In addition to the nucleotide sequence for L3(1-99) from yeast that is set forth above, representative nucleic acid sequences are contained in FIGS. 11A and B, 12, 13 and 14. That is, the portion of the full-length polynucleotide that encodes the L3 N-terminal polypeptide may be easily designed by introducing a "stop" codon immediately after the C-terminal amino acid residue of the desired N-terminal polypeptide. For example, a representative polynucleotide encoding yeast L3(1-21) may have a sequence as follows: 5' atgtctcaca gaaagtacga agcaccacgt cacggtcatt taggtttctt gccaagaaag agataa 3' (SEQ ID NO: 37). Allelic versions of the sequences and homologous sequences encoding L3 proteins may be found in eurcaryotic cell types other than plants such as humans and rodents (e.g., rats and mice). For example, nucleic acid sequences encoding L3 proteins are obtainable from a variety of publicly accessible web sites related to various genome projects. Yet other nucleic acids having sequences encoding the L3 N-terminal polypeptides and analogs thereof may be prepared based on considerations of the degeneracy of the code and the codon preference of a given host cell, e.g., plant or other eucaryotic cell such as an animal or human cell, in which the polynucleotide is to be expressed.

In other embodiments of the present invention, transgenic plants containing nucleic acids encoding L3 N-terminal polypeptides and analogs also contain exogenous nucleic acids encoding a ribosome inactivating protein (RIP) such as a Pokeweed Anti-viral Protein (PAP) protein. PAP proteins include wild-type PAP, variant PAP (i.e. PAP-v, which differs from wild-type PAP in terms of the double amino acid substitutions, Leu20Arg and Tyr49His), PAP mutants having reduced toxicity (e.g., phytotoxicity) compared to wild-type PAP or PAP-v, and which have intact catalytic active site amino acid residues (Glu176 and Arg179), and PAP II proteins. Wild-type PAP, PAP-v and various PAP mutants are described in U.S. Pat. Nos. 5,756,322 and 5,880,322. Aside from the differences in the codons resulting in the two amino acid changes, the third change in the PAP-v nucleotide sequence (i.e., TCG→TCA for the first occurring Ser in the signal sequence) has no effect on the amino acid sequence. PAP II is reported in Poyet, et al., FEBS Letters 347:268-272 (1994). The term "PAP-II," is inclusive of the 310 amino acid polypeptide disclosed in Poyet, et al., the 285-amino acid polypeptide containing amino acid residues 26-310 of said polypeptide (i.e., "PAP II (1-285)") and which excludes the N-terminal twenty-five (25)-amino acid signal sequence and analogs of PAP II (1-285) such as fragments and mutants (e.g., amino acid additions, deletions and substitutions) that substantially retain PAP II anti-viral and anti-fungal properties and exhibit reduced phytotoxicity compared to PAP. PAP II and PAP II mutants are described in WO 99/60843, published Dec. 2, 1999. Polynucleotide and corresponding amino acid sequences of a wild-type PAP and PAP II are illustrated in FIGS. 15 and 16, respectively. Other RIPS useful in the present invention include ricin toxin and Shiga toxin. Nucleotide and corresponding amino acid sequences of ricin and two different Shiga toxins are illustrated in FIGS. 17, 18 and 19, respectively. Other RIPs include but are not limited to trichosanthin, saporin, mirabilis antiviral protein, momordin, dianthin and gelonin.

Transgenic plants expressing exogenous nucleic acids encoding a RIP protein will exhibit increased resistance to plant fungi that produce toxins that target eucaryotic L3 ribosomal proteins. Thus, expression of an RIP may provide increased resistance to diseases caused by fungi such as *Fusarium* infection (e.g., root rot of bean, dry rot of potatoes, head blight (scab) in wheat), *Pythium* (one of the causes of seed rot, seedling damping off and root rot), *Phytophthora* (the cause of late blight of potato and of root rots, and blights of many other plants), *Bremia, Peronospora, Plasmopara, Pseudoperonospora* and *Sclerospora* (causing downy mildews), *Erysiphe graminis* (causing powdery mildew of cereals and grasses), *Verticillium* (causing vascular wilts of vegetables, flowers, crop plants and trees), *Rhizoctonia* (causing damping off disease of many plants and brown patch disease of turfgrasses), *Cochliobolus* (causing root and foot rot, and also blight of cereals and grasses), *Giberella* (causing seedling blight and foot or stalk rot of corn and small grains), *Gaeumannomyces* (causing the take-all and whiteheads disease of cereals), *Schlerotinia* (causing crown rots and blights of flowers and vegetables and dollar spot disease of turfgrasses), *Puccinia* (causing the stem rust of wheat and other small grains), *Ustilago* (causing corn smut), *Magnaporthae* (causing summer patch of turfgrasses), and *Schlerotium* (causing southern blight of turfgrasses). Other important fungal diseases include those caused by *Cercospora, Septoria, Mycosphoerella, Glomerella, Colletotrichum, Helminthosporium, Alterneria, Botrytis, Cladosporium* and *Aspergillus*.

RIPs might also provide increased resistance to viruses including but not limited to RNA viruses e.g., citrus tristeza virus, potexviruses such as (PVX, potato virus X), potyvirus (PVY), cucumber mosaic virus (CMV), tobacco mosaic viruses (TMV), barley yellow dwarf virus (BYDV), wheat streak mosaic virus, potato leaf roll virus (PLRV), plumpox virus, watermelon mosaic virus, zucchini yellow mosaic virus, papaya ringspot virus, beet western yellow virus, soybean dwarf virus, carrot read leaf virus and DNA plant viruses such as tomato yellow leaf curl virus. See also Lodge, et al., PNAS USA 90:7089-7093 (1993); Tomlinson, et al., J. Gen. Virol. 22:225-232 (1974); and Chen, et al., Plant Pathol. 40:612-620 (1991).

Since the RIPs of the present invention target L3 ribosomal proteins and as a result, are toxic to eucaryotic cells, the co-expression or transcription of a nucleic acid encoding a L3 N-terminal polypeptide will reduce such toxicity, relative to a control plant expressing an RIP transgene but which does not contain the L3 N-terminal polypeptide-encoding transgene.

Nucleic acids encoding L3 N-terminal polypeptides and analogs thereof, and in some embodiments, a PAP protein, can be introduced and expressed in a variety of plants including higher plants such as flowering plants, including both monocots and dicots, and preferably crop plants and cereal crop plants, in accordance with standard transformation techniques for the plant type of interest. See U.S. Pat. No. 5,675,322 (and references cited therein), Horsch, et al., Science 227:1229-1231 (1985); and Hartman, et al., Bio/technology 12:919-923 (1994). Preparation of expression cassettes and vectors for the introduction of the L3 nucleic acid into plant cells, protoplasts, whole plants and plant parts are also well known in the art. In general, any cloning vector can be used; the choice will reflect the host in which the final transformation is made and the manner in which transformation is accomplished. Vectors suitable for *Agrobacterium* transformation typically carry at least one T-DNA border sequence. These include vectors such as pBIN19 (Bevan, Nucleic Acids Research 12:8711-8721 (1984)) and pCIB200 (EP 0 332 104). Transformation without the use of *Agrobacterium tumefaciens* circumvents the requirement for T-DNA sequences in the chosen transformation vector and consequently vectors lacking these sequences can be utilized in addition to vectors that contain T-DNA sequences. Transformation techniques that do not rely on *Agrobacterium* include transformation via particle bombardment, protoplast uptake (e.g. PEG and electroporation) and microinjection. For example, pCIB3064 is a pUC-derived vector suitable for the direct gene transfer technique in combination with selection by the herbicide basta (or phosphinothricin), as described, for example, in WO 93/07278 and Koziel et al., Biotechnology 11:194-200 (1993).

For the transformation of plants, the cloning vector can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by directing the addition of polyadenylic acid tracks to the 3' end of the mRNA precursor. Polyadenylation signals are commonly recognized by the presence of homology to the canonical form 5' AATAAA-3' although variations are not uncommon. Examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the modified peptidyl transferase gene of the present construct can be used for expression in plants, without any additional region. The vectors of the present invention can also contain a suitable promoter functional in the host. In the case of monocot transformation, for example, preferred promoters include the CaMV 35S promoter, ubiquitin promoter, and the actin promoter. For dicots, mention may be made of the CaMV 35S promoter, the enhanced CaMV 35S promoter, the L3 promoter or the FMV (figwort mosaic virus) promoter. In the embodiments of the present invention that entail transformation of a plant with a nucleic acid encoding a PAP protein, it is preferred to place the nucleic acids encoding L3Δ or analog thereof, and PAP under the control of separate regulatory units and polyadenylation sites (i.e., to prepare polycistronic rather than monocistronic expression cassettes. An expression cassette containing the nucleic acid(s) of the present invention may be inserted into a plant transformation vector by standard recombinant DNA methods. Alternatively, some or all of the elements of the expression cassette may be present in the vector, and any remaining elements may be added to the vector as necessary.

Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described in Paszkowski et al., EMBO J. 3:2717-2722 (1984), Potrykis et al., Mol. Gen. Genet. 199:169-177 (1985), Reich et al., Biotechnology 4:1001-1004 (1986), and Klein et al., Nature 327: 70-73 (1987). In each case the transformed cells are regenerated to whole plants using standard techniques.

*Agrobacterium*-mediated transformation is a preferred technique for transformation of dicotyledons (dicots) because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (poplar)). *Agrobacterium* transformation typically involves the transfer of the binary vector carrying the foreign DNA of interest (e.g. pCIB200 or pCIB2001) to an appropriate *Agrobacterium* strain which may depend on the complement of vir genes carried by the host *Agrobacterium* strain either on a co-resident plasmid or chromosomally (e.g. strain CIB542 for pCIB200 (Uknes et al. Plant Cell 5:159-169 (1993)). The transfer of the recombinant binary vector, to *Agrobacterium* is accomplished by a triparental mating procedure using *E. coli* carrying the recombinant binary vector, a helper *E. coli* strain which carries a plasmid such as pRK2013 which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16:9877 (1988)). Transformation of the target plant species by recombinant *Agrobacterium* usually involves co-cultivation of the *Agrobacterium* with explants from the plant and follows protocols known in the art. Transformed tissue is regenerated on selectable medium carrying an antibiotic or herbicide resistance marker present between the binary plasmid T-DNA borders.

Preferred transformation techniques for monocots include direct gene transfer into protoplasts using PEG or electroporation techniques and particle bombardment into callus tissue. Transformation can be undertaken with a single DNA species or multiple DNA species (i.e. co-transformation) and both these techniques are suitable for use with this invention. Co-transformation may have the advantages of avoiding complex vector construction and generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., Biotechnology 4:1093-1096 (1986)).

Published European Patent Applications EP 0 292 435 and EP 0 392 225, and PCT application WO 93/07278 describe techniques for the preparation of callus and protoplasts of maize, transformation of protoplasts using PEG or electroporation, and the regeneration of maize plants from transformed protoplasts. Gordeon-Kamm et al., Plant Cell 2:603-618 (1990), and Fromm et al., Biotechnology 11:194-200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for Japonica-types and Indica-types (Zhange et al., Plant Cell Rep. 7:739-384 (1988); Shimamoto et al. Nature 338:274-277 (1989); Datta et al. Biotechnology 8:736-740 (1990)). Both types are also routinely transformable using particle bombardment (Christou et al. Biotechnology 9:957-962 (1991)).

Patent Application EP 0 332 581 described techniques for the generation, transformation and regeneration of Pooideae protoplasts. Furthermore, wheat transformation has been described by Vasil et al., Biotechnology 10:667-674 (1992), using particle bombardment into cells of type C long-term regenerable callus, and also by Vasil et al., Biotechnology 11:1553-1558 (1993), and Weeks et al., Plant Physiol. 102: 1077-1084 (1993), using particle bombardment of immature embryos and immature embryo-derived callus.

Transformation of monocot cells such as *Zea mays* can be achieved by bringing the monocot cells into contact with a multiplicity of needle-like bodies on which these cells may be impaled, causing a rupture in the cell wall thereby allowing entry of transforming DNA into the cells. See U.S. Pat. No. 5,302,523. Transformation techniques applicable to both monocots and dicots are also disclosed in the following U.S. Pat. Nos. 5,240,855 (particle gun); 5,204,253 (cold gas shock accelerated microprojectiles); 5,179,022 (biolistic apparatus); 4,743,548 and 5,114,854 (microinjection); and 5,149, 655 5,120,657 (accelerated particle mediated transformation); 5,066,587 (gas driven microprojectile accelerator); 5,015,580 (particle-mediated transformation of soy bean plants); 5,013,660 (laser beam-mediated transformation); and 4,849,355 and 4,663,292. See also section 6.2.7 of U.S. Pat. No. 6,720,014, which describes transformation of monocots.

To aid in identification of transformed cells, the vectors may further contain a selectable marker (e.g., a reporter gene). For certain target species, different antibiotic or herbicide selection markers may be preferred. Selection markers used routinely in transformations include the nptII gene which confers resistance to kanamycin (Messing and Vierra, Gene 19:259-268 (1982); Bevan et al., Nature 304:184-187 (1983)), the bar gene which confers resistance to the herbicide phosphinothricin (White et al., Nucl. Acids Res. 18:1062 (1990); Spencer et al., Theor. Appl. Genet. 79:625-631 (1990)), the hph gene which confers resistance to the antibiotic hygromycin (Blochinger & Diggelmann, Mol. Cell. Biol. 4:2929-2931)), and the dhfr gene, which confers resistance to methotrexate). Selection of successful transformation events may also be accomplished using a CGS gene as a reporter. See, e.g., WO 00/55303, published Sep. 21, 2000, to Tumer, et al.

The thus-transformed plant cells or plant tissue are then grown into full plants in accordance with standard techniques. Transgenic seed can be obtained from transgenic flowering plants in accordance with standard techniques. Likewise, non-flowering plants such as potato and sugar beets can be propagated by a variety of known procedures. See, e.g., Newell, et al. Plant Cell Rep. 10:30-34 (1991) (disclosing potato transformation by stem culture).

Techniques for transforming plants and regenerating plants are also disclosed in Lanfranco, Riv. Biol. 96(1):31-54 (2003); Job, Biochimie 84(11):1105-10 (2002); Taylor, et al., DNA Cell Biol. 21(12):963-77 (2002); Rakoczy-Trojanowska, Cell Mol. Biol. Lett. 7(3):849-58 (2002); Ow, Plant Mol. Biol. 48(1-2):183-200 (2002); Boch, J. Mol. Biol. 312 (3):425-38 (2001); Casas, et al., Plant Breed Rev. 13:235-64 (1995); Newell, Mol. Biotechnol. 16(1):53-65 (2000); Bogorad, Trends Biotechnol. 18(6):257-63 (2000); Komari, et al., Curr. Opin. Plant Biol. 1(2):161-5 (1998); Dempsey, et al., Trends Microbiol. 6(2):54-61 (1998); Oard, Biotechnol. Adv. 9(1):1-11 (1991); and Holm, et al., Transgenic Res. 9(1):21-32 (2000). Specific examples of transformation in potato, rice, corn, barley and wheat are disclosed in Garg, et al., PNAS 99(25):15898-15903 (2002); Cheng, et al., PNAS 95:2767-2772 (1998); Wakita, et al., Genes Genet. Syst. 73:219-226 (1998); Lin, et al., PNAS 100(10):5962-5967 (2003); Breitler, et al., Theor. Appl. Genet. 104(4):709-719 (2002); Miller, et al., Transgenic Res. 11(4):381-96 (2002); Aulinger, et al., Plant Cell Rep. 21(6):585-91 (2003); Romano, et al., Transgenic Res. 12(4):461-73 (2003); de Vetten, et al., Nat. Biotechnol. 21(4):439-42 (2003); Park, et al., Protein Expr. Purif. 25(1):160-5 (2002); Sawahel, Cell Mol. Biol. Lett. 7(1):19-29 (2002); Frame, et al., Plant Physiol. 129:13-22 (2002); Hansen, et al., PNAS 93:14978-14983 (1996); Grosset, et al., Plant Mol. Biol. 34(2):331-8 (1997); Patnaik, et al., BMC Plant Biol. 3:1-11 (2003); Rasco-Gaunt, et al., J. Exp. Botany 52(357):865-874 (2001); Amoah, et al., J. Exp. Botany 52 (358):1135-1142 (2001); and Cheng, et al., Plant Physiol. 115:971-80 (1997).

Representative examples of transgenic plants of the present invention include maize, tomato, turfgrass, asparagus, papaya, sunflower, rye, oats, millet, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax, canola, ornamentals and coffee.

In less preferred embodiments, the L3 polypeptides (with or without a RIP) may be applied directly to a plant or part thereof, in order to achieve increased resistance to fungal diseases.

The L3 N-terminal polypeptides or analogs thereof of the present invention also have pharmaceutical uses. For example, they may be introduced into other eukaryotic cells e.g., human or animal cells, such as by way of administration to an animal or human, to reduce the cytotoxic effect of various pharmaceutical and therapeutic agents that contain ribosome inhibitory proteins (RIP) such as PAP proteins, and particularly wild-type PAP. They are also useful in providing increased resistance to fungal infection, e.g., infections caused or medited by trichothecene mycotoxins, particularly DON and DAS, which are also toxic to human and animal cells. RIPs such as PAP are used to treat viral infections such as HIV (which tends to cause toxicity to host cells), and as targeted cytotoxic agents e.g., to treat cancers (in which case, there is some undesirable non-specific cytotoxicity). In the latter and/or former cases, the RIP may be administered in conjugated form to a ligand that recognizes a receptor on a target cell surface. See, e.g., U.S. Pat. Nos. 5,919,457 and 6,146,628. While not intending to be bound by any particular theory of operation, Applicants believe that the cytotoxic effect of these RIPs such as PAP proteins is mediated by binding to endogenous L3 proteins in the cell. Embodiments of the present invention include co-administration of a composition containing an L3 N-terminal polypeptide or analog thereof along with the RIP, or administration of separate compositions containing the L3 N-terminal polypeptide or analog thereof and the RIP, to an animal (e.g., a mammal such as a human) in need thereof. By co-administration, it is meant administration of the L3 N-terminal polypeptide or analog thereof suitably prior to, simultaneously with or after the administration of the RIP such that the L3 will be present in the cell to reduce to cytotoxic effect of the RIP on various cells, particularly non-diseased cells. The compositions may include a pharmaceutically or veterinary acceptable carrier and at least one other pharmaceutical or veterinary acceptable excipient. Dosage amounts and modes of administration may be determined and optimized based on a consideration of factors such as the weight, age and overall health of the human or animal and severity of the infection, and in accordance with standard procedures in the field.

The L3 N-terminal polypeptides may be produced recombinantly or synthetically, preferably recombinantly, by standard techniques. Aside from production and isolation of the polypeptides from transformed plant hosts (as described above), the polypeptides may be recombinantly produced in bacterial cells, e.g., *E. coli, Streptomyces, Bacillus subtilis*, fungal cells such as yeast, insect cells, and animal cells. As in the case of plants, choice of appropriate vectors, promoters and other 5' and 3' regulatory flanking sequences, e.g., origin of replication, translation initiation and termination, leader sequence, marker genes, methods of introducing the DNAs encoding the polypeptides into the host cell, culturing, isolation and purification techniques, are all well known in the art. Cell-free translation systems may also be employed.

In embodiments of the present invention intended to provide a greater degree of resistance to trichothecene mycotoxins, the human or animal may be administered a composition comprising an effective amount of the L3 N-terminal polypeptide or analog thereof. Here again, dosage amounts and modes of administration may be determined and optimized based on a consideration of factors such as the weight, age and overall health of the human or animal and severity of the infection, and in accordance with standard procedures in the field. This effect may also be achieved by generation of a transformed human or animal (e.g., a non-human animal) containing a nucleic acid encoding L3 N-terminal polypeptide or an analog thereof. The transformed animals are more tolerant to at least the two trichothecene mycotoxins DON and DAS relative to the same species of animal that is not transformed with the nucleic acid. Techniques for generating transgenic animals have been developed and optimized in mice (Hogan et al., 1986, *Manipulation of the mouse embryo: a laboratory manual*. Cold Spring Harbour Laboratory Press: New York), sheep (Wright et al., 1991, Bio-technology NY 9: 831-834), goats (Ebert and Schindler, 1993, Teriogenology, 39: 121-135) and pigs (Rexroad and Purcel, 1988, Proc. 11th Int. Congress of Animal Reproduction and Artificial Insem. 5: 29-35)). In general, such methods are based upon pronuclear micro-injection of fertilized zygotes taken from super-ovulated female animals. Zygote pronuclei are micro-injected with several hundred copies of the novel gene construct, and then transferred to recipient females for the remainder of the gestation period. Confirmation of transgene integration is by Southern hybridization of somatic tissues taken from the offspring, and analysis of gene product or gene function. Suitable animal hosts include any non-human animal that has, at least as a part of its diet, the food grains obtained from plants suspectible to infection by fungi that produce DON and DAS. These animals would include but are not limited to livestock animals, bovines and equines. Examples of specific animals are cows, sheep, goats, pigs, horses, poultry, and rodents such as rats and mice. Methods of introducing transgenes into animal cells and the preparation of transgenic non-human animals are described in section 6.3.17 of U.S. Pat. No. 6,720,014, that specific disclosure of which is hereby incorporated herein by reference.

The present invention is further described in terms of the following non-limiting examples. Unless otherwise indicated, all parts and percentages are on a weight-by-weight basis.

Figure 1:
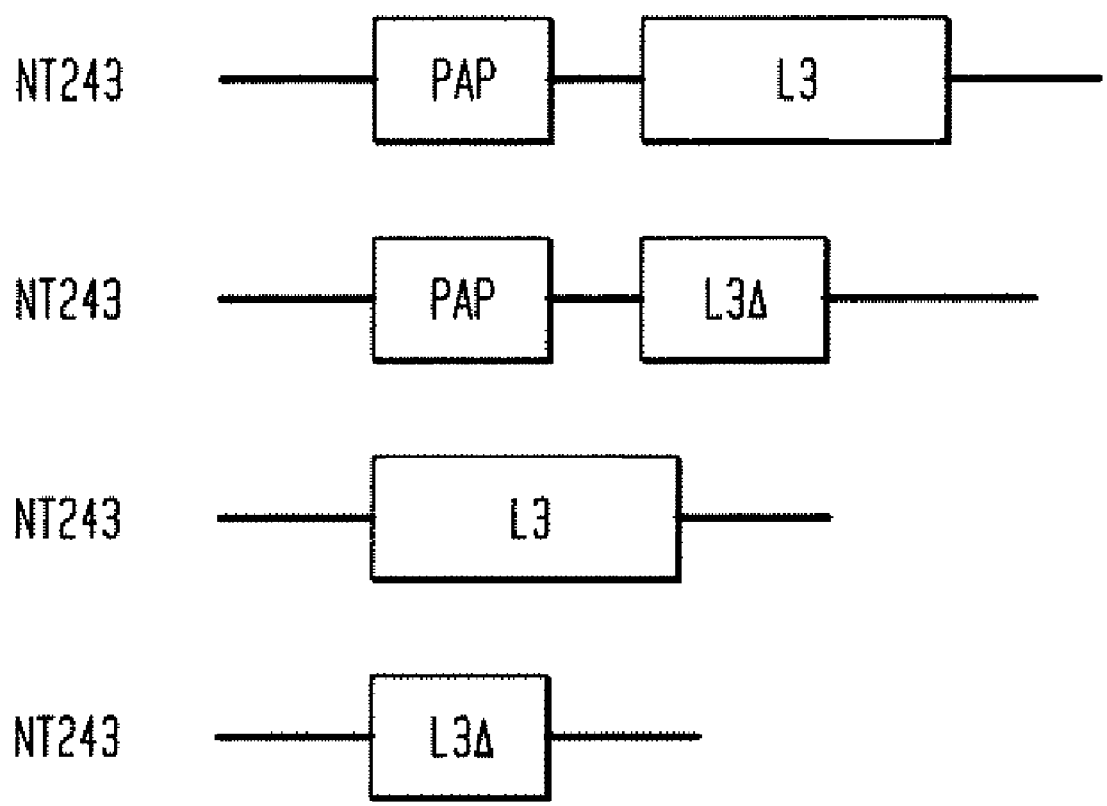
FIG. 1 shows constructs used to generate transgenic tobacco plants described in working examples.
Figure 2A:
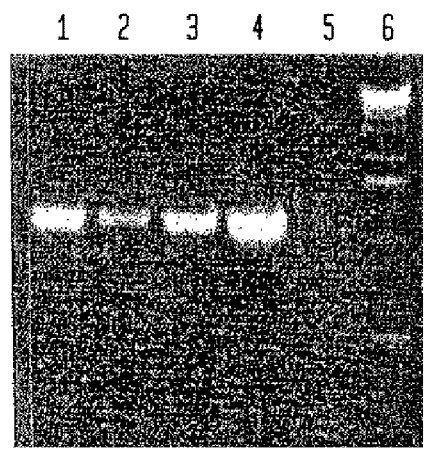
FIGS. 2A, B and C show integration of L3, L3(1-100) and PAP genes in transgenic plants analyzed by PCR or Southern blot. PCR reactions were performed by L3, L3(1-100) and PAP-specific primers. Southern blot was performed on the L3(1-100) PCR products from transgenic plants using $^{32}$P-labeled L3(1-100) fragment as the probe. A. PCR analysis for L3 gene in NT243 and NT250 plants. Lanes 1-2: NT243-6, 8. Lanes 3-4: NT250-1, 4. Lane 5: wt NN. Lane 6: 1 kb MW standard. B. PCR analysis of NT243 and NT245 transgenic tobacco plants for PAP gene. Lane 1: wt NN. Lanes 2-5: NT243-6,7,8,9. Lanes 6-9: NT245-1,2,3,4. Lane 10: wt nn. Lane 11: 1 kb MW standard. C. Southern blot analysis of L3(1-100) PCR products of NT245 and NT252 transgenic plants. Lane 1: L3(1-100) fragment released by restriction enzymes contained in a plasmid. Lane 2-3: NT245-1, 2. Lane 4: wt nn. Lane 5-6: NT252-1, 4.
Figure 2B:
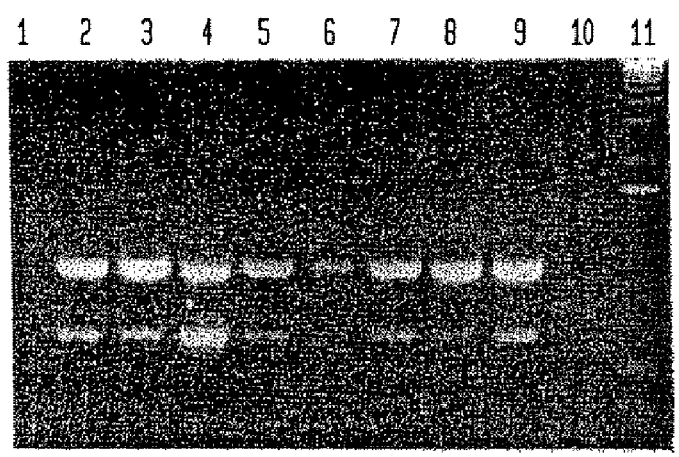
Figure 2C:
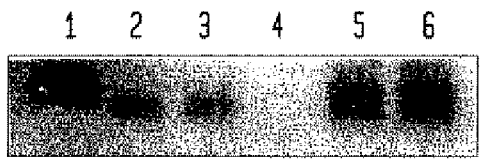

In the first few examples that follow, Applicants have demonstrated, by a sensitive seed germination assay, that overexpression of L3Δ100 in transgenic tobacco plants conferred resistance to the trichothecene fungal toxins DON and DAS, and that in another embodiment of the present invention, namely transgenic tobacco plants transformed with both the yeast L3Δ100 gene and wild type PAP, showed the greatest resistance Results Integration and Expression of L3 and PAP in Transgenic Tobacco Plants Several NPTII positive transgenic tobacco (*N. tabacum* NN) lines, containing NT250 (L3), and NT252 (L3Δ100) were identified by ELISA for the NPTII gene expression. The integration of L3 was confirmed by PCR (FIG. 2 A.). The integration of L3Δ100 was confirmed by Southern blotting of the PCR products with L3Δ100-specific primers (FIG. 2 C.). All of these transgenic plants were phenotypically normal and indistinguishable from wild type plants based on their appearance and growth characteristics. However, immunoblot analysis with yeast L3 specific monoclonal antibody revealed undetectable levels of L3 and L3Δ100 genes.

Figure 3A:
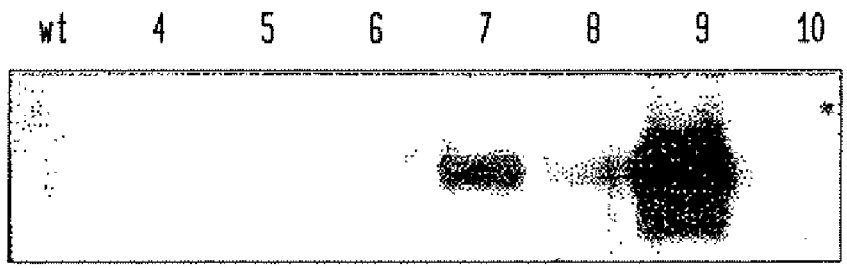
FIGS. 3A, B and C show Western blot analysis on PAP expression level in transgenic tobacco plants. 10 µg of protein for each sample was electrophoresed on 10% SDS-PAGE. Proteins were transferred to nitrocellulose membrane and probed with PAP-specific polyclonal antibody. A. NT243 R0 transgenic plants. B. NT243 R2 transgenic plants. C. NT245 R0 transgenic plants.
Figure 3B:
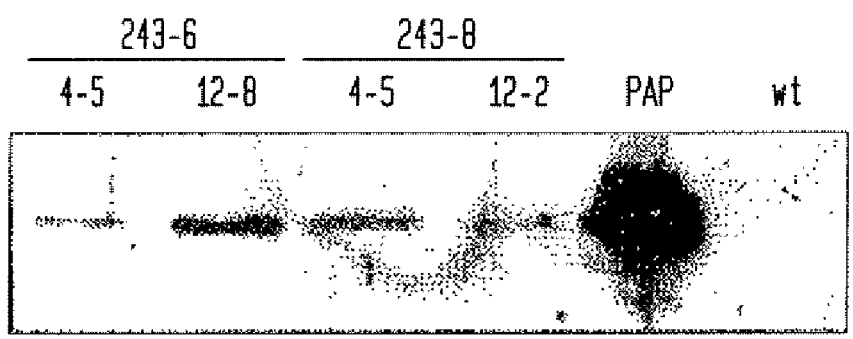
Figure 3C:
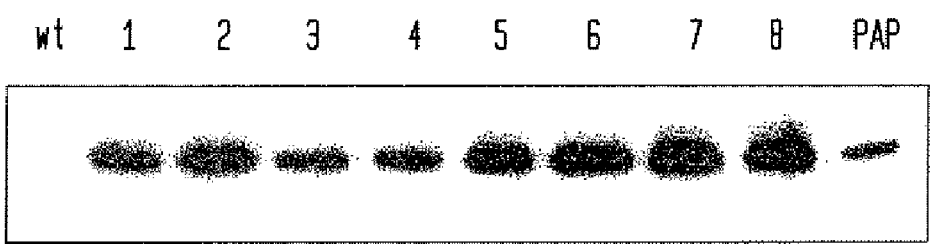

A total of 12 transgenic tobacco plants (*N. tabacum* NN) transformed with both wild type (wt) L3 and wt PAP (NT243) were identified by ELISA for NPTII. The transformation frequency, defined as the number of transgenic plants obtained per initial leaf disk times 100, was approximately 24%. The presence of both L3 and PAP genes were confirmed by PCR analysis (FIGS. 2 A. and B.). However, immunoblot assay using monoclonal antibodies against yeast L3 did not detect expression of the yeast L3 in transgenic tobacco plants. The immunoblot analysis of the primary (R0) transgenic plants containing NT243 showed varied levels of PAP expression, with NT243-7 and NT243-9 as the highest expressers (FIG. 3 A.). Only these two plants showed mottled symptoms on their leaves similar to transgenic plants expressing the toxic variant form of PAP (PAPv, 26139-19) (Lodge et al., Proc. Natl. Acad. Sci. USA 90:7089-7093 (1993)). NT243-7 and NT243-9, however, did not produce any viable seeds. The other plants appeared normal compared to untransformed plants. The PAP expression level in NT243-6 and NT243-8 plants was much lower compared to NT243-7 and NT243-9. None of the other transgenic plants tested showed detectable PAP expression. Immunoblot analysis performed on R2 generation plants from NT243-6 and NT243-8 demonstrated a considerable amount of PAP expression (FIG. 3 B.), yet these plants appeared normal.

Several transgenic tobacco plants (*N. tabacum* nn) were generated with NT245, which contained both L31Δ100 and PAP genes. These plants were all phenotypically indistinguishable from the wild type plants. PCR and Southern blot analysis confirmed the presence of both genes in the transgenic plants (FIGS. 2 B. and C.). While Western blot analysis did not reveal detectable levels of L3Δ100, PAP was expressed at high levels in all the plants tested, in contrast to the PAP expression in NT243 plants (FIG. 3 C.).

Depurination Assay

Figure 4:
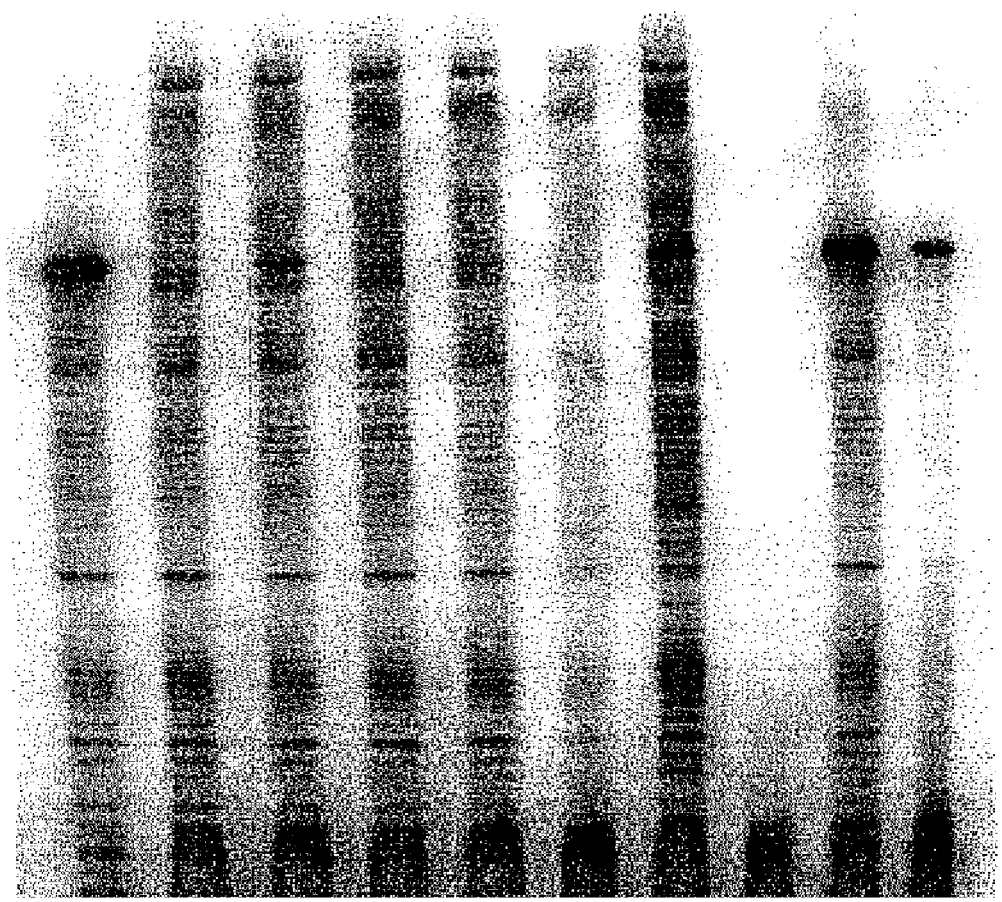
FIG. 4 shows results of a depurination assay by primer extension of NT243 and NT245 R2 transgenic plants. Ribosomal RNAs were isolated as described and incubated with $^{32}$P end-labeled oligonucleotide complementary to the 3'-end of the plant large rRNA. Primer extension was performed by reverse transcriptase. Lane1: wt rRNA treated with PAP as in vitro positive control. Lane2: wt rRNA not treated as in vitro negative control. Lane3: PAPv (less toxic PAP variant) rRNA as in vivo positive control. Lane4: PAPx (active site mutant) rRNA as in vivo negative control. Lane5: NT245-12. Lane6: NT245-21. Lane7: NT243-64. Lane8: no rRNA plus probe control. Lane9: NT245-12 treated with PAP. Lane10: NT245-21 treated with PAP.

Ribosomal RNA depurination assay by primer extension clearly showed that the rRNAs from the R2 plants of NT243 (L3+PAP) were depurinated by the constitutively expressed wild type PAP (FIG. 4, lane 7, NT243-64). However, depurination by wt PAP in these plants did not seem to affect the morphology of the plants or the viability of the seeds. PAP was expressed at very high levels in NT243-7 and NT243-9, which showed mosaic symptoms and did not produce seeds. The symptoms observed on these plants and their inability to produce seed may have been due to the higher level of depurination in these two plants. In contrast to the NT243 lines, rRNA in the R2 plants of NT245 (L3Δ100+PAP) was not depurinated (FIG. 4, lanes 5 and 6). However, when the ribosomes of NT245 R2 plants were isolated and treated with purified PAP in vitro (Hudak et al., J. Biol. Chem. 274:3859-3864 (1999)), the rRNAs were depurinated. These results indicated that the S/R loop was not resistant to depurination by PAP in NT245 lines. While not intending to be bound by any particular theory of operation, Applicants believe that the yeast L3Δ100 gene interacts with PAP, rendering it inactive in terms of depurination, resulting in healthy plants.

Fungal Toxin Resistance Assay

Figure 5A:
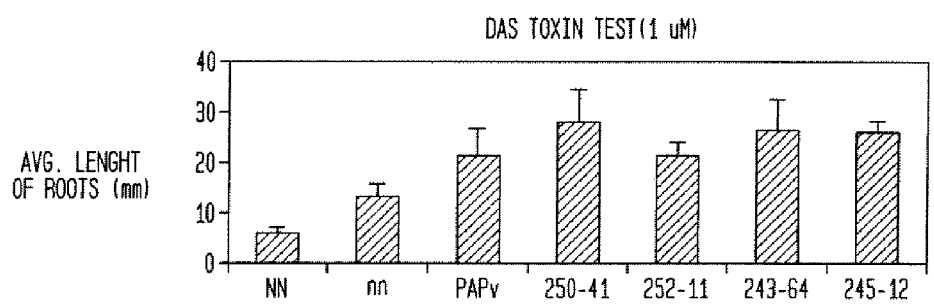
FIGS. 5A and B show results of a DAS fungal toxin resistance test. Tobacco seeds were surface sterilized and germinated on MS medium containing 1 μM of DAS. The root length of 10 plants for each transgenic line was measured and averaged six weeks after as graphed in A. Pictures of the root growth of the wild type tobacco and transgenic plants are shown in B.
Figure 5B:
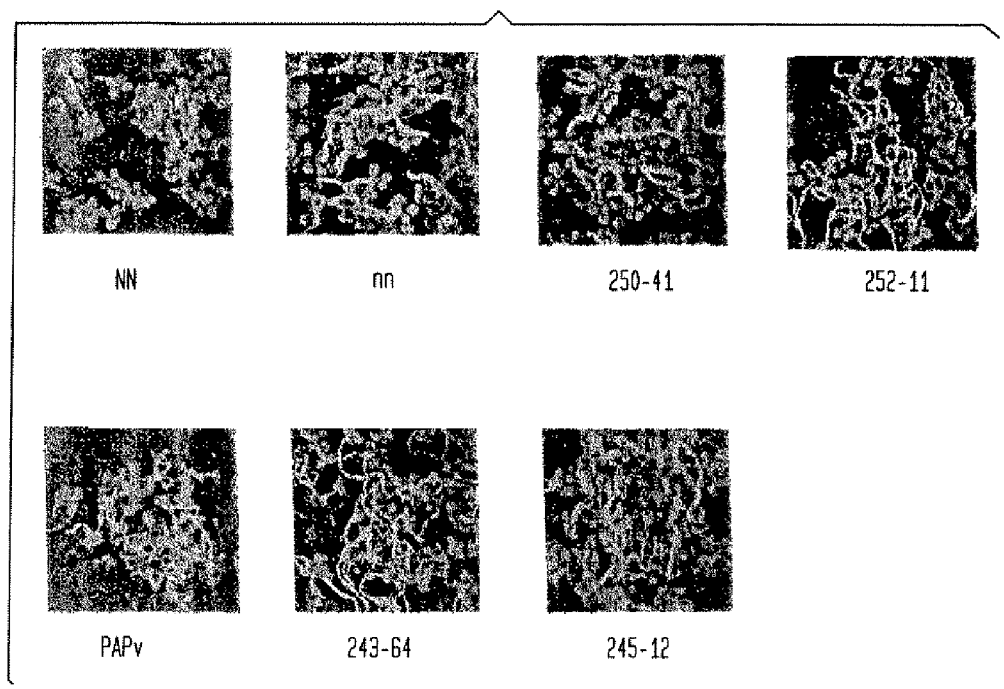

With the sensitive seed germination assay, the optimum concentrations of DON and DAS were determined by plating wild type tobacco seeds on the MS medium containing different concentrations of DON or DAS. Based on this analysis, 1 μM of DAS and 10 μM of DON were selected as the lowest concentrations that would give the best inhibition of wild type tobacco seed growth. Muhitch et al., Plant Science 157:201-207 (2000) have shown that DON is far more inhibitory than DAS toward wheat. When transgenic tobacco seeds were plated on the MS medium containing 1 μM of DAS, NT250 plants transformed with only yeast L3 were highly resistant to this trichothecene fungal toxin (FIG. 5). The resistance level as measured by the average root length of 10 plants, was almost as high as 4-fold compared to wild type tobacco plants. NT243 plants transformed with both L3 and PAP were equally resistant to DAS as NT245 (L3Δ100+PAP) plants, while transgenic tobacco plants expressing PAPv (Lodge et al., Proc. Natl. Acad. Sci. USA 90:7089-7093 (1993) and NT252 expressing L3Δ100 alone were also resistant to DAS but at a relatively lower level.

Figure 6A:
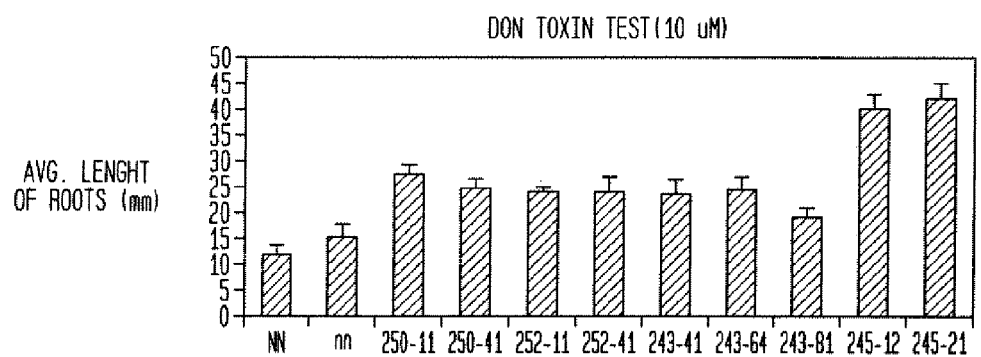
FIGS. 6A and B show results of a DON fungal toxin resistance test. Tobacco seeds were surface sterilized and germinated on MS medium containing 10 μM of DON. The root length of 10 plants from each construct was measured and averaged six weeks after as graphed in A. Pictures of the root growth of the wild type tobacco and transgenic plants are shown in B.
Figure 6B:
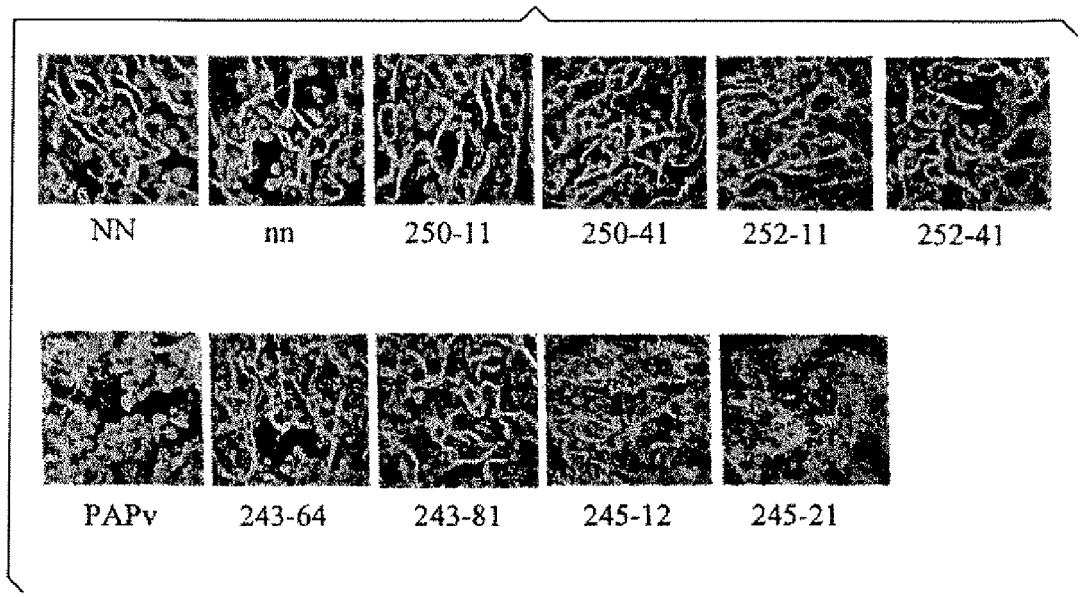

When transgenic tobacco seeds were plated on the MS medium containing 10 μM of DON, all transgenic plants including PAPv, NT250 (L3), NT252 (L3Δ100), NT243 (L3+PAP) and NT245 (L3Δ100+PAP) exhibited resistance to DON compared to wild type plants (FIG. 6). L3Δ100 plus PAP plants (NT245) showed the greatest resistance to DON, almost as high as 4-fold compared to wild type tobacco plants.

These data showed that yeast L3 or L3Δ100 alone in transgenic tobacco plants conferred considerable resistance to trichothecene *Fusarium* toxins DAS and DON. The combination of L31100 with PAP conferred better resistance to DON than either gene alone.

Virus Resistance Assay

Figure 7:
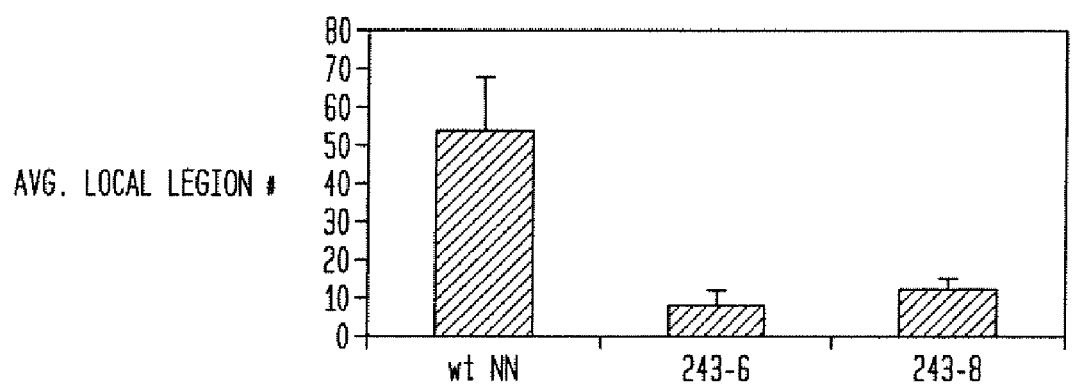
FIG. 7 shows results of a virus resistance test on the R1 transgenic plants of NT243. Two leaves of each plant were inoculated with TMV of 2 μg/ml. The local lesion numbers on the upper leaves of ten plants were counted and averaged and compared to the wild type plants.

Five days after inoculation with TMV, the local lesion numbers on the leaves of NT250 (L3), and NT252 (L3Δ100) transgenic plants were similar to the untransformed plants (data not shown) indicating that L3 and L3Δ100 genes alone in transgenic plants did not confer resistance to plant virus. However, FIG. 7 shows that the local lesion numbers of TMV on the R1 plants of NT243 (L3+PAP)-6 and NT243-8 were significantly lower compared to the wild type tobacco. This indicates that the interaction between L3 and PAP significantly reduced the toxicity of PAP in NT243 plants, yet retained the antiviral characteristic of PAP.

ELISA results (data not shown) showed that NT245 (L3Δ100+PAP) R2 plants inoculated with PVY contained almost same amount of virus as the inoculated wild type plants. This seems to suggest that the interaction between the 99 amino acids at N-terminus of yeast L3 and PAP completely abolished the toxicity of PAP as shown by all normal-looking transgenic plants, but did not retain the antiviral activity of PAP as in NT243 (L3+PAP) plants.

Expression of Pr Proteins in Transgenic NT243 (L3+PAP) Plants

Figure 8:
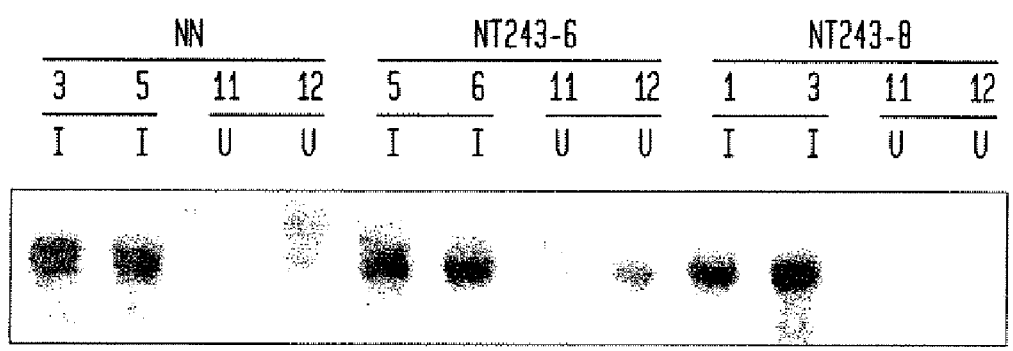
FIG. 8 shows a Northern blot analysis to detect tobacco basic chitinase in R1 plants of NT243 inoculated with TMV (I) or with H$_2$O (U). Total RNA was isolated and electrophoresed in denaturing agarose gel and transferred onto Duralose UV-membrane (Stratagene). The membrane was hybridized with $^{32}$P-labeled basic chitinase cDNA.

Northern blot analysis (FIG. 8) revealed that prior to inoculation of TMV, the R1 plants of NT243-6 and NT243-8 did not show any accumulation of tobacco basic chitinase. The basic chitinase level in these transgenic plants was detectable only after they were inoculated with TMV, same as wild type plants. This is contrary to a previous finding in that the expression of PAPv (26139-19 line) constitutively induced the expression of the basic isoform of tobacco PR proteins (Zoubenko et al., Nature Biotechnol. 15:992-996 (1997)). Again, without intending to be bound by theory, this result suggests that the interaction between L3 and PAP seemed to have disrupted the induced disease resistance pathway as in PAPv (26139-19) transgenic plants, and that the viral resistance of NT243 plants may have come from the direct depurination of infecting viruses.

Expression of Tobacco L3A and L3B by Real-Time PCR

The gene expression level of tubulin was assessed and appeared to be relatively constant in all the plants (data not shown). Therefore it was used as an internal control for the calculation of the "fold expression" of transgenic plants compared to wild type tobacco. The real-time quantitative PCR results (FIGS. 9 A. and B.) showed that the gene expression levels of L3A and L3B were enhanced in all the transgenic plants including PAPv, NT250 (L3), NT252 (L3Δ100), NT243 (L3+PAP) and NT245 (L3Δ100+PAP) compared to wt plants. PAPv plants displayed the highest level of gene expression in both L3A and L3B. The NT252 lines showed relatively higher elevation of both L3A and L3B gene expression compared to the rest of the transgenic lines. Western blot result of the cytosolic samples with tobacco L3 polyclonal antibody (FIG. 9 C.) confirmed the real-time PCR data. These seemed to correlate slightly with the resistance level of these transgenic plants to fungal toxins. As in FIG. 6, PAPv demonstrated higher resistance to DON compared to the other transgenic lines and wild type plants, except NT245 lines. These results suggested that the elevated levels of L3A and L3B in transgenic tobacco plants might provide excessive targets for the fungal toxins, resulting in the resistance to DON and DAS tested.

Discussion

The observation that 12 transgenic NT243 (L3+PAP) tobacco plants were regenerated with a transformation frequency of 24% and the majority of plants appeared normal indicated an amazing difference from previously reported data in which the transformation frequency with wild type PAP (pMON8443) was only 0.7% (Lodge et al., Proc. Natl. Acad. Sci. USA 90:7089-7093 (1993)). This clearly demonstrated that the interaction between L3 and PAP existed at the transgene level in transgenic tobacco plants. In addition, this interaction was exhibited not only between the wild type L3 gene, but also between the truncated L3 with the N-terminal 100 amino acids, because all the transgenic plants containing NT245 (L3Δ100+PAP) appeared indistinguishable from the non-transgenic plants.

The gene expression level of both L3 and L3Δ100 was undetectable at the protein level in transgenic plants expressing L3 alone or together with PAP (NT243/L3+PAP, NT245/L3Δ100+PAP, NT250/L3 and NT252/L3Δ100). However, the expression level of either L3 or L3Δ100 could be detected by real-time PCR (FIG. 10 A.). L3Δ100 in NT252 plants showed more than 1000-fold higher level of gene expression relative to the wild type plant. L3 expression levels in NT250 were 100- to 200-fold higher relative to that in wild type plant. Comparatively, the gene expression of L3 and L3Δ100 in NT243 (L3+PAP) and NT245 (L3Δ100+PAP) was much lower, from 25- to 38-fold. The expression level of PAP in NT243 (L3+PAP) coincided with the severity of the mottling symptoms just as PAPv (26139-19) plants, resulting in sterility of the highest expressers (NT243-7 and NT243-9). Depurination assay showed that the low level expression of PAP in NT243-6 and NT243-8 plants still resulted in the disruption of some tobacco ribosomes, but it did not seem to have much effect on the growth of these plants and the production of their seeds. The PAP expression level in NT245 (L3Δ100+PAP) plants, however, was very high in every plant. The PAP gene expression level in NT245-12 was even higher than PAPx, the non-depurinating active site mutant. And all NT245 plants were normal looking and fertile. Depurination assay indicated that the rRNAs of NT245 plants were not depurinated (FIG. 4). It demonstrated that the full-length yeast L3 in NT243 plants at undetectable protein level greatly reduced the toxicity of PAP, while L3Δ100 in NT245 also at undetectable protein level completely abolished the toxicity of PAP. This seemed to indicate the difference between the interaction of L3 and L3Δ100 with PAP and show that L3Δ100 works better than the full length L3 gene. In addition, the effect of L3 and L3Δ100 on PAP seems to be at the transcription level for the L3 and L3Δ100 genes verses the translation level for PAP. L3Δ100 comprises of the first 100 amino acids of yeast ribosomal protein L3. It has been shown to exert a trans-dominant effect on promoting the programmed −1 ribosomal frameshifting of the L-A double-stranded RNA virus and reducing the translation fidelity in yeast (Peltz et al., Mol. Cell. Biol. 19(1):384-91 (1999)). A previous study in yeast showed that wild type L3 is required for PAP to bind to ribosomes and depurinate the 25S rRNA (Hudak et al., J. Biol. Chem. 274: 3859-3864 (1999)). By studying PAP mutants, domains of PAP that are involved in toxicity to yeast cells have been identified. These domains can be separated from the depurination property of PAP (manuscript submitted). Again, without intending to be bound by theory, Applicants believe that L3 counter-interacts with the toxicity domains of PAP, and this counter-interaction is more specific for L3Δ100 than for L3.

The interaction between L3 and PAP in NT243 also disrupted the induction of one of the tobacco PR proteins, basic chitinase, as was previously observed in PAPv (26139-19) plants (Zoubenko et al., Nature Biotechnol. 15:992-996 (1997)). Therefore, the resistance to TMV of these plants might have resulted from the direct depurination or inhibition of infecting virus by the low level of PAP. The interaction between L3Δ100 and PAP in NT245 resulted in non-depurinating PAP and susceptibility of plants to PVY, although the PAP expression level was very high in these plants as demonstrated by Western blot of the cytosolic extracts (FIG. 3 C.), real-time PCR analysis (FIG. 10 B.) and Western blot on the ribosomal samples (FIG. 10 C.).

The results have shown that all transgenic tobacco plants were resistant to trichothecene fungal toxins DAS and DON, with NT245 (L3Δ100+PAP) as the most resistant lines to DON. To investigate the mechanism of fungal toxin resistance in the transgenic plants, the levels of tobacco ribosomal proteins L3A and L3B, which are the targets for fungal toxins, were analyzed by real-time PCR (FIGS. 9 A. and B.). The levels of L3A and L3B in transgenic tobacco plants expressing PAPv were both elevated by 2- to 3-fold compared to wild type plants. The L3A and L3B in NT250 (L3), NT252 (L3Δ100) and NT245 (L3Δ100+PAP) were elevated at much lesser levels, ranging from 0.5- to 2-fold. Again, without intending to be bound by theory, Applicants postulate that the fungal toxin resistance in 26139-19, NT250, NT252, and NT245 may have resulted from the elevated levels of L3A and L3B, which provided excessive targets for toxins and henceforth overcame the toxic effects. The levels of L3A and L3B might have been elevated by wild type L3, L3Δ100 and PAPv genes. This elevation might have been at the post-transcriptional level because these three genes were hardly detectable at the protein level in NT250 (L3), NT252 (L3Δ100), NT243 (L3+PAP), NT245 (L3Δ100+PAP) and PAPv plants. In addition, NT245 plants demonstrated the highest fungal toxin resistance although the L3A and L3B levels were not as high as they were in PAPv or in NT252-11 (FIGS. 9 A. and B.).

Again, without intending to be bound by theory, Applicants hypothesize that in these plants, both yeast L3Δ100 and wt PAP bound to the tobacco ribosomes in a way that the ribosomes were shielded from the fungal toxins.

This study has shown that NT243 expressing both low levels of wild type yeast L3 and wild type PAP conferred resistance to fungal toxins DAS and DON and TMV. NT245 expressing yeast L3Δ100 and PAP, NT250 expressing L3 and NT252 expressing L3Δ100 provided great resistance to fungal toxins. The results of this study demonstrate that by altering ribosomal protein L3, the target of fungal toxins and combining it with PAP, relatively high levels of resistance to trichothecene mycotoxins was obtained.

Interaction of Yeast L3 with Pokeweed Antiviral Protein (PAP) in Yeast Cells

Expression of the Yeast L3Δ100 and L3Δ99 Reduces the Cytotoxicity of Pap in Yeast In the following examples, we show here that co-expression of a truncated form of yeast L3 (L3Δ100) which encodes the first 100 amino acids of L3 with wild type PAP in transgenic tobacco plants eliminates the autoregulation of PAP expression, ribosome depurination and cytotoxicity of PAP. Expression of the endogenous tobacco ribosomal protein L3 is upregulated in the transgenic lines and they are resistant to the *Fusarium* mycotoxins, DON and DAS. The L3Δ100 is much more effective in conferring resistance to PAP and the trichothecene mycotoxins than the full length L3 gene because expression of the full length L3 gene from yeast in transgenic tobacco plants does not completely eliminate the autoregulation of PAP expression, ribosome depurination and the cytotoxicity of PAP, but reduces it. Although L3Δ100 expressed in plants does not contain the tcm-1 mutation (W255C) or the (P257T) mutation found in mak8-1, which protect ribosomes from depurination by PAP, it is highly effective in preventing ribosome depurination, mRNA autoregulation and cytotoxicity of PAP. Co-expression of the first 99 amino acids of L3 with wild type PAP in yeast eliminates the autoregulation of PAP expression, ribosome depurination and cytotoxicity of PAP.

We also show that L3Δ99, that includes the first 99 amino acids of L3, works better in yeast than the L3Δ100. These results demonstrate that expression of an N-terminal fragment of L3 leads to high level of resistance to PAP and DON, providing evidence that both toxins target L3 by a common mechanism.

The polynucleotides encoding that first 100 or 99 amino acids at the N-terminus of yeast L3 gene were cloned in the yeast expression vector pAC55 under GAL1 promoter on a URA3 plasmid, resulting in NT760 (L3Δ100) and NT771 (L3Δ99), respectively. Both NT760 and NT771 were co-transformed into yeast cells together with NT188 containing the wild type PAP gene in a yeast expression vector under the GAL1 promoter with LEU2 marker. Transformants were selected on SD-leu-ura media. The presence of both L3Δ genes and PAP gene in each transformant was confirmed by isolating the plasmids from yeast cells and re-transforming into *E. coli* cells.

Figure 20:
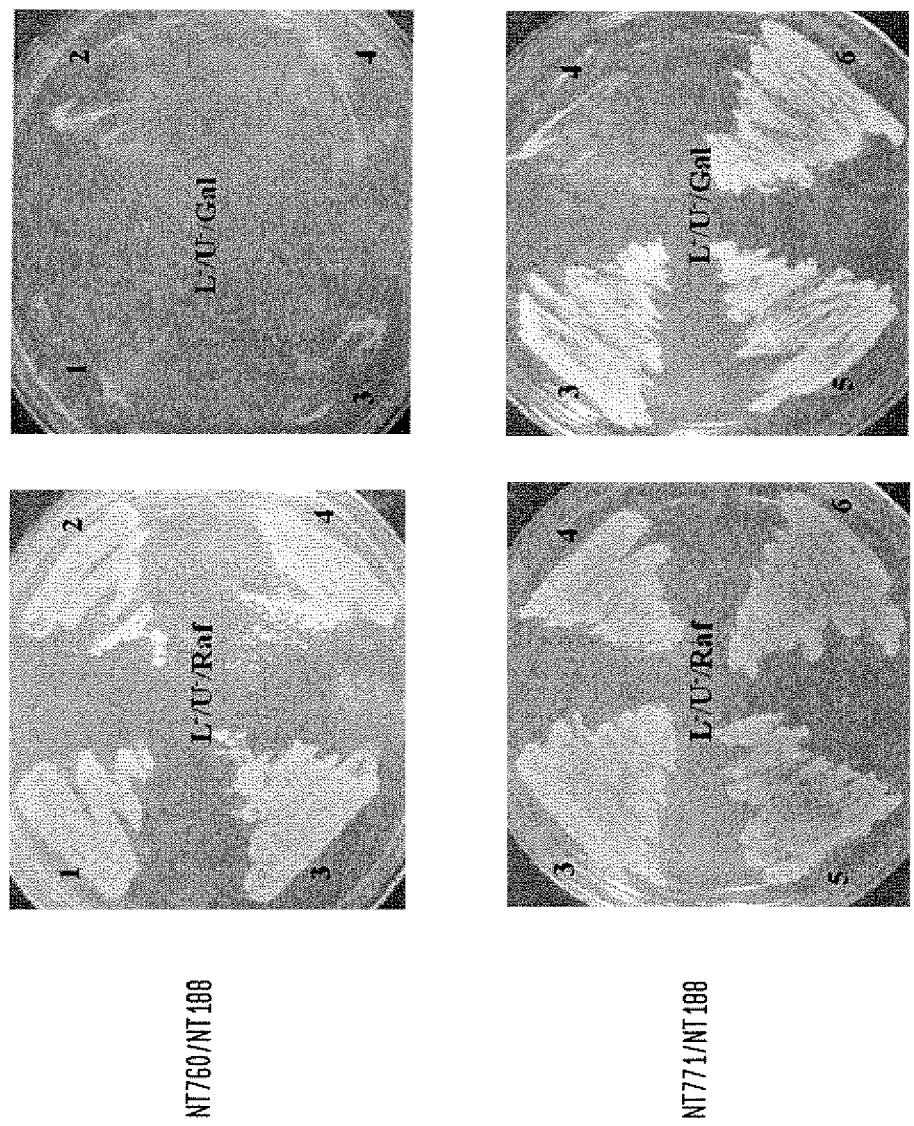
FIGS. 20 and 21 show results of cytotoxicity experiments conducted in yeast transformed with PAP and L3(1-99) or L3(1-100).
Figure 21:
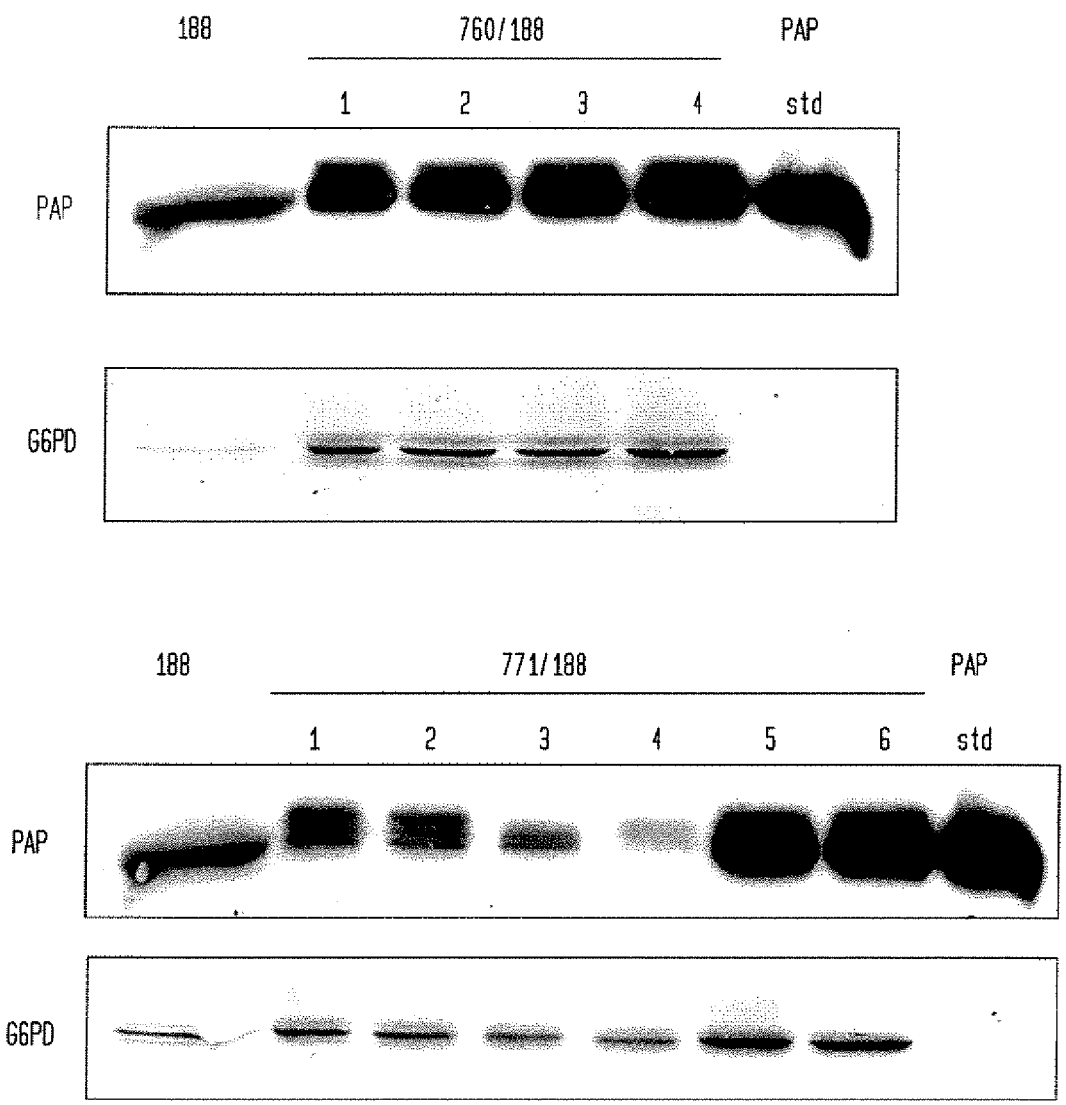

The cytotoxicity of PAP in yeast containing NT760 and NT188 was not affected since they did not grow on plates containing galactose (FIG. 20). However, the cytotoxicity of PAP in yeast containing NT771 and NT188 was abolished in three out of four transformants (FIG. 20). Immunoblot analysis showed that there was an equivalent amount of PAP produced in cells containing NT760 and NT188 cells as the cells containing NT188 alone (FIG. 21). In contrast, there was significantly more PAP protein produced in cells containing NT771 and NT188 (transformants 5 and 6) (FIG. 21). These results indicated that L3Δ99 could reduce the toxicity of PAP much better than L3Δ100 in yeast.

Figure 22A:
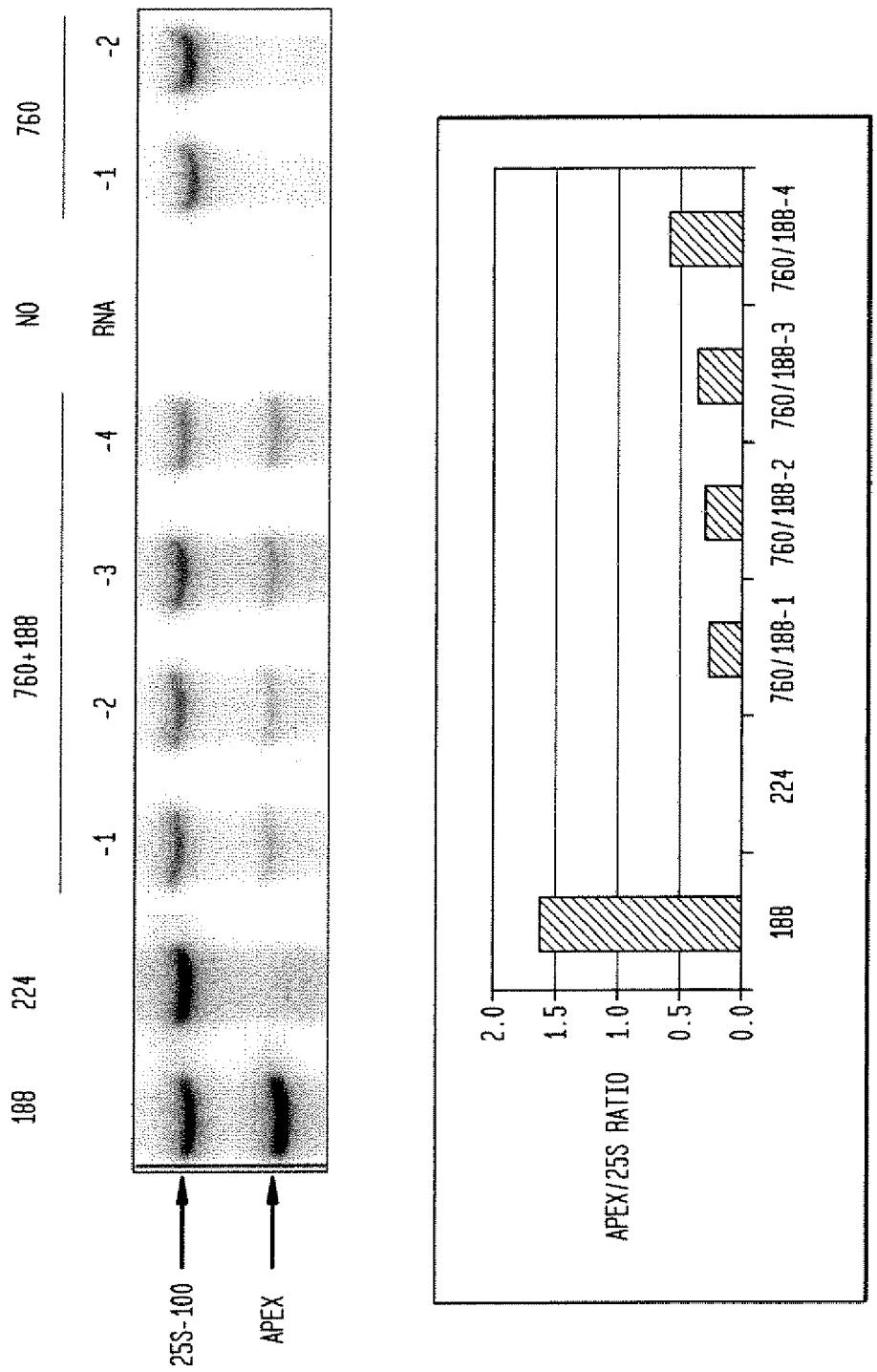
FIGS. 22A and B show results of ribosome depurination experiments conducted in yeast transformed with PAP and L3(1-99) or L3(1-100).

To assess the level of rRNA depurination by PAP in yeast cells, total RNAs from cells containing NT760/NT188 and NT771/NT188 were extracted and subjected to the dual-primer extension analysis. As shown in FIG. 22A, ribosome depurination was reduced by approximately 80% in cells containing NT760 and NT188 compared to cells containing NT188 alone. As shown in FIG. 22B, the depurination of rRNA was greatly reduced (transformants 3 and 4) or eliminated (transformants 5 and 6) in cells containing NT771 and NT188. These results showed that co-expression of L3Δ99 with PAP eliminated the cytotoxicity of PAP.

Figure 23:
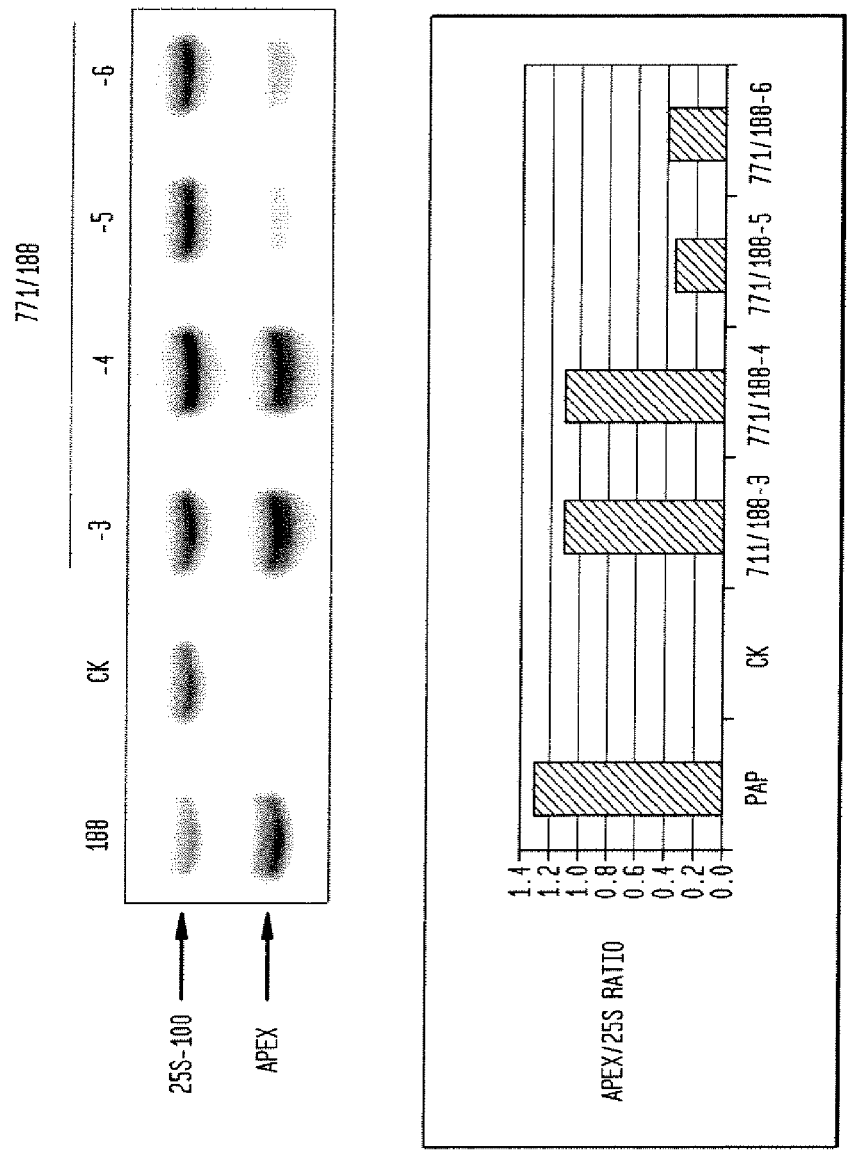
FIG. 23 shows results of a ribosome depurination assay conducted in vitro.

Since there was a large amount of PAP produced in the non-toxic NT771/NT188 transformants 5 and 6, compared to the transformants 3 and 4 (FIG. 21), PAP was extracted from each transformant using SuperFine Sephadex G25 columns. The PAP proteins were then used in an in vitro depurination assay by incubating PAP with ribosomes from the wild type cells. The rRNAs were then extracted and ribosome depurination was analyzed by the dual-primer extension assay. As shown in FIG. 23, PAP protein extracted from transformants 3 and 4 could still depurinate ribosomes in vitro. In contrast, PAP protein isolated from transformants 5 and 6 could not depurinate the ribosomes in vitro.

Yeast L3Δ99 Abolishes the Autoregulation of PAP Gene Expression and Enhances the Stability of PAP mRNA.

Figure 24:
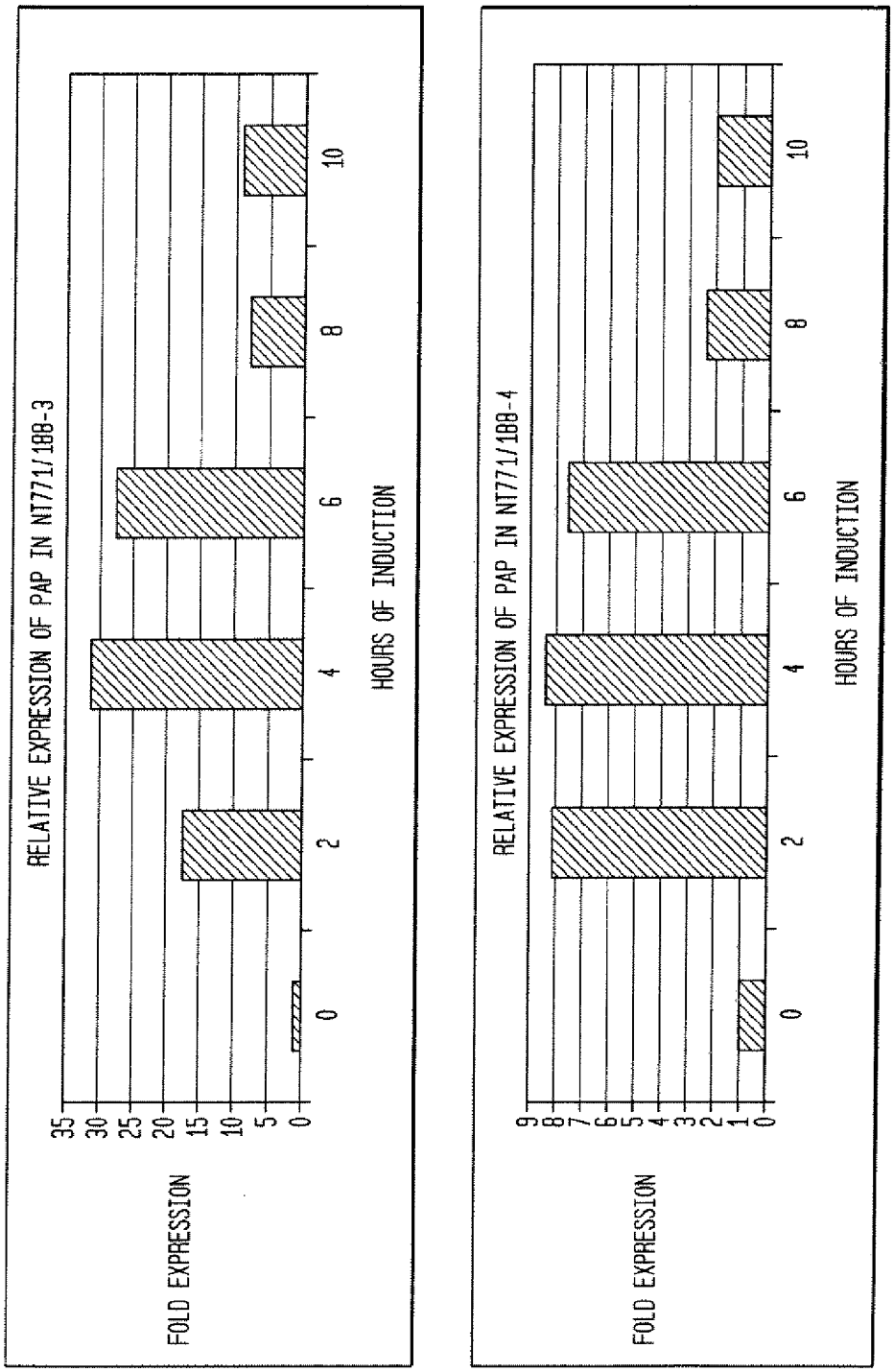
FIG. 24 shows results of a real time PCR analysis of production of PAP mRNA in yeast cells transformed with L3 N-terminal polypeptides of the present invention.
Figure 24:
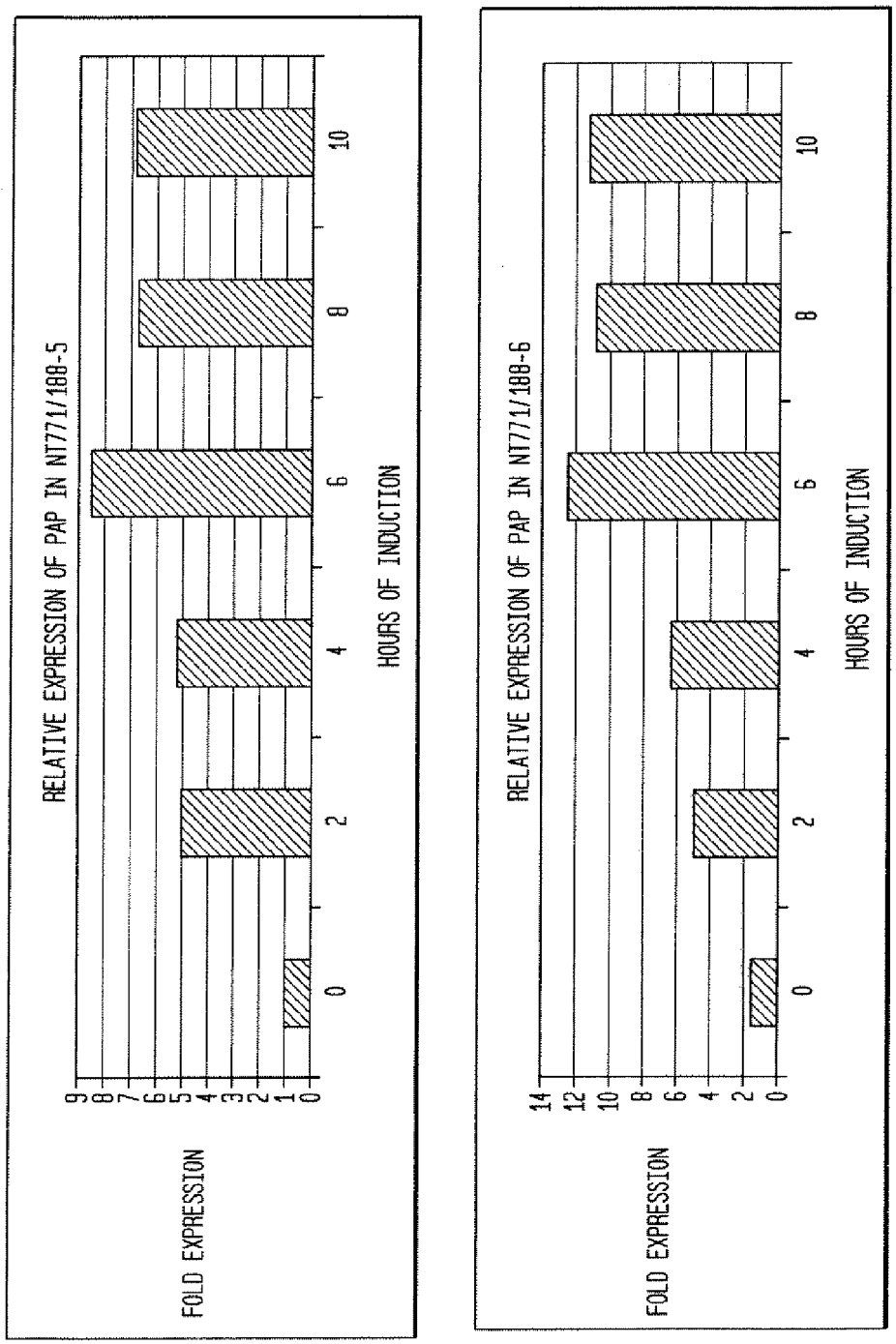

To determine if PAP destabilizes its own mRNA in cells containing NT771 and NT188, we used real-time PCR analysis with ABI PRISM 7000 Sequence Detection System (Applied Biosystems) to examine the mRNA levels in transformants 3, 4, 5 and 6 after induction on galactose for six hours. Reverse transcription reaction was carried out using the total yeast RNAs as templates and oligo d(T) as the primer. The single stranded cDNAs produced were used in real-time PCR analysis using two PAP-specific primers (PAP690F, 5'-GGG-TAAGATTTCAACAGCAATTCA-3' (SEQ ID NO: 39) and PAP769R, 5'-CACCACTGGCATCCACTAGCT-3'; SEQ ID NO: 40). The PAP gene expression level was normalized against the yeast G6PD mRNA as an internal control using the ddCT method. It is shown in FIG. 24 that PAP mRNA in transformants 3 and 4 accumulated to the highest level at 4 hr after induction and then gradually declined. This PAP gene expression pattern was exactly the same as in yeast expressing NT188, which destabilizes its own mRNA. In contrast, the PAP mRNA level in transformants 5 and 6 increased up to six hours and did not decrease after 6 hours of galactose induction. This expression pattern was similar to what was observed with the active site mutant NT224 (PAPx) which does not autoregulate its own mRNA, i.e., the stability of PAPx mRNA is not affected. These results indicate that L3Δ99 diminishes the effect of PAP on its own mRNA, resulting in stabilization of PAP mRNA.

Effect of the First 21 Amino Acids of L3.

Figure 26:
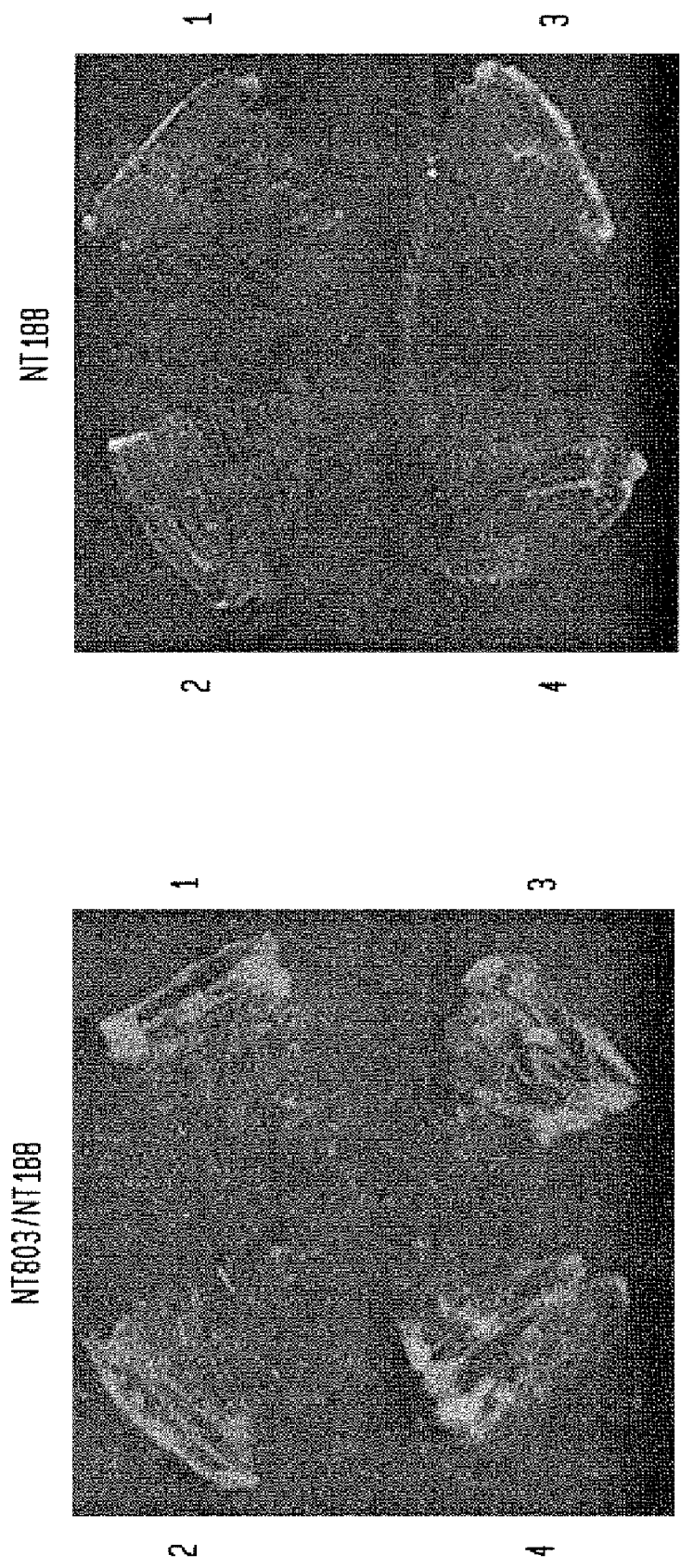
FIG. 26 shows results of a growth assay of yeast cells transformed with PAP and a polynucleotide encoding L3 polypeptides of the present invention.

The 5' end of L3 mRNA contains a stem loop structure highly similar to the SRL of rRNA (FIG. 25). The sequence "14AGUACGA20" in the L3 mRNA stem loop is identical to the sequence of the sarcin ricin loop (SRL) "AGUAC-GAGAGGA" (SEQ ID NO: 41), which is the longest conserved sequence found in all large rRNAs. Since PAP binds to the SRL, this sequence in L3 may act as an SRL mimic and PAP may bind to it and destabilize the L3Δ mRNA instead of its own mRNA. To test this, a polynucleotide encoding the first 21 amino acids of yeast L3 was cloned into pTKB175 under the GAL1 promoter (NT803). NT803 was co-transformed into yeast cells with NT188. As shown in FIG. 26, all four transformants containing NT803 and NT188 grew better on galactose. This indicates that the first 21 amino acids may have similar effect on PAP's toxicity as L3Δ99.

All publications cited in the specification, both patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A transgenic plant comprising an exogenous nucleic acid comprising a transgene functional therein and that encodes an N-terminal polypeptide fragment of an eucaryotic ribosomal L3 protein, wherein said fragment contains at least the first 21 to about 99 N-terminal amino acid residues of a full-length eucaryotic L3 protein, wherein said plant does not contain a transgene encoding a ribosome inactivating protein (RIP) that targets an L3 eucaryotic protein, and wherein said plant exhibits increased resistance to fungal toxins that target the eucaryotic ribosomal L3 protein compared to a non-transgenic control plant.

2. The transgenic plant of claim 1, wherein the transgene encodes an N-terminal polypeptide fragment of L3 having from the first 21 to 99 N-terminal amino acid residues of the full-length ribosomal L3 protein.

3. The transgenic plant of claim 1, wherein the transgene encodes an N-terminal polypeptide fragment of L3 having amino acids 1-99 of the eucaryotic ribosomal L3 protein.

4. The transgenic plant of claim 1, wherein the transgene encodes an N-terminal polypeptide fragment of L3 having amino acids 1-100 of the eucaryotic ribosomal L3 protein.

5. The transgenic plant of claim 1, wherein the transgene encodes an N-terminal polypeptide fragment of L3 having amino acids 1-21 of the eucaryotic ribosomal L3 protein.

6. The transgenic plant of claim 1, which is a monocot plant.

7. The transgenic plant of claim 1, which is a cereal crop plant.

8. The transgenic plant of claim 7, wherein the cereal crop plant is maize, rice, wheat, oat, barley or wheat.

9. The transgenic plant of claim 1, which is a dicot plant.

10. A transgenic seed derived from the transgenic plant of claim 1.

11. A method of making a transgenic plant having increased resistance to infestation by fungi that produce toxins that target a eucaryotic L3 protein, comprising preparing a transgenic plant having a genome that contains an exogenous nucleic acid comprising a transgene encoding an N-terminal polypeptide fragment of an eucaryotic ribosomal L3 protein, wherein said fragment contains at least the first 21 to about 99 N-terminal amino acid residues of a full-length eucaryotic L3 protein, wherein said plant does not contain a transgene encoding a ribosome inactivating protein (RIP) that targets an L3 eucaryotic protein, and wherein expression of the transgene in the transgenic plant confers increased resistance to fungal toxins that target the eucaryotic ribosomal L3 protein compared to a non-transgenic control plant.

12. The method of claim 11, wherein said preparing a transgenic plant comprises transforming a protoplast from a cell of a plant with the exogenous nucleic acid to produce a transformed protoplast, and generating the transgenic plant from the transformed protoplast.

13. The method of claim 11, wherein said preparing a transgenic plant comprises introducing the exogenous nucleic acid into tissue of a plant to produce transformed plant tissue, and regenerating the transgenic plant from the transformed plant tissue.

14. A transgenic plant comprising an exogenous nucleic acid comprising a transgene functional therein and that encodes an N-terminal polypeptide fragment of a eucaryotic ribosomal L3 protein selected from the group consisting of an *Arabadopsis* L3 protein (SEQ ID NOS:7 or 8), *Nicotiana tabacum* L3 protein (SEQ ID NOS:9 or 10), yeast L3 protein (SEQ ID NO:11) and rice L3 protein (SEQ ID NO:12), wherein the L3 protein fragment contains the first 21 to about 99 N-terminal amino acid residues of the L3 protein, wherein said plant does not contain a transgene encoding a ribosome inactivating protein (RIP) that targets an L3 eucaryotic protein, and wherein said plant exhibits increased resistance to fungal toxins that target a eucaryotic ribosomal L3 protein compared to a non-transgenic control plant.

15. The transgenic plant of claim 14, wherein the transgene encodes an N-terminal polypeptide fragment of L3 having from the first 21 to 99 N-terminal amino acid residues of the L3 protein.

16. The transgenic plant of claim 14, wherein the transgene encodes an N-terminal polypeptide fragment of L3 having amino acids 1-99 of the L3 protein.

17. The transgenic plant of claim 14, wherein the transgene encodes an N-terminal polypeptide fragment of L3 having amino acids 1-100 of the L3 protein.

18. The transgenic plant of claim 14, wherein the transgene encodes an N-terminal polypeptide fragment of L3 having amino acids 1-21 of the L3 protein.

19. A transgenic seed derived from the transgenic plant of claim 14.

20. A method of making a transgenic plant having increased resistance to infestation by fungi that produce toxins that target a eucaryotic ribosomal L3 protein, comprising preparing a transgenic plant having a genome that contains an exogenous nucleic acid comprising a transgene encoding an N-terminal polypeptide fragment of an *Arabadopsis* L3 protein (SEQ ID NOS:7 or 8), *Nicotiana tabacum* L3 protein (SEQ ID NOS:9 or 10), yeast L3 protein (SEQ ID NO:11) or rice L3 protein (SEQ ID NO:12), wherein the L3 protein fragment contains the first 21 to about 99 N-terminal amino acid residues of the L3 protein, wherein said plant does not contain a transgene encoding a ribosome inactivating protein (RIP) that targets an L3 eucaryotic protein, and wherein expression of the transgene in the transgenic plant confers increased resistance to fungal toxins that target a eucaryotic ribosomal L3 protein compared to a non-transgenic control plant.

21. The method of claim 20, wherein said preparing a transgenic plant comprises transforming a protoplast from a cell of a plant with the exogenous nucleic acid to produce a transformed protoplast, and generating the transgenic plant from the transformed protoplast.

22. The method of claim 20, wherein said preparing a transgenic plant comprises introducing the exogenous nucleic acid into tissue of a plant to produce transformed plant tissue, and regenerating the transgenic plant from the transformed plant tissue.

23. The transgenic plant of claim 1, wherein the transgene encodes an N-terminal polypeptide fragment of a higher plant L3 protein, *Arabidopsis*, or yeast.

* * * * *

SEQUENCE LISTING

```
<160> NUMBER OF SEQ ID NOS: 44

<210> SEQ ID NO 1
<211> LENGTH: 384
<212> TYPE: PRT
<213> ORGANISM: Arabidopsis thaliana

<400> SEQUENCE: 1

Met Ser His Arg Lys Phe Glu His Pro Arg His Gly Ser Leu Gly Phe
 1               5                  10                  15

Leu Pro Arg Lys Arg Ala Asn Arg His Arg Gly Lys Val Lys Ala Phe
             20                  25                  30

Pro Lys Asp Asp Gln Thr Lys Pro Cys Lys Phe Thr Ala Phe Met Gly
         35                  40                  45

Tyr Lys Ala Gly Met Thr His Ile Val Arg Glu Val Glu Lys Pro Gly
     50                  55                  60

Ser Lys Leu His Lys Lys Glu Thr Cys Glu Ala Val Thr Ile Ile Glu
 65                  70                  75                  80

Thr Pro Ala Met Val Val Val Gly Val Val Ala Tyr Val Lys Thr Pro
                 85                  90                  95

Arg Gly Leu Arg Ser Leu Asn Thr Val Trp Ala Gln His Leu Ser Glu
            100                 105                 110

Glu Val Arg Arg Arg Phe Tyr Lys Asn Trp Ala Lys Ser Lys Lys Lys
        115                 120                 125

Ala Phe Thr Gly Tyr Ala Lys Gln Tyr Asp Ser Glu Asp Gly Lys Lys
    130                 135                 140

Gly Ile Gln Ala Gln Leu Glu Lys Met Lys Lys Tyr Ala Thr Val Ile
145                 150                 155                 160

Arg Val Leu Ala His Thr Gln Ile Arg Lys Met Lys Gly Leu Lys Gln
                165                 170                 175

Lys Lys Ala His Met Met Glu Ile Gln Ile Asn Gly Gly Thr Ile Ala
            180                 185                 190

Gln Lys Val Asp Phe Ala Tyr Ser Phe Phe Glu Lys Gln Ile Pro Ile
        195                 200                 205

Glu Ala Val Phe Gln Lys Asp Glu Met Ile Asp Ile Ile Gly Val Thr
    210                 215                 220

Lys Gly Lys Gly Tyr Glu Gly Val Val Thr Arg Trp Gly Val Thr Arg
225                 230                 235                 240

Leu Pro Arg Lys Thr His Arg Gly Leu Arg Lys Val Ala Cys Ile Gly
                245                 250                 255

Ala Trp His Pro Ala Arg Val Ser Tyr Thr Val Ala Arg Ala Gly Gln
            260                 265                 270

Asn Gly Tyr His His Arg Thr Glu Leu Asn Lys Lys Ile Tyr Arg Leu
        275                 280                 285

Gly Lys Val Gly Thr Glu Ala His Thr Ala Met Thr Glu Tyr Asp Arg
    290                 295                 300
```

```
Thr Glu Lys Asp Val Thr Pro Met Gly Gly Phe Pro His Tyr Gly Ile
305                 310                 315                 320

Val Lys Asp Asp Tyr Leu Met Ile Lys Gly Cys Val Gly Pro Lys
            325                 330                 335

Lys Arg Val Val Thr Leu Arg Gln Ser Leu Leu Thr Gln Thr Ser Arg
            340                 345                 350

Leu Ala Leu Glu Glu Ile Lys Leu Lys Phe Ile Asp Thr Ala Ser Ile
            355                 360                 365

Phe Gly His Gly Arg Phe Gln Thr Ser Leu Glu Lys Met Arg Phe Tyr
            370                 375                 380
```

<210> SEQ ID NO 2
<211> LENGTH: 391
<212> TYPE: PRT
<213> ORGANISM: Arabidopsis thaliana

<400> SEQUENCE: 2

```
Met Ser His Arg Lys Phe Glu His Pro Arg His Gly Ser Leu Gly Phe
1               5                   10                  15

Leu Pro Arg Lys Arg Ala Ser Arg His Arg Gly Lys Val Lys Ala Phe
            20                  25                  30

Pro Lys Asp Asp Pro Thr Lys Pro Cys Arg Leu Thr Ser Phe Leu Gly
        35                  40                  45

Tyr Lys Ala Gly Met Thr His Ile Val Arg Asp Val Glu Lys Pro Gly
    50                  55                  60

Ser Lys Leu His Lys Lys Glu Thr Cys Glu Ala Val Thr Ile Ile Glu
65                  70                  75                  80

Thr Pro Pro Met Val Val Val Gly Val Val Gly Tyr Val Lys Thr Pro
            85                  90                  95

Arg Gly Leu Arg Ser Leu Cys Thr Val Trp Ala Gln His Leu Ser Glu
        100                 105                 110

Glu Leu Arg Arg Arg Phe Tyr Lys Asn Trp Ala Lys Ser Lys Lys Lys
    115                 120                 125

Ala Phe Thr Arg Tyr Ser Lys Lys His Glu Thr Glu Glu Gly Lys Lys
130                 135                 140

Asp Ile Gln Ser Gln Leu Glu Lys Met Lys Lys Tyr Cys Ser Val Ile
145                 150                 155                 160

Arg Val Leu Ala His Thr Gln Ile Arg Lys Met Lys Gly Leu Lys Gln
            165                 170                 175

Lys Lys Ala His Leu Asn Glu Ile Gln Ile Asn Gly Gly Asp Ile Ala
        180                 185                 190

Lys Lys Val Asp Tyr Ala Cys Ser Leu Phe Glu Lys Gln Val Pro Val
    195                 200                 205

Asp Ala Ile Phe Gln Lys Asp Glu Met Ile Asp Ile Ile Gly Val Thr
210                 215                 220

Lys Gly Lys Gly Tyr Glu Gly Val Val Thr Arg Trp Gly Val Thr Arg
225                 230                 235                 240

Leu Pro Arg Lys Thr His Arg Gly Leu Arg Lys Val Ala Cys Ile Gly
            245                 250                 255

Ala Trp His Pro Ala Arg Val Ser Tyr Thr Val Ala Arg Ala Gly Gln
        260                 265                 270

Asn Gly Tyr His His Arg Thr Glu Met Asn Lys Lys Val Tyr Arg Val
    275                 280                 285

Gly Lys Val Gly Gln Glu Thr His Ser Ala Met Thr Glu Tyr Asp Arg
290                 295                 300
```

Thr Glu Lys Asp Ile Thr Pro Met Gly Gly Phe Pro His Tyr Gly Ile
305             310             315             320

Val Lys Glu Asp Tyr Leu Met Ile Lys Gly Cys Cys Val Gly Pro Lys
            325             330             335

Lys Arg Val Val Thr Leu Arg Gln Thr Leu Leu Lys Gln Thr Ser Arg
        340             345             350

Leu Ala Met Glu Glu Ile Lys Leu Lys Phe Ile Asp Ala Ala Ser Asn
    355             360             365

Gly Gly His Gly Arg Phe Gln Thr Ser Gln Glu Lys Ala Lys Phe Tyr
370             375             380

Gly Arg Thr Ile Lys Ala Gly
385             390

<210> SEQ ID NO 3
<211> LENGTH: 389
<212> TYPE: PRT
<213> ORGANISM: Nicotiana tabacum

<400> SEQUENCE: 3

Met Ser His Arg Lys Phe Glu His Pro Arg His Gly Ser Leu Gly Phe
1               5               10              15

Leu Pro Arg Lys Arg Ala Ala Arg His Arg Gly Lys Val Lys Ala Phe
            20              25              30

Pro Lys Asp Asp Pro Asn Lys Pro Cys Lys Leu Thr Ala Phe Leu Gly
        35              40              45

Tyr Lys Ala Gly Met Thr His Ile Val Arg Asp Val Glu Lys Pro Gly
    50              55              60

Ser Lys Leu His Lys Lys Glu Thr Cys Glu Ala Val Thr Ile Ile Glu
65              70              75              80

Thr Pro Pro Met Val Ile Val Gly Val Val Gly Tyr Val Lys Thr Pro
                85              90              95

Arg Gly Leu Arg Cys Leu Asn Thr Val Trp Ala Gln His Leu Ser Glu
            100             105             110

Glu Leu Lys Arg Arg Phe Tyr Lys Asn Trp Cys Lys Ser Lys Lys Lys
        115             120             125

Ala Phe Leu Lys Tyr Ser Lys Lys Tyr Glu Ser Asp Glu Gly Lys Lys
    130             135             140

Asp Ile Gln Thr Gln Leu Glu Lys Leu Lys Lys Tyr Ala Cys Val Ile
145             150             155             160

Arg Val Leu Ala His Thr Gln Ile Arg Lys Met Lys Gly Leu Lys Gln
                165             170             175

Lys Lys Ala His Leu Met Glu Ile Gln Val Asn Gly Gly Thr Ile Ala
            180             185             190

Gln Lys Val Asp Phe Ala Tyr Gly Phe Phe Glu Lys Gln Val Pro Val
        195             200             205

Asp Ala Val Phe Gln Lys Asp Glu Met Ile Asp Ile Ile Gly Val Thr
    210             215             220

Lys Gly Lys Gly Tyr Glu Gly Val Val Thr Arg Trp Gly Val Thr Arg
225             230             235             240

Leu Pro Arg Lys Thr His Arg Gly Leu Arg Lys Val Ala Cys Ile Gly
                245             250             255

Ala Trp His Pro Ala Arg Val Ser Tyr Thr Val Ala Arg Ala Gly Gln
            260             265             270

Asn Gly Tyr His His Arg Thr Glu Met Asn Lys Lys Val Tyr Lys Leu
        275             280             285

```
Gly Lys Ala Gly Gln Glu Ser His Ala Ala Val Thr Asp Phe Asp Arg
    290                 295                 300

Thr Glu Lys Asp Ile Thr Pro Met Gly Gly Phe Pro His Tyr Gly Val
305                 310                 315                 320

Val Lys Asp Asp Tyr Leu Leu Ile Lys Gly Cys Cys Val Gly Pro Lys
                325                 330                 335

Lys Arg Val Val Thr Leu Arg Gln Ser Leu Leu Asn Gln Thr Ser Arg
            340                 345                 350

Val Ala Leu Glu Glu Ile Lys Leu Lys Phe Ile Asp Thr Ser Ser Lys
        355                 360                 365

Phe Gly His Gly Arg Phe Gln Thr Thr Gln Glu Lys Gln Lys Phe Tyr
    370                 375                 380

Gly Arg Leu Lys Gly
385

<210> SEQ ID NO 4
<211> LENGTH: 388
<212> TYPE: PRT
<213> ORGANISM: Nicotiana tabacum

<400> SEQUENCE: 4

Met Ser His Arg Lys Phe Glu His Pro Arg His Gly Ser Leu Gly Phe
1               5                   10                  15

Leu Pro Arg Lys Arg Ala Ala Arg His Arg Gly Lys Val Lys Ala Phe
            20                  25                  30

Pro Lys Asp Asp Thr Thr Lys Pro Cys Arg Leu Thr Ala Phe Leu Gly
        35                  40                  45

Tyr Lys Ala Gly Met Thr His Ile Val Arg Val Glu Lys Pro Gly Ser
    50                  55                  60

Lys Leu His Lys Lys Glu Thr Cys Glu Ala Leu Thr Ile Ile Glu Thr
65                  70                  75                  80

Pro Pro Met Ile Val Val Gly Val Val Gly Tyr Val Lys Thr Pro Arg
                85                  90                  95

Gly Leu Arg Cys Leu Ser Thr Val Trp Ala Gln His Leu Ser Glu Glu
            100                 105                 110

Ile Lys Arg Arg Phe Tyr Lys Asn Trp Cys Met Ser Lys Lys Lys Ala
        115                 120                 125

Phe Ala Lys Tyr Ser Lys Lys Tyr Glu Thr Asp Asp Gly Lys Lys Asp
    130                 135                 140

Ile Gln Ala Gln Leu Glu Lys Met Lys Lys Tyr Cys Cys Val Ile Arg
145                 150                 155                 160

Val Leu Ala His Thr Gln Ile Arg Lys Met Lys Gly Leu Lys Gln Lys
                165                 170                 175

Lys Ala His Leu Met Glu Ile Gln Val Asn Gly Gly Asp Val Ser Gln
            180                 185                 190

Lys Val Asp Tyr Ala Tyr Gly Phe Phe Glu Lys Gln Ile Pro Val Asp
        195                 200                 205

Ala Ile Phe Gln Lys Asp Glu Met Ile Asp Ile Ile Gly Val Thr Lys
    210                 215                 220

Gly Lys Gly Tyr Glu Gly Val Val Thr Arg Trp Gly Val Thr Arg Leu
225                 230                 235                 240

Pro Arg Lys Thr His Arg Gly Leu Arg Lys Val Ala Cys Ile Gly Ala
                245                 250                 255

Trp His Pro Ala Arg Val Ser Tyr Thr Val Ala Arg Ala Gly Gln Asn
            260                 265                 270
```

```
Gly Tyr His His Arg Thr Glu Leu Asn Lys Lys Val Tyr Lys Leu Gly
            275                 280                 285

Lys Ala Gly Gln Glu Ser His Ser Ala Ile Thr Glu Phe Asp Arg Thr
        290                 295                 300

Glu Lys Asp Ile Thr Pro Met Gly Gly Phe Pro His Tyr Gly Ile Val
305                 310                 315                 320

Lys Glu Asp Phe Leu Leu Ile Lys Gly Cys Cys Val Gly Pro Lys Lys
            325                 330                 335

Arg Val Val Thr Leu Arg Gln Ser Leu Leu Asn Gln Thr Ser Arg Val
        340                 345                 350

Ala Leu Glu Glu Ile Lys Leu Lys Phe Ile Asp Thr Ser Ser Lys Phe
355                 360                 365

Gly His Gly Arg Phe Gln Thr Thr Gln Glu Lys Asp Lys Phe Tyr Gly
            370                 375                 380

Arg Leu Lys Ala
385

<210> SEQ ID NO 5
<211> LENGTH: 387
<212> TYPE: PRT
<213> ORGANISM: Saccharomyces cerevisiae

<400> SEQUENCE: 5

Met Ser His Arg Lys Tyr Glu Ala Pro Arg His Gly His Leu Gly Phe
1               5                   10                  15

Leu Pro Arg Lys Arg Ala Ala Ser Ile Arg Ala Arg Val Lys Ala Phe
            20                  25                  30

Pro Lys Asp Asp Arg Ser Lys Pro Val Ala Leu Thr Ser Phe Leu Gly
        35                  40                  45

Tyr Lys Ala Gly Met Thr Thr Ile Val Arg Asp Leu Asp Arg Pro Gly
    50                  55                  60

Ser Lys Phe His Lys Arg Glu Val Val Glu Ala Val Thr Val Val Asp
65                  70                  75                  80

Thr Pro Pro Val Val Val Gly Val Val Gly Tyr Val Glu Thr Pro
                85                  90                  95

Arg Gly Leu Arg Ser Leu Thr Thr Val Trp Ala Glu His Leu Ser Asp
            100                 105                 110

Glu Val Lys Arg Arg Phe Tyr Lys Asn Trp Tyr Lys Ser Lys Lys Lys
        115                 120                 125

Ala Phe Thr Lys Tyr Ser Ala Lys Tyr Ala Gln Asp Gly Ala Gly Ile
    130                 135                 140

Glu Arg Glu Leu Ala Arg Ile Lys Lys Tyr Ala Ser Val Val Arg Val
145                 150                 155                 160

Leu Val His Thr Gln Ile Arg Lys Thr Pro Leu Ala Gln Lys Lys Ala
                165                 170                 175

His Leu Ala Glu Ile Gln Leu Asn Gly Gly Ser Ile Ser Glu Lys Val
            180                 185                 190

Asp Trp Ala Arg Glu His Phe Glu Lys Thr Val Ala Val Asp Ser Val
        195                 200                 205

Phe Glu Gln Asn Glu Met Ile Asp Ala Ile Ala Val Thr Lys Gly His
    210                 215                 220

Gly Phe Glu Gly Val Thr His Arg Trp Gly Thr Lys Lys Leu Pro Arg
225                 230                 235                 240

Lys Thr His Arg Gly Leu Arg Lys Val Ala Cys Ile Gly Ala Trp His
                245                 250                 255
```

```
Pro Ala His Val Met Trp Ser Val Ala Arg Ala Gly Gln Arg Gly Tyr
            260                 265                 270

His Ser Arg Thr Ser Ile Asn His Lys Ile Tyr Arg Val Gly Lys Gly
        275                 280                 285

Asp Asp Glu Ala Asn Gly Ala Thr Ser Phe Asp Arg Thr Lys Lys Thr
290                 295                 300

Ile Thr Pro Met Gly Gly Phe Val His Tyr Gly Glu Ile Lys Asn Asp
305                 310                 315                 320

Phe Ile Met Val Lys Gly Cys Ile Pro Gly Asn Arg Lys Arg Ile Val
                325                 330                 335

Thr Leu Arg Lys Ser Leu Tyr Thr Asn Thr Ser Arg Lys Ala Leu Glu
            340                 345                 350

Glu Val Ser Leu Lys Trp Ile Asp Thr Ala Ser Lys Phe Gly Lys Gly
        355                 360                 365

Arg Phe Gln Thr Pro Ala Glu Lys His Ala Phe Met Gly Thr Leu Lys
370                 375                 380

Lys Asp Leu
385

<210> SEQ ID NO 6
<211> LENGTH: 208
<212> TYPE: PRT
<213> ORGANISM: Oryza sativa

<400> SEQUENCE: 6

Asn Tyr Ile Lys Gly Arg Arg Glu Lys Met Ser His Arg Lys Phe Glu
1               5                   10                  15

His Pro Arg Thr Gly Ser Leu Gly Phe Leu Pro Arg Lys Arg Ala Ser
            20                  25                  30

Arg His Arg Gly Lys Cys Lys Ser Phe Pro Lys Asp Asp Lys Thr Lys
        35                  40                  45

Pro Val His Leu Thr Ala Phe Leu Gly Tyr Lys Ala Gly Met Thr His
    50                  55                  60

Ile Val Arg Asp Leu Asp Arg Pro Gly Ser Lys Met His Lys Lys Glu
65                  70                  75                  80

Val Val Glu Ala Val Thr Ile Ile Glu Thr Pro Pro Ile Val Val Val
                85                  90                  95

Gly Val Val Gly Tyr Val Glu Thr Pro Arg Gly Leu Arg Ser Leu Thr
            100                 105                 110

Thr Val Trp Ala Glu His Leu Ser Asp Glu Val Lys Arg Arg Phe Tyr
        115                 120                 125

Lys Asn Trp Tyr Arg Ser Lys Lys Lys Ala Phe Thr Lys Tyr Ala Lys
130                 135                 140

Lys Tyr Thr Glu Gly Ala Lys Pro Ile Glu Gln Gln Leu Glu Arg Ile
145                 150                 155                 160

Lys Lys Tyr Cys Gln Val Val Arg Val Ile Val His Thr Gln Val Arg
                165                 170                 175

Lys Val Lys Asn Gly Gln Lys Lys Ala His Val Met Gln Ile Asn Ser
            180                 185                 190

Thr Val Val Thr Ser Pro Gln Arg Ser Pro Gly Glu Arg Asn Thr Ser
        195                 200                 205

<210> SEQ ID NO 7
<211> LENGTH: 100
<212> TYPE: PRT
<213> ORGANISM: Arabidopsis thaliana
```

-continued

<400> SEQUENCE: 7

Met Ser His Arg Lys Phe Glu His Pro Arg His Gly Ser Leu Gly Phe
1               5                   10                  15

Leu Pro Arg Lys Arg Ala Asn Arg His Arg Gly Lys Val Lys Ala Phe
            20                  25                  30

Pro Lys Asp Asp Gln Thr Lys Pro Cys Lys Phe Thr Ala Phe Met Gly
        35                  40                  45

Tyr Lys Ala Gly Met Thr His Ile Val Arg Glu Val Glu Lys Pro Gly
    50                  55                  60

Ser Lys Leu His Lys Lys Glu Thr Cys Glu Ala Val Thr Ile Ile Glu
65                  70                  75                  80

Thr Pro Ala Met Val Val Val Gly Val Val Ala Tyr Val Lys Thr Pro
                85                  90                  95

Arg Gly Leu Arg
            100

<210> SEQ ID NO 8
<211> LENGTH: 101
<212> TYPE: PRT
<213> ORGANISM: Arabidopsis thaliana

<400> SEQUENCE: 8

Met Ser His Arg Lys Phe Glu His Pro Arg His Gly Ser Leu Gly Phe
1               5                   10                  15

Leu Pro Arg Lys Arg Ala Ser Arg His Arg Gly Lys Val Lys Ala Phe
            20                  25                  30

Pro Lys Asp Asp Pro Thr Lys Pro Cys Arg Leu Thr Ser Phe Leu Gly
        35                  40                  45

Tyr Lys Ala Gly Met Thr His Ile Val Phe Arg Asp Val Glu Lys Pro
    50                  55                  60

Gly Ser Lys Leu His Lys Lys Glu Thr Cys Glu Ala Val Thr Ile Ile
65                  70                  75                  80

Glu Thr Pro Pro Met Val Val Val Gly Val Val Gly Tyr Val Lys Thr
                85                  90                  95

Pro Arg Gly Leu Arg
            100

<210> SEQ ID NO 9
<211> LENGTH: 100
<212> TYPE: PRT
<213> ORGANISM: Nicotiana tabacum

<400> SEQUENCE: 9

Met Ser His Arg Lys Phe Glu His Pro Arg His Gly Ser Leu Gly Phe
1               5                   10                  15

Leu Pro Arg Lys Arg Ala Ala Arg His Arg Gly Lys Val Lys Ala Phe
            20                  25                  30

Pro Lys Asp Asp Pro Asn Lys Pro Cys Lys Leu Thr Ala Phe Leu Gly
        35                  40                  45

Tyr Lys Ala Gly Met Thr His Ile Val Arg Asp Val Glu Lys Pro Gly
    50                  55                  60

Ser Lys Leu His Lys Lys Glu Thr Cys Glu Ala Val Thr Ile Ile Glu
65                  70                  75                  80

Thr Pro Pro Met Val Ile Val Gly Val Val Gly Tyr Val Lys Thr Pro
                85                  90                  95

Arg Gly Leu Arg

```
                100

<210> SEQ ID NO 10
<211> LENGTH: 100
<212> TYPE: PRT
<213> ORGANISM: Nicotiana tabacum

<400> SEQUENCE: 10

Met Ser His Arg Lys Phe Glu His Pro Arg His Gly Ser Leu Gly Phe
1               5                   10                  15

Leu Pro Arg Lys Arg Ala Ala Arg His Arg Gly Lys Val Lys Ala Phe
                20                  25                  30

Pro Lys Asp Asp Thr Thr Lys Pro Cys Arg Leu Thr Ala Phe Leu Gly
            35                  40                  45

Tyr Lys Ala Gly Met Thr His Ile Val Arg Asp Val Glu Lys Pro Gly
    50                  55                  60

Ser Lys Leu His Lys Lys Glu Thr Cys Glu Leu Val Thr Ile Ile Glu
65                  70                  75                  80

Thr Pro Pro Met Ile Val Val Gly Val Val Gly Tyr Val Lys Thr Pro
                85                  90                  95

Arg Gly Leu Arg
            100

<210> SEQ ID NO 11
<211> LENGTH: 100
<212> TYPE: PRT
<213> ORGANISM: Saccharomyces cerevisiae

<400> SEQUENCE: 11

Met Ser His Arg Lys Tyr Glu Ala Pro Arg His Gly His Leu Gly Phe
1               5                   10                  15

Leu Pro Arg Lys Arg Ala Ala Ser Ile Arg Ala Arg Val Lys Ala Phe
                20                  25                  30

Pro Lys Asp Asp Arg Ser Lys Pro Val Ala Leu Thr Ser Phe Leu Gly
            35                  40                  45

Tyr Lys Ala Gly Met Thr Thr Ile Val Arg Asp Leu Asp Arg Pro Gly
    50                  55                  60

Ser Lys Phe His Lys Arg Glu Val Val Glu Ala Val Thr Val Val Asp
65                  70                  75                  80

Thr Pro Pro Val Val Val Val Gly Val Val Gly Tyr Val Glu Thr Pro
                85                  90                  95

Arg Gly Leu Arg
            100

<210> SEQ ID NO 12
<211> LENGTH: 109
<212> TYPE: PRT
<213> ORGANISM: Oryza sativa

<400> SEQUENCE: 12

Asn Tyr Ile Lys Gly Arg Arg Glu Lys Met Ser His Arg Lys Phe Glu
1               5                   10                  15

His Pro Arg Thr Gly Ser Leu Gly Phe Leu Pro Arg Lys Arg Ala Ser
                20                  25                  30

Arg His Arg Gly Lys Cys Lys Ser Phe Pro Lys Asp Asp Lys Thr Lys
            35                  40                  45

Pro Val His Leu Thr Ala Phe Leu Gly Tyr Lys Ala Gly Met Thr His
    50                  55                  60
```

```
Ile Val Arg Asp Leu Asp Arg Pro Gly Ser Lys Met His Lys Lys Glu
 65                  70                  75                  80

Val Val Glu Ala Val Thr Ile Ile Glu Thr Pro Pro Ile Val Val Val
                 85                  90                  95

Gly Val Val Gly Tyr Val Glu Thr Pro Arg Gly Leu Arg
                100                 105

<210> SEQ ID NO 13
<211> LENGTH: 1164
<212> TYPE: DNA
<213> ORGANISM: Saccharomyces cerevisiae
<220> FEATURE:
<221> NAME/KEY: CDS
<222> LOCATION: (1)..(1161)

<400> SEQUENCE: 13
```

| | | | | | | | | | | | | | | | | |
|---|---|---|---|---|---|---|---|---|---|---|---|---|---|---|---|---|
| atg | tct | cac | aga | aag | tac | gaa | gca | cca | cgt | cac | ggt | cat | tta | ggt | ttc | 48 |
| Met | Ser | His | Arg | Lys | Tyr | Glu | Ala | Pro | Arg | His | Gly | His | Leu | Gly | Phe | |
| 1 | | | | 5 | | | | | 10 | | | | | 15 | | |
| ttg | cca | aga | aag | aga | gct | gcc | tcc | atc | aga | gct | aga | gtt | aag | gct | ttt | 96 |
| Leu | Pro | Arg | Lys | Arg | Ala | Ala | Ser | Ile | Arg | Ala | Arg | Val | Lys | Ala | Phe | |
| | | | 20 | | | | | 25 | | | | | 30 | | | |
| cca | aag | gat | gac | aga | tcc | aag | cca | gtt | gct | cta | act | tcc | ttc | ttg | ggt | 144 |
| Pro | Lys | Asp | Asp | Arg | Ser | Lys | Pro | Val | Ala | Leu | Thr | Ser | Phe | Leu | Gly | |
| | | 35 | | | | | 40 | | | | | 45 | | | | |
| tac | aag | gct | ggt | atg | acc | acc | att | gtc | aga | gat | ttg | gac | aga | cca | ggt | 192 |
| Tyr | Lys | Ala | Gly | Met | Thr | Thr | Ile | Val | Arg | Asp | Leu | Asp | Arg | Pro | Gly | |
| 50 | | | | | 55 | | | | | 60 | | | | | | |
| tct | aag | ttc | cac | aag | cgt | gaa | gtt | gtc | gaa | gct | gtc | acc | gtt | gtt | gac | 240 |
| Ser | Lys | Phe | His | Lys | Arg | Glu | Val | Val | Glu | Ala | Val | Thr | Val | Val | Asp | |
| 65 | | | | 70 | | | | | 75 | | | | | 80 | | |
| act | cca | cca | gtt | gtc | gtt | gtt | ggt | gtt | gtc | ggt | tac | gtc | gaa | acc | cca | 288 |
| Thr | Pro | Pro | Val | Val | Val | Val | Gly | Val | Val | Gly | Tyr | Val | Glu | Thr | Pro | |
| | | | 85 | | | | | 90 | | | | | 95 | | | |
| aga | ggt | ttg | aga | tct | ttg | acc | acc | gtc | tgg | gct | gaa | cat | ttg | tct | gac | 336 |
| Arg | Gly | Leu | Arg | Ser | Leu | Thr | Thr | Val | Trp | Ala | Glu | His | Leu | Ser | Asp | |
| | | | 100 | | | | | 105 | | | | | 110 | | | |
| gaa | gtc | aag | aga | aga | ttc | tac | aag | aac | tgg | tac | aag | tct | aag | aag | aag | 384 |
| Glu | Val | Lys | Arg | Arg | Phe | Tyr | Lys | Asn | Trp | Tyr | Lys | Ser | Lys | Lys | Lys | |
| | | 115 | | | | | 120 | | | | | 125 | | | | |
| gct | ttc | acc | aaa | tac | tct | gcc | aag | tac | gct | caa | gat | ggt | gct | ggt | att | 432 |
| Ala | Phe | Thr | Lys | Tyr | Ser | Ala | Lys | Tyr | Ala | Gln | Asp | Gly | Ala | Gly | Ile | |
| | 130 | | | | | 135 | | | | | 140 | | | | | |
| gaa | aga | gaa | ttg | gct | aga | atc | aag | aag | tac | gct | tcc | gtc | gtc | aga | gtt | 480 |
| Glu | Arg | Glu | Leu | Ala | Arg | Ile | Lys | Lys | Tyr | Ala | Ser | Val | Val | Arg | Val | |
| 145 | | | | | 150 | | | | | 155 | | | | | 160 | |
| ttg | gtc | cac | act | caa | atc | aga | aag | act | cca | ttg | gct | caa | aag | aag | gct | 528 |
| Leu | Val | His | Thr | Gln | Ile | Arg | Lys | Thr | Pro | Leu | Ala | Gln | Lys | Lys | Ala | |
| | | | | 165 | | | | | 170 | | | | | 175 | | |
| cat | ttg | gct | gaa | atc | caa | ttg | aac | ggt | ggt | tcc | atc | tct | gaa | aag | gtt | 576 |
| His | Leu | Ala | Glu | Ile | Gln | Leu | Asn | Gly | Gly | Ser | Ile | Ser | Glu | Lys | Val | |
| | | | 180 | | | | | 185 | | | | | 190 | | | |
| gac | tgg | gct | cgt | gaa | cat | ttc | gaa | aag | act | gtt | gct | gtc | gac | agc | gtt | 624 |
| Asp | Trp | Ala | Arg | Glu | His | Phe | Glu | Lys | Thr | Val | Ala | Val | Asp | Ser | Val | |
| | | | 195 | | | | | 200 | | | | | 205 | | | |
| ttt | gaa | caa | aac | gaa | atg | att | gac | gct | att | gct | gtc | acc | aag | ggt | cac | 672 |
| Phe | Glu | Gln | Asn | Glu | Met | Ile | Asp | Ala | Ile | Ala | Val | Thr | Lys | Gly | His | |
| | 210 | | | | | 215 | | | | | 220 | | | | | |
| ggt | ttc | gaa | ggt | gtt | acc | cac | aga | tgg | ggt | act | aag | aaa | ttg | cca | aga | 720 |
| Gly | Phe | Glu | Gly | Val | Thr | His | Arg | Trp | Gly | Thr | Lys | Lys | Leu | Pro | Arg | |
| 225 | | | | | 230 | | | | | 235 | | | | | 240 | |

```
aag act cac aga ggt cta aga aag gtt gct tgt att ggt gct tgg cat    768
Lys Thr His Arg Gly Leu Arg Lys Val Ala Cys Ile Gly Ala Trp His
            245                 250                 255 cca gcc cac gtt atg tgg agt gtt gcc aga gct ggt caa aga ggt tac    816
Pro Ala His Val Met Trp Ser Val Ala Arg Ala Gly Gln Arg Gly Tyr
        260                 265                 270 cat tcc aga acc tcc att aac cac aag att tac aga gtc ggt aag ggt    864
His Ser Arg Thr Ser Ile Asn His Lys Ile Tyr Arg Val Gly Lys Gly
    275                 280                 285 gat gat gaa gct aac ggt gct acc agc ttc gac aga acc aag aag act    912
Asp Asp Glu Ala Asn Gly Ala Thr Ser Phe Asp Arg Thr Lys Lys Thr
290                 295                 300 att acc cca atg ggt ggt ttc gtc cac tac ggt gaa att aag aac gac    960
Ile Thr Pro Met Gly Gly Phe Val His Tyr Gly Glu Ile Lys Asn Asp
305                 310                 315                 320 ttc atc atg gtt aaa ggt tgt atc cca ggt aac aga aag aga att gtt   1008
Phe Ile Met Val Lys Gly Cys Ile Pro Gly Asn Arg Lys Arg Ile Val
                325                 330                 335 act ttg aga aag tct ttg tac acc aac act tct aga aag gct ttg gaa   1056
Thr Leu Arg Lys Ser Leu Tyr Thr Asn Thr Ser Arg Lys Ala Leu Glu
            340                 345                 350 gaa gtc agc ttg aag tgg att gac act gct tct aag ttc ggt aag ggt   1104
Glu Val Ser Leu Lys Trp Ile Asp Thr Ala Ser Lys Phe Gly Lys Gly
        355                 360                 365 aga ttc caa acc cca gct gaa aag cat gct ttc atg ggt act ttg aag   1152
Arg Phe Gln Thr Pro Ala Glu Lys His Ala Phe Met Gly Thr Leu Lys
    370                 375                 380 aag gac ttg taa                                                    1164
Lys Asp Leu
385

<210> SEQ ID NO 14
<211> LENGTH: 387
<212> TYPE: PRT
<213> ORGANISM: Saccharomyces cerevisiae

<400> SEQUENCE: 14

Met Ser His Arg Lys Tyr Glu Ala Pro Arg His Gly His Leu Gly Phe
1               5                   10                  15

Leu Pro Arg Lys Arg Ala Ala Ser Ile Arg Ala Arg Val Lys Ala Phe
            20                  25                  30

Pro Lys Asp Asp Arg Ser Lys Pro Val Ala Leu Thr Ser Phe Leu Gly
        35                  40                  45

Tyr Lys Ala Gly Met Thr Thr Ile Val Arg Asp Leu Asp Arg Pro Gly
    50                  55                  60

Ser Lys Phe His Lys Arg Glu Val Val Glu Ala Val Thr Val Val Asp
65                  70                  75                  80

Thr Pro Pro Val Val Val Gly Val Val Gly Tyr Val Glu Thr Pro
                85                  90                  95

Arg Gly Leu Arg Ser Leu Thr Thr Val Trp Ala Glu His Leu Ser Asp
            100                 105                 110

Glu Val Lys Arg Arg Phe Tyr Lys Asn Trp Tyr Lys Ser Lys Lys Lys
        115                 120                 125

Ala Phe Thr Lys Tyr Ser Ala Lys Tyr Ala Gln Asp Gly Ala Gly Ile
    130                 135                 140

Glu Arg Glu Leu Ala Arg Ile Lys Lys Tyr Ala Ser Val Val Arg Val
145                 150                 155                 160

Leu Val His Thr Gln Ile Arg Lys Thr Pro Leu Ala Gln Lys Lys Ala
                165                 170                 175
```

His Leu Ala Glu Ile Gln Leu Asn Gly Gly Ser Ile Ser Glu Lys Val
            180                 185                 190

Asp Trp Ala Arg Glu His Phe Glu Lys Thr Val Ala Val Asp Ser Val
        195                 200                 205

Phe Glu Gln Asn Glu Met Ile Asp Ala Ile Ala Val Thr Lys Gly His
210                 215                 220

Gly Phe Glu Gly Val Thr His Arg Trp Gly Thr Lys Lys Leu Pro Arg
225                 230                 235                 240

Lys Thr His Arg Gly Leu Arg Lys Val Ala Cys Ile Gly Ala Trp His
                245                 250                 255

Pro Ala His Val Met Trp Ser Val Ala Arg Ala Gly Gln Arg Gly Tyr
            260                 265                 270

His Ser Arg Thr Ser Ile Asn His Lys Ile Tyr Arg Val Gly Lys Gly
        275                 280                 285

Asp Asp Glu Ala Asn Gly Ala Thr Ser Phe Asp Arg Thr Lys Lys Thr
290                 295                 300

Ile Thr Pro Met Gly Gly Phe Val His Tyr Gly Glu Ile Lys Asn Asp
305                 310                 315                 320

Phe Ile Met Val Lys Gly Cys Ile Pro Gly Asn Arg Lys Arg Ile Val
                325                 330                 335

Thr Leu Arg Lys Ser Leu Tyr Thr Asn Thr Ser Arg Lys Ala Leu Glu
            340                 345                 350

Glu Val Ser Leu Lys Trp Ile Asp Thr Ala Ser Lys Phe Gly Lys Gly
        355                 360                 365

Arg Phe Gln Thr Pro Ala Glu Lys His Ala Phe Met Gly Thr Leu Lys
370                 375                 380

Lys Asp Leu
385

<210> SEQ ID NO 15
<211> LENGTH: 1170
<212> TYPE: DNA
<213> ORGANISM: Nicotiana tabacum
<220> FEATURE:
<221> NAME/KEY: CDS
<222> LOCATION: (1)..(1167)

<400> SEQUENCE: 15 atg tct cac agg aag ttt gag cat cca aga cac ggt tct ttg gga ttt       48
Met Ser His Arg Lys Phe Glu His Pro Arg His Gly Ser Leu Gly Phe
1               5                   10                  15 ctg ccc agg aag cgt gct gcc aga cac agg gga aag gtg aag gca ttc       96
Leu Pro Arg Lys Arg Ala Ala Arg His Arg Gly Lys Val Lys Ala Phe
            20                  25                  30 cca aaa gat gat cca aac aag ccc tgc aag cta act gcc ttc ttg ggc      144
Pro Lys Asp Asp Pro Asn Lys Pro Cys Lys Leu Thr Ala Phe Leu Gly
        35                  40                  45 tac aaa gct ggc atg act cac att gtc aga gat gtt gaa aaa cct gga      192
Tyr Lys Ala Gly Met Thr His Ile Val Arg Asp Val Glu Lys Pro Gly
    50                  55                  60 tca aaa ctc cac aag aaa gag aca tgt gaa gct gtc acc atc att gaa      240
Ser Lys Leu His Lys Lys Glu Thr Cys Glu Ala Val Thr Ile Ile Glu
65                  70                  75                  80 aca cct cca atg gtg att gtt ggt gtt gtt ggg tat gtg aag aca cct      288
Thr Pro Pro Met Val Ile Val Gly Val Val Gly Tyr Val Lys Thr Pro
                85                  90                  95 cgt ggt ctt cgt tgc ctg aac act gtc tgg gct caa cat ctc agt gaa      336
Arg Gly Leu Arg Cys Leu Asn Thr Val Trp Ala Gln His Leu Ser Glu

```
                   100                 105                 110
gag ctt aag agg agg ttc tac aag aac tgg tgc aag tcc aag aag aag        384
Glu Leu Lys Arg Arg Phe Tyr Lys Asn Trp Cys Lys Ser Lys Lys Lys
        115                 120                 125 gcc ttc ttg aaa tac tcc aag aaa tat gaa tct gat gaa ggg aaa aag        432
Ala Phe Leu Lys Tyr Ser Lys Lys Tyr Glu Ser Asp Glu Gly Lys Lys
130                 135                 140 gac atc cag aca cag ctg gag aaa ttg aag aag tat gca tgc gtc atc        480
Asp Ile Gln Thr Gln Leu Glu Lys Leu Lys Lys Tyr Ala Cys Val Ile
145                 150                 155                 160 cgt gtt ttg gct cac act cag ata agg aag atg aag ggt ctg aaa cag        528
Arg Val Leu Ala His Thr Gln Ile Arg Lys Met Lys Gly Leu Lys Gln
                165                 170                 175 aag aaa gcc cat ttg atg gag ata cag gtg aat gga ggg aca att gct        576
Lys Lys Ala His Leu Met Glu Ile Gln Val Asn Gly Gly Thr Ile Ala
            180                 185                 190 cag aag gtt gac ttt gca tat ggt ttc ttc gag aag cag gtt cca gtt        624
Gln Lys Val Asp Phe Ala Tyr Gly Phe Phe Glu Lys Gln Val Pro Val
        195                 200                 205 gat gct gtt ttt cag aag gat gag atg att gac atc att ggt gtc acc        672
Asp Ala Val Phe Gln Lys Asp Glu Met Ile Asp Ile Ile Gly Val Thr
210                 215                 220 aag ggt aag ggt tat gaa ggt gtt gta act cgt tgg ggt gtg aca cgt        720
Lys Gly Lys Gly Tyr Glu Gly Val Val Thr Arg Trp Gly Val Thr Arg
225                 230                 235                 240 ctt cct cgc aaa acc cac agg ggt ctg cgt aag gtt gct tgt att gga        768
Leu Pro Arg Lys Thr His Arg Gly Leu Arg Lys Val Ala Cys Ile Gly
                245                 250                 255 gcc tgg cac cct gct aga gtt tcc tac aca gtt gcc cgt gct ggt caa        816
Ala Trp His Pro Ala Arg Val Ser Tyr Thr Val Ala Arg Ala Gly Gln
            260                 265                 270 aat gga tac cat cac cgt acc gag atg aac aag aag gtt tac aaa cta        864
Asn Gly Tyr His His Arg Thr Glu Met Asn Lys Lys Val Tyr Lys Leu
        275                 280                 285 ggg aag gct ggc caa gag tcc cat gct gct gta act gat ttt gac agg        912
Gly Lys Ala Gly Gln Glu Ser His Ala Ala Val Thr Asp Phe Asp Arg
290                 295                 300 acc gag aaa gac att act ccc atg ggt gga ttt ccc cat tat ggt gtg        960
Thr Glu Lys Asp Ile Thr Pro Met Gly Gly Phe Pro His Tyr Gly Val
305                 310                 315                 320 gtg aag gat gat tac ctg ttg atc aag gga tgc tgt gtt ggt cct aag       1008
Val Lys Asp Asp Tyr Leu Leu Ile Lys Gly Cys Cys Val Gly Pro Lys
                325                 330                 335 aag agg gtt gta acc ctt cgt cag tcc ctg ctc aac cag acc tct cgt       1056
Lys Arg Val Val Thr Leu Arg Gln Ser Leu Leu Asn Gln Thr Ser Arg
            340                 345                 350 gtc gct ctt gag gag att aag ctg aag ttc atc gat aca tcc tca aag       1104
Val Ala Leu Glu Glu Ile Lys Leu Lys Phe Ile Asp Thr Ser Ser Lys
        355                 360                 365 ttt gga cat ggt cgc ttc cag acc act caa gag aag cag aaa ttc tat       1152
Phe Gly His Gly Arg Phe Gln Thr Thr Gln Glu Lys Gln Lys Phe Tyr
370                 375                 380 ggc cgg ttg aag ggt taa                                                1170
Gly Arg Leu Lys Gly
385

<210> SEQ ID NO 16
<211> LENGTH: 389
<212> TYPE: PRT
<213> ORGANISM: Nicotiana tabacum
```

<400> SEQUENCE: 16

```
Met Ser His Arg Lys Phe Glu His Pro Arg His Gly Ser Leu Gly Phe
 1               5                  10                  15

Leu Pro Arg Lys Arg Ala Ala Arg His Arg Gly Lys Val Lys Ala Phe
             20                  25                  30

Pro Lys Asp Asp Pro Asn Lys Pro Cys Lys Leu Thr Ala Phe Leu Gly
         35                  40                  45

Tyr Lys Ala Gly Met Thr His Ile Val Arg Asp Val Glu Lys Pro Gly
     50                  55                  60

Ser Lys Leu His Lys Lys Glu Thr Cys Glu Ala Val Thr Ile Ile Glu
 65                  70                  75                  80

Thr Pro Pro Met Val Ile Val Gly Val Val Gly Tyr Val Lys Thr Pro
                 85                  90                  95

Arg Gly Leu Arg Cys Leu Asn Thr Val Trp Ala Gln His Leu Ser Glu
            100                 105                 110

Glu Leu Lys Arg Arg Phe Tyr Lys Asn Trp Cys Lys Ser Lys Lys Lys
        115                 120                 125

Ala Phe Leu Lys Tyr Ser Lys Lys Tyr Glu Ser Asp Glu Gly Lys Lys
    130                 135                 140

Asp Ile Gln Thr Gln Leu Glu Lys Leu Lys Lys Tyr Ala Cys Val Ile
145                 150                 155                 160

Arg Val Leu Ala His Thr Gln Ile Arg Lys Met Lys Gly Leu Lys Gln
                165                 170                 175

Lys Lys Ala His Leu Met Glu Ile Gln Val Asn Gly Gly Thr Ile Ala
            180                 185                 190

Gln Lys Val Asp Phe Ala Tyr Gly Phe Phe Glu Lys Gln Val Pro Val
        195                 200                 205

Asp Ala Val Phe Gln Lys Asp Glu Met Ile Asp Ile Ile Gly Val Thr
    210                 215                 220

Lys Gly Lys Gly Tyr Glu Gly Val Val Thr Arg Trp Gly Val Thr Arg
225                 230                 235                 240

Leu Pro Arg Lys Thr His Arg Gly Leu Arg Lys Val Ala Cys Ile Gly
                245                 250                 255

Ala Trp His Pro Ala Arg Val Ser Tyr Thr Val Ala Arg Ala Gly Gln
            260                 265                 270

Asn Gly Tyr His His Arg Thr Glu Met Asn Lys Lys Val Tyr Lys Leu
        275                 280                 285

Gly Lys Ala Gly Gln Glu Ser His Ala Ala Val Thr Asp Phe Asp Arg
    290                 295                 300

Thr Glu Lys Asp Ile Thr Pro Met Gly Gly Phe Pro His Tyr Gly Val
305                 310                 315                 320

Val Lys Asp Asp Tyr Leu Leu Ile Lys Gly Cys Cys Val Gly Pro Lys
                325                 330                 335

Lys Arg Val Val Thr Leu Arg Gln Ser Leu Leu Asn Gln Thr Ser Arg
            340                 345                 350

Val Ala Leu Glu Glu Ile Lys Leu Lys Phe Ile Asp Thr Ser Ser Lys
        355                 360                 365

Phe Gly His Gly Arg Phe Gln Thr Thr Gln Glu Lys Gln Lys Phe Tyr
    370                 375                 380

Gly Arg Leu Lys Gly
385
```

<210> SEQ ID NO 17
<211> LENGTH: 1164

-continued

<212> TYPE: DNA
<213> ORGANISM: Saccharomyces cerevisiae
<220> FEATURE:
<221> NAME/KEY: CDS
<222> LOCATION: (1)..(1161)

<400> SEQUENCE: 17

```
atg tct cac aga aag tac gaa gca cca cgt cac ggt cat tta ggt ttc     48
Met Ser His Arg Lys Tyr Glu Ala Pro Arg His Gly His Leu Gly Phe
1               5                   10                  15 ttg cca aga aag aga gct gcc tcc atc aga gct aga gtt aag gct ttt     96
Leu Pro Arg Lys Arg Ala Ala Ser Ile Arg Ala Arg Val Lys Ala Phe
            20                  25                  30 cca aag gat gac aga tcc aag cca gtt gct cta act tcc ttc ttg ggt    144
Pro Lys Asp Asp Arg Ser Lys Pro Val Ala Leu Thr Ser Phe Leu Gly
        35                  40                  45 tac aag gct ggt atg acc acc att gtc aga gat ttg gac aga cca ggt    192
Tyr Lys Ala Gly Met Thr Thr Ile Val Arg Asp Leu Asp Arg Pro Gly
    50                  55                  60 tct aag ttc cac aag cgt gaa gtt gtc gaa gct gtc acc gtt gtt gac    240
Ser Lys Phe His Lys Arg Glu Val Val Glu Ala Val Thr Val Val Asp
65                  70                  75                  80 act cca cca gtt gtc gtt gtt ggt gtt gtc ggt tac gtc gaa acc cca    288
Thr Pro Pro Val Val Val Val Gly Val Val Gly Tyr Val Glu Thr Pro
                85                  90                  95 aga ggt ttg aga tct ttg acc acc gtc tgg gct gaa cat ttg tct gac    336
Arg Gly Leu Arg Ser Leu Thr Thr Val Trp Ala Glu His Leu Ser Asp
            100                 105                 110 gaa gtc aag aga aga ttc tac aag aac tgg tac aag tct aag aag aag    384
Glu Val Lys Arg Arg Phe Tyr Lys Asn Trp Tyr Lys Ser Lys Lys Lys
        115                 120                 125 gct ttc acc aaa tac tct gcc aag tac gct caa gat ggt gct ggt att    432
Ala Phe Thr Lys Tyr Ser Ala Lys Tyr Ala Gln Asp Gly Ala Gly Ile
    130                 135                 140 gaa aga gaa ttg gct aga atc aag aag tac gct tcc gtc gtc aga gtt    480
Glu Arg Glu Leu Ala Arg Ile Lys Lys Tyr Ala Ser Val Val Arg Val
145                 150                 155                 160 ttg gtc cac act caa atc aga aag act cca ttg gct caa aag aag gct    528
Leu Val His Thr Gln Ile Arg Lys Thr Pro Leu Ala Gln Lys Lys Ala
                165                 170                 175 cat ttg gct gaa atc caa ttg aac ggt ggt tcc atc tct gaa aag gtt    576
His Leu Ala Glu Ile Gln Leu Asn Gly Gly Ser Ile Ser Glu Lys Val
            180                 185                 190 gac tgg gct cgt gaa cat ttc gaa aag act gtt gct gtc gac agc gtt    624
Asp Trp Ala Arg Glu His Phe Glu Lys Thr Val Ala Val Asp Ser Val
        195                 200                 205 ttt gaa caa aac gaa atg att gac gct att gct gtc acc aag ggt cac    672
Phe Glu Gln Asn Glu Met Ile Asp Ala Ile Ala Val Thr Lys Gly His
    210                 215                 220 ggt ttc gaa ggt gtt acc cac aga tgg ggt act aag aaa ttg cca aga    720
Gly Phe Glu Gly Val Thr His Arg Trp Gly Thr Lys Lys Leu Pro Arg
225                 230                 235                 240 aag act cac aga ggt cta aga aag gtt gct tgt att ggt gct tgc cat    768
Lys Thr His Arg Gly Leu Arg Lys Val Ala Cys Ile Gly Ala Cys His
                245                 250                 255 cca gcc cac gtt atg tgg agt gtt gcc aga gct ggt caa aga ggt tac    816
Pro Ala His Val Met Trp Ser Val Ala Arg Ala Gly Gln Arg Gly Tyr
            260                 265                 270 cat tcc aga acc tcc att aac cac aag att tac aga gtc ggt aag ggt    864
His Ser Arg Thr Ser Ile Asn His Lys Ile Tyr Arg Val Gly Lys Gly
        275                 280                 285
```

```
gat gat gaa gct aac ggt gct acc agc ttc gac aga acc aag aag act      912
Asp Asp Glu Ala Asn Gly Ala Thr Ser Phe Asp Arg Thr Lys Lys Thr
    290                 295                 300 att acc cca atg ggt ggt ttc gtc cac tac ggt gaa att aag aac gac      960
Ile Thr Pro Met Gly Gly Phe Val His Tyr Gly Glu Ile Lys Asn Asp
305                 310                 315                 320 ttc atc atg gtt aaa ggt tgt atc cca ggt aac aga aag aga att gtt     1008
Phe Ile Met Val Lys Gly Cys Ile Pro Gly Asn Arg Lys Arg Ile Val
                325                 330                 335 act ttg aga aag tct ttg tac acc aac act tct aga aag gct ttg gaa     1056
Thr Leu Arg Lys Ser Leu Tyr Thr Asn Thr Ser Arg Lys Ala Leu Glu
            340                 345                 350 gaa gtc agc ttg aag tgg att gac act gct tct aag ttc ggt aag ggt     1104
Glu Val Ser Leu Lys Trp Ile Asp Thr Ala Ser Lys Phe Gly Lys Gly
        355                 360                 365 aga ttc caa acc cca gct gaa aag cat gct ttc atg ggt act ttg aag     1152
Arg Phe Gln Thr Pro Ala Glu Lys His Ala Phe Met Gly Thr Leu Lys
    370                 375                 380 aag gac ttg taa                                                     1164
Lys Asp Leu
385
```

<210> SEQ ID NO 18
<211> LENGTH: 387
<212> TYPE: PRT
<213> ORGANISM: Saccharomyces cerevisiae

<400> SEQUENCE: 18

```
Met Ser His Arg Lys Tyr Glu Ala Pro Arg His Gly His Leu Gly Phe
1               5                   10                  15

Leu Pro Arg Lys Arg Ala Ala Ser Ile Arg Ala Arg Val Lys Ala Phe
            20                  25                  30

Pro Lys Asp Asp Arg Ser Lys Pro Val Ala Leu Thr Ser Phe Leu Gly
        35                  40                  45

Tyr Lys Ala Gly Met Thr Thr Ile Val Arg Asp Leu Asp Arg Pro Gly
    50                  55                  60

Ser Lys Phe His Lys Arg Glu Val Val Glu Ala Val Thr Val Val Asp
65                  70                  75                  80

Thr Pro Pro Val Val Val Gly Val Val Gly Tyr Val Glu Thr Pro
                85                  90                  95

Arg Gly Leu Arg Ser Leu Thr Thr Val Trp Ala Glu His Leu Ser Asp
            100                 105                 110

Glu Val Lys Arg Arg Phe Tyr Lys Asn Trp Tyr Lys Ser Lys Lys Lys
        115                 120                 125

Ala Phe Thr Lys Tyr Ser Ala Lys Tyr Ala Gln Asp Gly Ala Gly Ile
    130                 135                 140

Glu Arg Glu Leu Ala Arg Ile Lys Lys Tyr Ala Ser Val Val Arg Val
145                 150                 155                 160

Leu Val His Thr Gln Ile Arg Lys Thr Pro Leu Ala Gln Lys Lys Ala
                165                 170                 175

His Leu Ala Glu Ile Gln Leu Asn Gly Gly Ser Ile Ser Glu Lys Val
            180                 185                 190

Asp Trp Ala Arg Glu His Phe Glu Lys Thr Val Ala Val Asp Ser Val
        195                 200                 205

Phe Glu Gln Asn Glu Met Ile Asp Ala Ile Ala Val Thr Lys Gly His
    210                 215                 220

Gly Phe Glu Gly Val Thr His Arg Trp Gly Thr Lys Lys Leu Pro Arg
225                 230                 235                 240
```

```
Lys Thr His Arg Gly Leu Arg Lys Val Ala Cys Ile Gly Ala Cys His
                245                 250                 255

Pro Ala His Val Met Trp Ser Val Ala Arg Ala Gly Gln Arg Gly Tyr
            260                 265                 270

His Ser Arg Thr Ser Ile Asn His Lys Ile Tyr Arg Val Gly Lys Gly
        275                 280                 285

Asp Asp Glu Ala Asn Gly Ala Thr Ser Phe Arg Thr Lys Lys Thr
    290                 295                 300

Ile Thr Pro Met Gly Gly Phe Val His Tyr Gly Glu Ile Lys Asn Asp
305                 310                 315                 320

Phe Ile Met Val Lys Gly Cys Ile Pro Gly Asn Arg Lys Arg Ile Val
                325                 330                 335

Thr Leu Arg Lys Ser Leu Tyr Thr Asn Thr Ser Arg Lys Ala Leu Glu
            340                 345                 350

Glu Val Ser Leu Lys Trp Ile Asp Thr Ala Ser Lys Phe Gly Lys Gly
        355                 360                 365

Arg Phe Gln Thr Pro Ala Glu Lys His Ala Phe Met Gly Thr Leu Lys
    370                 375                 380

Lys Asp Leu
385

<210> SEQ ID NO 19
<211> LENGTH: 1360
<212> TYPE: DNA
<213> ORGANISM: Phytolacca americana
<220> FEATURE:
<221> NAME/KEY: CDS
<222> LOCATION: (207)..(1145)

<400> SEQUENCE: 19
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaact atg aag tcg atg ctt gtg gtg aca ata     233
                              Met Lys Ser Met Leu Val Val Thr Ile
                                1               5 tca ata tgg ctc att ctt gca cca act tca act tgg gct gtg aat aca     281
Ser Ile Trp Leu Ile Leu Ala Pro Thr Ser Thr Trp Ala Val Asn Thr
 10              15                  20                  25 atc atc tac aat gtt gga agt acc acc att agc aaa tac gcc act ttt     329
Ile Ile Tyr Asn Val Gly Ser Thr Thr Ile Ser Lys Tyr Ala Thr Phe
             30                  35                  40 ctg aat gat ctt cgt aat gaa gcg aaa gat cca agt tta aaa tgc tat     377
Leu Asn Asp Leu Arg Asn Glu Ala Lys Asp Pro Ser Leu Lys Cys Tyr
         45                  50                  55 gga ata cca atg ctg ccc aat aca aat aca aat cca aag tac gtg ttg     425
Gly Ile Pro Met Leu Pro Asn Thr Asn Thr Asn Pro Lys Tyr Val Leu
     60                  65                  70 gtt gag ctc caa ggt tca aat aaa aaa acc atc aca cta atg ctg aga     473
Val Glu Leu Gln Gly Ser Asn Lys Lys Thr Ile Thr Leu Met Leu Arg
 75                  80                  85 cga aac aat ttg tat gtg atg ggt tat tct gat ccc ttt gaa acc aat     521
Arg Asn Asn Leu Tyr Val Met Gly Tyr Ser Asp Pro Phe Glu Thr Asn
 90                  95                 100                 105 aaa tgt cgt tac cat atc ttt aat gat atc tca ggt act gaa cgc caa     569
Lys Cys Arg Tyr His Ile Phe Asn Asp Ile Ser Gly Thr Glu Arg Gln
            110                 115                 120
```

```
gat gta gag act act ctt tgc cca aat gcc aat tct cgt gtt agt aaa      617
Asp Val Glu Thr Thr Leu Cys Pro Asn Ala Asn Ser Arg Val Ser Lys
            125                 130                 135 aac ata aac ttt gat agt cga tat cca aca ttg gaa tca aaa gcg gga      665
Asn Ile Asn Phe Asp Ser Arg Tyr Pro Thr Leu Glu Ser Lys Ala Gly
            140                 145                 150 gta aaa tca aga agt cag gtc caa ctg gga att caa ata ctc gac agt      713
Val Lys Ser Arg Ser Gln Val Gln Leu Gly Ile Gln Ile Leu Asp Ser
            155                 160                 165 aat att gga aag att tct gga gtg atg tca ttc act gag aaa acc gaa      761
Asn Ile Gly Lys Ile Ser Gly Val Met Ser Phe Thr Glu Lys Thr Glu
170                 175                 180                 185 gcc gaa ttc cta ttg gta gcc ata caa atg gta tca gag gca gca aga      809
Ala Glu Phe Leu Leu Val Ala Ile Gln Met Val Ser Glu Ala Ala Arg
            190                 195                 200 ttc aag tac ata gag aat cag gtg aaa act aat ttt aac aga gca ttc      857
Phe Lys Tyr Ile Glu Asn Gln Val Lys Thr Asn Phe Asn Arg Ala Phe
            205                 210                 215 aac cct aat ccc aaa gta ctt aat ttg caa gag aca tgg ggt aag att      905
Asn Pro Asn Pro Lys Val Leu Asn Leu Gln Glu Thr Trp Gly Lys Ile
            220                 225                 230 tca aca gca att cat gat gcc aag aat gga gtt tta ccc aaa cct ctc      953
Ser Thr Ala Ile His Asp Ala Lys Asn Gly Val Leu Pro Lys Pro Leu
235                 240                 245 gag cta gtg gat gcc agt ggt gcc aag tgg ata gtg ttg aga gtg gat     1001
Glu Leu Val Asp Ala Ser Gly Ala Lys Trp Ile Val Leu Arg Val Asp
250                 255                 260                 265 gaa atc aag cct gat gta gca ctc tta aac tac gtt ggt ggg agc tgt     1049
Glu Ile Lys Pro Asp Val Ala Leu Leu Asn Tyr Val Gly Gly Ser Cys
            270                 275                 280 cag aca act tat aac caa aat gcc atg ttt cct caa ctt ata atg tct     1097
Gln Thr Thr Tyr Asn Gln Asn Ala Met Phe Pro Gln Leu Ile Met Ser
            285                 290                 295 act tat tat aat tac atg gtt aat ctt ggt gat cta ttt gaa gga ttc     1145
Thr Tyr Tyr Asn Tyr Met Val Asn Leu Gly Asp Leu Phe Glu Gly Phe
300                 305                 310 tgatcataaa cataataagg agtatatata tattactcca actatattat aaagcttaaa   1205
taagaggccg tgttaattag tacttgttgc cttttgcttt atggtgttgt ttattatgcc   1265
ttgtatgctt gtaatattat ctagagaaca agatgtactg tgtaatagtc ttgtttgaaa   1325
taaaacttcc aattatgatg caaaaaaaaa aaaaa                              1360
```

<210> SEQ ID NO 20
<211> LENGTH: 313
<212> TYPE: PRT
<213> ORGANISM: Phytolacca americana

<400> SEQUENCE: 20

```
Met Lys Ser Met Leu Val Val Thr Ile Ser Ile Trp Leu Ile Leu Ala
1               5                   10                  15

Pro Thr Ser Thr Trp Ala Val Asn Thr Ile Ile Tyr Asn Val Gly Ser
                20                  25                  30

Thr Thr Ile Ser Lys Tyr Ala Thr Phe Leu Asn Asp Leu Arg Asn Glu
            35                  40                  45

Ala Lys Asp Pro Ser Leu Lys Cys Tyr Gly Ile Pro Met Leu Pro Asn
        50                  55                  60

Thr Asn Thr Asn Pro Lys Tyr Val Leu Val Glu Leu Gln Gly Ser Asn
65                  70                  75                  80

Lys Lys Thr Ile Thr Leu Met Leu Arg Arg Asn Asn Leu Tyr Val Met
```

```
                    85                  90                  95
Gly Tyr Ser Asp Pro Phe Glu Thr Asn Lys Cys Arg Tyr His Ile Phe
                100                 105                 110

Asn Asp Ile Ser Gly Thr Glu Arg Gln Asp Val Glu Thr Thr Leu Cys
            115                 120                 125

Pro Asn Ala Asn Ser Arg Val Ser Lys Asn Ile Asn Phe Asp Ser Arg
        130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
            180                 185                 190

Ile Gln Met Val Ser Glu Ala Ala Arg Phe Lys Tyr Ile Glu Asn Gln
        195                 200                 205

Val Lys Thr Asn Phe Asn Arg Ala Phe Asn Pro Asn Pro Lys Val Leu
    210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
            260                 265                 270

Leu Leu Asn Tyr Val Gly Gly Ser Cys Gln Thr Thr Tyr Asn Gln Asn
        275                 280                 285

Ala Met Phe Pro Gln Leu Ile Met Ser Thr Tyr Tyr Asn Tyr Met Val
    290                 295                 300

Asn Leu Gly Asp Leu Phe Glu Gly Phe
305                 310

<210> SEQ ID NO 21
<211> LENGTH: 934
<212> TYPE: DNA
<213> ORGANISM: Phytolacca americana
<220> FEATURE:
<221> NAME/KEY: CDS
<222> LOCATION: (1)..(930)

<400> SEQUENCE: 21 atg aag atg aag gtg tta gaa gta gtt ggg ttg gca ata tcg ata tgg      48
Met Lys Met Lys Val Leu Glu Val Val Gly Leu Ala Ile Ser Ile Trp
  1               5                  10                  15 ctg atg ctt aca cca cca gct tct tca aac ata gtg ttt gac gtt gag      96
Leu Met Leu Thr Pro Pro Ala Ser Ser Asn Ile Val Phe Asp Val Glu
                 20                  25                  30 aat gcc aca cca gaa acc tac tct aat ttt ctg act agt ttg cga gaa     144
Asn Ala Thr Pro Glu Thr Tyr Ser Asn Phe Leu Thr Ser Leu Arg Glu
             35                  40                  45 gct gtg aaa gac aag aaa ttg aca tgc cat gga atg ata atg gcc aca     192
Ala Val Lys Asp Lys Lys Leu Thr Cys His Gly Met Ile Met Ala Thr
         50                  55                  60 acc ctc act gaa caa ccc aag tat gtg ttg gtt gac ctc aaa ttc gga     240
Thr Leu Thr Glu Gln Pro Lys Tyr Val Leu Val Asp Leu Lys Phe Gly
 65                  70                  75                  80 tct gga aca ttc aca tta gca atc aga agg gga aac tta tat ttg gag     288
Ser Gly Thr Phe Thr Leu Ala Ile Arg Arg Gly Asn Leu Tyr Leu Glu
                 85                  90                  95 ggc tat tct gac att tac aat gga aaa tgt cgt tat cgg atc ttc aag     336
```

```
Gly Tyr Ser Asp Ile Tyr Asn Gly Lys Cys Arg Tyr Arg Ile Phe Lys
                100                 105                 110 gat tca gaa tcc gat gcc caa gag acc gtt tgc ccc ggg gac aaa agc        384
Asp Ser Glu Ser Asp Ala Gln Glu Thr Val Cys Pro Gly Asp Lys Ser
            115                 120                 125 aag cct ggc act cag aat aat atc ccc tat gaa aag agt tac aaa ggg        432
Lys Pro Gly Thr Gln Asn Asn Ile Pro Tyr Glu Lys Ser Tyr Lys Gly
        130                 135                 140 atg gaa tca aag ggt ggg gct aga act aaa tta ggg tta gga aag ata        480
Met Glu Ser Lys Gly Gly Ala Arg Thr Lys Leu Gly Leu Gly Lys Ile
145                 150                 155                 160 aca ctc aag agt cga atg ggt aaa atc tac ggc aag gat gca acg gat        528
Thr Leu Lys Ser Arg Met Gly Lys Ile Tyr Gly Lys Asp Ala Thr Asp
                165                 170                 175 cag aag cag tat caa aaa aat gag gct gaa ttt ctt ctt ata gcc gtt        576
Gln Lys Gln Tyr Gln Lys Asn Glu Ala Glu Phe Leu Leu Ile Ala Val
            180                 185                 190 caa atg gtt act gag gca tca agg ttc aaa tac att gag aac aaa gtg        624
Gln Met Val Thr Glu Ala Ser Arg Phe Lys Tyr Ile Glu Asn Lys Val
        195                 200                 205 aag gct aaa ttt gat gat gcc aat ggg tat cag cca gat cct aaa gct        672
Lys Ala Lys Phe Asp Asp Ala Asn Gly Tyr Gln Pro Asp Pro Lys Ala
210                 215                 220 att tcc cta gag aaa aat tgg gac agt gtt tct aag gtc att gca aaa        720
Ile Ser Leu Glu Lys Asn Trp Asp Ser Val Ser Lys Val Ile Ala Lys
                225                 230                 235                 240 gtt ggc acc tcc ggt gat agt act gtt act tta cct gga gac cta aaa        768
Val Gly Thr Ser Gly Asp Ser Thr Val Thr Leu Pro Gly Asp Leu Lys
            245                 250                 255 gat gag aat aat aaa cct tgg act acg gcc acc atg aac gac ctt aag        816
Asp Glu Asn Asn Lys Pro Trp Thr Thr Ala Thr Met Asn Asp Leu Lys
        260                 265                 270 aac gac att atg gca ctc cta acc cac gtt act tgc aag gtt aaa agt        864
Asn Asp Ile Met Ala Leu Leu Thr His Val Thr Cys Lys Val Lys Ser
275                 280                 285 tcc atg ttc cct gaa att atg tcc tat tat tat agg act agt att agt        912
Ser Met Phe Pro Glu Ile Met Ser Tyr Tyr Tyr Arg Thr Ser Ile Ser
                290                 295                 300 aac ctt ggt gaa ttc gag tgat                                            934
Asn Leu Gly Glu Phe Glu
305                 310

<210> SEQ ID NO 22
<211> LENGTH: 310
<212> TYPE: PRT
<213> ORGANISM: Phytolacca americana

<400> SEQUENCE: 22

Met Lys Met Lys Val Leu Glu Val Val Gly Leu Ala Ile Ser Ile Trp
1               5                   10                  15

Leu Met Leu Thr Pro Pro Ala Ser Ser Asn Ile Val Phe Asp Val Glu
            20                  25                  30

Asn Ala Thr Pro Glu Thr Tyr Ser Asn Phe Leu Thr Ser Leu Arg Glu
        35                  40                  45

Ala Val Lys Asp Lys Lys Leu Thr Cys His Gly Met Ile Met Ala Thr
    50                  55                  60

Thr Leu Thr Glu Gln Pro Lys Tyr Val Leu Val Asp Leu Lys Phe Gly
65                  70                  75                  80

Ser Gly Thr Phe Thr Leu Ala Ile Arg Arg Gly Asn Leu Tyr Leu Glu
                85                  90                  95
```

```
Gly Tyr Ser Asp Ile Tyr Asn Gly Lys Cys Arg Tyr Arg Ile Phe Lys
            100                 105                 110
Asp Ser Glu Ser Asp Ala Gln Glu Thr Val Cys Pro Gly Asp Lys Ser
        115                 120                 125
Lys Pro Gly Thr Gln Asn Asn Ile Pro Tyr Glu Lys Ser Tyr Lys Gly
    130                 135                 140
Met Glu Ser Lys Gly Gly Ala Arg Thr Lys Leu Gly Leu Gly Lys Ile
145                 150                 155                 160
Thr Leu Lys Ser Arg Met Gly Lys Ile Tyr Gly Lys Asp Ala Thr Asp
                165                 170                 175
Gln Lys Gln Tyr Gln Lys Asn Glu Ala Glu Phe Leu Leu Ile Ala Val
            180                 185                 190
Gln Met Val Thr Glu Ala Ser Arg Phe Lys Tyr Ile Glu Asn Lys Val
        195                 200                 205
Lys Ala Lys Phe Asp Asp Ala Asn Gly Tyr Gln Pro Asp Pro Lys Ala
    210                 215                 220
Ile Ser Leu Glu Lys Asn Trp Asp Ser Val Ser Lys Val Ile Ala Lys
225                 230                 235                 240
Val Gly Thr Ser Gly Asp Ser Thr Val Thr Leu Pro Gly Asp Leu Lys
                245                 250                 255
Asp Glu Asn Asn Lys Pro Trp Thr Thr Ala Thr Met Asn Asp Leu Lys
            260                 265                 270
Asn Asp Ile Met Ala Leu Leu Thr His Val Thr Cys Lys Val Lys Ser
        275                 280                 285
Ser Met Phe Pro Glu Ile Met Ser Tyr Tyr Tyr Arg Thr Ser Ile Ser
    290                 295                 300
Asn Leu Gly Glu Phe Glu
305                 310

<210> SEQ ID NO 23
<211> LENGTH: 807
<212> TYPE: DNA
<213> ORGANISM: Ricinus communis
<220> FEATURE:
<221> NAME/KEY: CDS
<222> LOCATION: (1)..(804)

<400> SEQUENCE: 23 atg ata ttc ccc aaa caa tac cca att ata aac ttt acc aca gcg ggt      48
Met Ile Phe Pro Lys Gln Tyr Pro Ile Ile Asn Phe Thr Thr Ala Gly
  1               5                  10                  15 gcc act gtg caa agc tac aca aac ttt atc aga gct gtt cgc ggt cgt      96
Ala Thr Val Gln Ser Tyr Thr Asn Phe Ile Arg Ala Val Arg Gly Arg
                 20                  25                  30 tta aca act gga gct gat gtg aga cat gaa ata cca gtg ttg cca aac     144
Leu Thr Thr Gly Ala Asp Val Arg His Glu Ile Pro Val Leu Pro Asn
             35                  40                  45 aga gtt ggt ttg cct ata aac caa cgg ttt att tta gtt gaa ctc tca     192
Arg Val Gly Leu Pro Ile Asn Gln Arg Phe Ile Leu Val Glu Leu Ser
         50                  55                  60 aat cat gca gag ctt tct gtt aca tta gcg ctg gat gtc acc aat gca     240
Asn His Ala Glu Leu Ser Val Thr Leu Ala Leu Asp Val Thr Asn Ala
 65                  70                  75                  80 tat gtg gta ggc tac cgt gct gga aat agc gca tat ttc ttt cat cct     288
Tyr Val Val Gly Tyr Arg Ala Gly Asn Ser Ala Tyr Phe Phe His Pro
                 85                  90                  95 gac aat cag gaa gat gca gaa gca atc act cat ctt ttc act gat gtt     336
Asp Asn Gln Glu Asp Ala Glu Ala Ile Thr His Leu Phe Thr Asp Val
```

-continued

```
                    100                 105                 110
caa aat cga tat aca ttc gcc ttt ggt ggt aat tat gat aga ctt gaa      384
Gln Asn Arg Tyr Thr Phe Ala Phe Gly Gly Asn Tyr Asp Arg Leu Glu
            115                 120                 125 caa ctt gct ggt aat ctg aga gaa aat atc gag ttg gga aat ggt cca      432
Gln Leu Ala Gly Asn Leu Arg Glu Asn Ile Glu Leu Gly Asn Gly Pro
        130                 135                 140 cta gag gag gct atc tca gcg ctt tat tat tac agt act ggt ggc act      480
Leu Glu Glu Ala Ile Ser Ala Leu Tyr Tyr Tyr Ser Thr Gly Gly Thr
145                 150                 155                 160 cag ctt cca act ctg gct cgt tcc ttt ata att tgc atc caa atg att      528
Gln Leu Pro Thr Leu Ala Arg Ser Phe Ile Ile Cys Ile Gln Met Ile
                165                 170                 175 tca gaa gca gca aga ttc caa tat att gag gga gaa atg cgc acg aga      576
Ser Glu Ala Ala Arg Phe Gln Tyr Ile Glu Gly Glu Met Arg Thr Arg
            180                 185                 190 att agg tac aac cgg aga tct gca cca gat cct agc gta att aca ctt      624
Ile Arg Tyr Asn Arg Arg Ser Ala Pro Asp Pro Ser Val Ile Thr Leu
        195                 200                 205 gag aat agt tgg ggg aga ctt tcc act gca att caa gag tct aac caa      672
Glu Asn Ser Trp Gly Arg Leu Ser Thr Ala Ile Gln Glu Ser Asn Gln
210                 215                 220 gga gcc ttt gct agt cca att caa ctg caa aga cgt aat ggt tcc aaa      720
Gly Ala Phe Ala Ser Pro Ile Gln Leu Gln Arg Arg Asn Gly Ser Lys
225                 230                 235                 240 ttc agt gtg tac gat gtg agt ata tta atc cct atc ata gct ctc atg      768
Phe Ser Val Tyr Asp Val Ser Ile Leu Ile Pro Ile Ile Ala Leu Met
                245                 250                 255 gtg tat aga tgc gca cct cca cca tcg tca cag ttt taa                  807
Val Tyr Arg Cys Ala Pro Pro Pro Ser Ser Gln Phe
            260                 265

<210> SEQ ID NO 24
<211> LENGTH: 268
<212> TYPE: PRT
<213> ORGANISM: Ricinus communis

<400> SEQUENCE: 24

Met Ile Phe Pro Lys Gln Tyr Pro Ile Ile Asn Phe Thr Thr Ala Gly
1               5                   10                  15

Ala Thr Val Gln Ser Tyr Thr Asn Phe Ile Arg Ala Val Arg Gly Arg
            20                  25                  30

Leu Thr Thr Gly Ala Asp Val Arg His Gl

-continued

```
Gln Leu Pro Thr Leu Ala Arg Ser Phe Ile Ile Cys Ile Gln Met Ile
                165                 170                 175
Ser Glu Ala Ala Arg Phe Gln Tyr Ile Glu Gly Glu Met Arg Thr Arg
            180                 185                 190
Ile Arg Tyr Asn Arg Arg Ser Ala Pro Asp Pro Ser Val Ile Thr Leu
        195                 200                 205
Glu Asn Ser Trp Gly Arg Leu Ser Thr Ala Ile Gln Glu Ser Asn Gln
    210                 215                 220
Gly Ala Phe Ala Ser Pro Ile Gln Leu Gln Arg Arg Asn Gly Ser Lys
225                 230                 235                 240
Phe Ser Val Tyr Asp Val Ser Ile Leu Ile Pro Ile Ile Ala Leu Met
                245                 250                 255
Val Tyr Arg Cys Ala Pro Pro Ser Ser Gln Phe
            260                 265

<210> SEQ ID NO 25
<211> LENGTH: 960
<212> TYPE: DNA
<213> ORGANISM: Bacteriophage SC370
<220> FEATURE:
<221> NAME/KEY: CDS
<222> LOCATION: (1)..(957)

<400> SEQUENCE: 25 atg aag tgt ata tta ttt aaa tgg gta ctg tgc ctg tta ctg ggt ttt     48
Met Lys Cys Ile Leu Phe Lys Trp Val Leu Cys Leu Leu Leu Gly Phe
  1               5                  10                  15 tct tcg gta tcc tat tcc cgg gag ttt acg ata gac ttt tcg acc caa     96
Ser Ser Val Ser Tyr Ser Arg Glu Phe Thr Ile Asp Phe Ser Thr Gln
             20                  25                  30 caa agt tat gtc tct tcg tta aat agt ata cgg aca gag ata tcg acc    144
Gln Ser Tyr Val Ser Ser Leu Asn Ser Ile Arg Thr Glu Ile Ser Thr
         35                  40                  45 cct ctt gaa cat ata tct cag ggg acc aca tcg gtg tct gtt att aac    192
Pro Leu Glu His Ile Ser Gln Gly Thr Thr Ser Val Ser Val Ile Asn
     50                  55                  60 cac acc cca ccg ggc agt tat ttt gct gtg gat ata cga ggg ctt gat    240
His Thr Pro Pro Gly Ser Tyr Phe Ala Val Asp Ile Arg Gly Leu Asp
 65                  70                  75                  80 gtc tat cag gcg cgt ttt gac cat ctt cgt ctg att att gag caa aat    288
Val Tyr Gln Ala Arg Phe Asp His Leu Arg Leu Ile Ile Glu Gln Asn
                 85                  90                  95 aat tta tat gtg gcc ggg ttc gtt aat acg gca aca aat act ttc tac    336
Asn Leu Tyr Val Ala Gly Phe Val Asn Thr Ala Thr Asn Thr Phe Tyr
            100                 105                 110 cgt ttt tca gat ttt aca cat ata tca gtg ccc ggt gtg aca acg gtt    384
Arg Phe Ser Asp Phe Thr His Ile Ser Val Pro Gly Val Thr Thr Val
        115                 120                 125 tcc atg aca acg gac agc agt tat acc act ctg caa cgt gtc gca gcg    432
Ser Met Thr Thr Asp Ser Ser Tyr Thr Thr Leu Gln Arg Val Ala Ala
    130                 135                 140 ctg gaa cgt tcc gga atg caa atc agt cgt cac tca ctg gtt tca tca    480
Leu Glu Arg Ser Gly Met Gln Ile Ser Arg His Ser Leu Val Ser Ser
145                 150                 155                 160 tat ctg gcg tta atg gag ttc agt ggt aat aca atg acc aga gat gca    528
Tyr Leu Ala Leu Met Glu Phe Ser Gly Asn Thr Met Thr Arg Asp Ala
                165                 170                 175 tcc aga gca gtt ctg cgt ttt gtc act gtc aca gca gaa gcc tta cgc    576
Ser Arg Ala Val Leu Arg Phe Val Thr Val Thr Ala Glu Ala Leu Arg
            180                 185                 190
```

```
ttc agg cag ata cag aga gaa ttt cgt cag gca ctg tct gaa act gct      624
Phe Arg Gln Ile Gln Arg Glu Phe Arg Gln Ala Leu Ser Glu Thr Ala
        195                 200                 205 cct gtg tat acg atg acg ccg gga gac gtg gac ctc act ctg aac tgg      672
Pro Val Tyr Thr Met Thr Pro Gly Asp Val Asp Leu Thr Leu Asn Trp
210                 215                 220 ggg cga atc agc aat gtg ctt ccg gag tat cgg gga gag gat ggt gtc      720
Gly Arg Ile Ser Asn Val Leu Pro Glu Tyr Arg Gly Glu Asp Gly Val
225                 230                 235                 240 aga gtg ggg aga ata tcc ttt aat aat ata tca gcg ata ctg ggg act      768
Arg Val Gly Arg Ile Ser Phe Asn Asn Ile Ser Ala Ile Leu Gly Thr
            245                 250                 255 gtg gcc gtt ata ctg aat tgc cat cat cag ggg gcg cgt tct gtt cgc      816
Val Ala Val Ile Leu Asn Cys His His Gln Gly Ala Arg Ser Val Arg
        260                 265                 270 gcc gtg aat gaa gag agt caa cca gaa tgt cag ata act ggc gac agg      864
Ala Val Asn Glu Glu Ser Gln Pro Glu Cys Gln Ile Thr Gly Asp Arg
    275                 280                 285 cct gtt ata aaa ata aac aat aca tta tgg gaa agt aat aca gct gca      912
Pro Val Ile Lys Ile Asn Asn Thr Leu Trp Glu Ser Asn Thr Ala Ala
290                 295                 300 gcg ttt ctg aac aga aag tca cag ttt tta tat aca acg ggt aaa taa      960
Ala Phe Leu Asn Arg Lys Ser Gln Phe Leu Tyr Thr Thr Gly Lys
305                 310                 315
```

<210> SEQ ID NO 26
<211> LENGTH: 319
<212> TYPE: PRT
<213> ORGANISM: Bacteriophage SC370

<400> SEQUENCE: 26

```
Met Lys Cys Ile Leu Phe Lys Trp Val Leu Cys Leu Leu Leu Gly Phe
1               5                   10                  15

Ser Ser Val Ser Tyr Ser Arg Glu Phe Thr Ile Asp Phe Ser Thr Gln
            20                  25                  30

Gln Ser Tyr Val Ser Ser Leu Asn Ser Ile Arg Thr Glu Ile Ser Thr
        35                  40                  45

Pro Leu Glu His Ile Ser Gln Gly Thr Thr Ser Val Ser Val Ile Asn
    50                  55                  60

His Thr Pro Pro Gly Ser Tyr Phe Ala Val Asp Ile Arg Gly Leu Asp
65                  70                  75                  80

Val Tyr Gln Ala Arg Phe Asp His Leu Arg Leu Ile Ile Glu Gln Asn
                85                  90                  95

Asn Leu Tyr Val Ala Gly Phe Val Asn Thr Ala Thr Asn Thr Phe Tyr
            100                 105                 110

Arg Phe Ser Asp Phe Thr His Ile Ser Val Pro Gly Val Thr Thr Val
        115                 120                 125

Ser Met Thr Thr Asp Ser Ser Tyr Thr Thr Leu Gln Arg Val Ala Ala
    130                 135                 140

Leu Glu Arg Ser Gly Met Gln Ile Ser Arg His Ser Leu Val Ser Ser
145                 150                 155                 160

Tyr Leu Ala Leu Met Glu Phe Ser Gly Asn Thr Met Thr Arg Asp Ala
                165                 170                 175

Ser Arg Ala Val Leu Arg Phe Val Thr Val Thr Ala Glu Ala Leu Arg
            180                 185                 190

Phe Arg Gln Ile Gln Arg Glu Phe Arg Gln Ala Leu Ser Glu Thr Ala
        195                 200                 205

Pro Val Tyr Thr Met Thr Pro Gly Asp Val Asp Leu Thr Leu Asn Trp
```

```
                  210                 215                 220
Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
                260                 265                 270

Ala Val Asn Glu Glu Ser Gln Pro Glu Cys Gln Ile Thr Gly Asp Arg
                275                 280                 285

Pro Val Ile Lys Ile Asn Asn Thr Leu Trp Glu Ser Asn Thr Ala Ala
                290                 295                 300

Ala Phe Leu Asn Arg Lys Ser Gln Phe Leu Tyr Thr Thr Gly Lys
305                 310                 315

<210> SEQ ID NO 27
<211> LENGTH: 948
<212> TYPE: DNA
<213> ORGANISM: Bacteriophage SC370
<220> FEATURE:
<221> NAME/KEY: CDS
<222> LOCATION: (1)..(945)

<400> SEQUENCE: 27 atg aaa ata att att ttt aga gtg cta act ttt ttc ttt gtt atc ttt        48
Met Lys Ile Ile Ile Phe Arg Val Leu Thr Phe Phe Phe Val Ile Phe
1               5                   10                  15 tca gtt aat gtg gtt gcg aag gaa ttt acc tta gac ttc tcg act gca        96
Ser Val Asn Val Val Ala Lys Glu Phe Thr Leu Asp Phe Ser Thr Ala
                20                  25                  30 aag acg tat gta gat tcg ctg aat gtc att cgc tct gca ata ggt act       144
Lys Thr Tyr Val Asp Ser Leu Asn Val Ile Arg Ser Ala Ile Gly Thr
            35                  40                  45 cca tta cag act att tca tca gga ggt acg tct tta ctg atg att gat       192
Pro Leu Gln Thr Ile Ser Ser Gly Gly Thr Ser Leu Leu Met Ile Asp
    50                  55                  60 agt ggc aca ggg gat aat ttg ttt gca gtt gat gtc aga ggg ata gat       240
Ser Gly Thr Gly Asp Asn Leu Phe Ala Val Asp Val Arg Gly Ile Asp
65                  70                  75                  80 cca gag gaa ggg cgg ttt aat aat cta cgg ctt att gtt gaa cga aat       288
Pro Glu Glu Gly Arg Phe Asn Asn Leu Arg Leu Ile Val Glu Arg Asn
                85                  90                  95 aat tta tat gtg aca gga ttt gtt aac agg aca aat aat gtt ttt tat       336
Asn Leu Tyr Val Thr Gly Phe Val Asn Arg Thr Asn Asn Val Phe Tyr
            100                 105                 110 cgc ttt gct gat ttt tca cat gtt acc ttt cca ggt aca aca gcg gtt       384
Arg Phe Ala Asp Phe Ser His Val Thr Phe Pro Gly Thr Thr Ala Val
    115                 120                 125 aca ttg tct ggt gac agt agc tat acc acg tta cag cgt gtt gca ggg       432
Thr Leu Ser Gly Asp Ser Ser Tyr Thr Thr Leu Gln Arg Val Ala Gly
130                 135                 140 atc agt cgt acg ggg atg cag ata aat cgc cat tcg ttg act act tct       480
Ile Ser Arg Thr Gly Met Gln Ile Asn Arg His Ser Leu Thr Thr Ser
145                 150                 155                 160 tat ctg gat tta atg tcg cat agt gga acc tca ctg acg cag tct gtg       528
Tyr Leu Asp Leu Met Ser His Ser Gly Thr Ser Leu Thr Gln Ser Val
                165                 170                 175 gca aga gcg atg tta cgg ttt gtt act gtg aca gct gaa gct tta cgt       576
Ala Arg Ala Met Leu Arg Phe Val Thr Val Thr Ala Glu Ala Leu Arg
            180                 185                 190 ttt cgg caa ata cag agg gga ttt cgt aca aca ctg gat gat ctc agt       624
Phe Arg Gln Ile Gln Arg Gly Phe Arg Thr Thr Leu Asp Asp Leu Ser
```

```
Phe Arg Gln Ile Gln Arg Gly Phe Arg Thr Thr Leu Asp Asp Leu Ser
        195                 200                 205 ggg cgt tct tat gta atg act gct gaa gat gtt gat ctt aca ttg aac    672
Gly Arg Ser Tyr Val Met Thr Ala Glu Asp Val Asp Leu Thr Leu Asn
210                 215                 220 tgg gga agg ttg agt agt gtc ctg cct gat tat cat gga caa gac tct    720
Trp Gly Arg Leu Ser Ser Val Leu Pro Asp Tyr His Gly Gln Asp Ser
225                 230                 235                 240 gtt cgt gta gga aga att tct ttt gga agc att aat gca att ctg gga    768
Val Arg Val Gly Arg Ile Ser Phe Gly Ser Ile Asn Ala Ile Leu Gly
                245                 250                 255 agc gtg gca tta ata ctg aat tgt cat cat cat gca tcg cga gtt gcc    816
Ser Val Ala Leu Ile Leu Asn Cys His His His Ala Ser Arg Val Ala
        260                 265                 270 aga atg gca tct gat gag ttt cct tct atg tgt ccg gca gat gga aga    864
Arg Met Ala Ser Asp Glu Phe Pro Ser Met Cys Pro Ala Asp Gly Arg
    275                 280                 285 gtc cgt ggg att acg cac aat aaa ata ttg tgg gat tca tcc act ctg    912
Val Arg Gly Ile Thr His Asn Lys Ile Leu Trp Asp Ser Ser Thr Leu
290                 295                 300 ggg gca att ctg atg cgc aga act att agc agt tga                    948
Gly Ala Ile Leu Met Arg Arg Thr Ile Ser Ser
305                 310                 315

<210> SEQ ID NO 28
<211> LENGTH: 315
<212> TYPE: PRT
<213> ORGANISM: Bacteriophage SC370

<400> SEQUENCE: 28

Met Lys Ile Ile Ile Phe Arg Val Leu Thr Phe Phe Val Ile Phe
 1               5                  10                  15

Ser Val Asn Val Val Ala Lys Glu Phe Thr Leu Asp Phe Ser Thr Ala
                20                  25                  30

Lys Thr Tyr Val Asp Ser Leu Asn Val Ile Arg Ser Ala Ile Gly Thr
            35                  40                  45

Pro Leu Gln Thr Ile Ser Ser Gly Gly Thr Ser Leu Leu Met Ile Asp
        50                  55                  60

Ser Gly Thr Gly Asp Asn Leu Phe Ala Val Asp Val Arg Gly Ile Asp
65                  70                  75                  80

Pro Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
                100                 105                 110

Arg Phe Ala Asp Phe Ser His Val Thr Phe Pro Gly Thr Thr Ala Val
            115                 120                 125

Thr Leu Ser Gly Asp Ser Ser Tyr Thr Thr Leu Gln Arg Val Ala Gly
        130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220
```

```
Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
                245                 250                 255

Ser Val Ala Leu Ile Leu Asn Cys His His Ala Ser Arg Val Ala
            260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315

<210> SEQ ID NO 29
<211> LENGTH: 66
<212> TYPE: DNA
<213> ORGANISM: Saccharomyces cerevisiae

<400> SEQUENCE: 29
atgtctcaca gaaagtacga agcaccacgt cacggtcatt taggtttctt gccaagaaag      60
agagct                                                                66

<210> SEQ ID NO 30
<211> LENGTH: 99
<212> TYPE: PRT
<213> ORGANISM: Saccharomyces cerevisiae

<400> SEQUENCE: 30

Met Ser His Arg Lys Tyr Glu Ala Pro Arg His Gly His Leu Gly Phe
1               5                   10                  15

Leu Pro Arg Lys Arg Ala Ala Ser Ile Arg Ala Arg Val Lys Ala Phe
            20                  25                  30

Pro Lys Asp Asp Arg Ser Lys Pro Val Ala Leu Thr Ser Phe Leu Gly
        35                  40                  45

Tyr Lys Ala Gly Met Thr Thr Ile Val Arg Asp Leu Asp Arg Pro Gly
    50                  55                  60

Ser Lys Phe His Lys Arg Glu Val Val Glu Ala Val Thr Val Val Asp
65                  70                  75                  80

Thr Pro Pro Val Val Val Gly Val Val Gly Tyr Val Glu Thr Pro
                85                  90                  95

Arg Gly Leu

<210> SEQ ID NO 31
<211> LENGTH: 298
<212> TYPE: DNA
<213> ORGANISM: Saccharomyces cerevisiae

<400> SEQUENCE: 31
atgtctcaca gaaagtacga agcaccacgt cacggtcatt taggtttctt gccaagaaag      60
agagctgcct ccatcagagc tagagttaag gcttttccaa aggatgacag atccaagcca     120
gttgctctaa cttccttctt gggttacaag gctggtatga ccaccattgt cagagatttg     180
gacagaccag ttctaagtt ccacaagcgt gaagttgtcg aagctgtcac cgttgttgac     240
actccaccag ttgtcgttgt tggtgttgtc ggttacgtcg aaacccccaag aggtttga     298

<210> SEQ ID NO 32
<211> LENGTH: 21
```

```
<212> TYPE: PRT
<213> ORGANISM: Saccharomyces cerevisiae

<400> SEQUENCE: 32

Met Ser His Arg Lys Tyr Glu Ala Pro Arg His Gly His Leu Gly Phe
 1               5                  10                  15

Leu Pro Arg Lys Arg
            20

<210> SEQ ID NO 33
<211> LENGTH: 22
<212> TYPE: PRT
<213> ORGANISM: Saccharomyces cerevisiae

<400> SEQUENCE: 33

Met Ser His Arg Lys Tyr Glu Ala Pro Arg His Gly His Leu Gly Phe
 1               5                  10                  15

Leu Pro Arg Lys Arg Ala
            20

<210> SEQ ID NO 34
<211> LENGTH: 23
<212> TYPE: PRT
<213> ORGANISM: Saccharomyces cerevisiae

<400> SEQUENCE: 34

Met Ser His Arg Lys Tyr Glu Ala Pro Arg His Gly His Leu Gly Phe
 1               5                  10                  15

Leu Pro Arg Lys Arg Ala Ala
            20

<210> SEQ ID NO 35
<211> LENGTH: 24
<212> TYPE: PRT
<213> ORGANISM: Saccharomyces cerevisiae

<400> SEQUENCE: 35

Met Ser His Arg Lys Tyr Glu Ala Pro Arg His Gly His Leu Gly Phe
 1               5                  10                  15

Leu Pro Arg Lys Arg Ala Ala Ser
            20

<210> SEQ ID NO 36
<211> LENGTH: 25
<212> TYPE: PRT
<213> ORGANISM: Saccharomyces cerevisiae

<400> SEQUENCE: 36

Met Ser His Arg Lys Tyr Glu Ala Pro Arg His Gly His Leu Gly Phe
 1               5                  10                  15

Leu Pro Arg Lys Arg Ala Ala Ser Ile
            20                  25

<210> SEQ ID NO 37
<211> LENGTH: 66
<212> TYPE: DNA
<213> ORGANISM: Saccharomyces cerevisiae

<400> SEQUENCE: 37
atgtctcaca gaaagtacga agcaccacgt cacggtcatt taggtttctt gccaagaaag    60
agataa                                                                66
```

-continued

```
<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aggcgttcag tcataatcc                                              19

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gggtaagatt tcaacagcaa ttca                                        24

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caccactggc atccactagc t                                           21

<210> SEQ ID NO 41
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
aguacgagag ga                                                     12

<210> SEQ ID NO 42
<211> LENGTH: 1140
<212> TYPE: DNA
<213> ORGANISM: Nicotiana tabacum
<220> FEATURE:
<221> NAME/KEY: CDS
<222> LOCATION: (1)..(1080)

<400> SEQUENCE: 42 atg tcg cat cgc aag ttt gag cac cca aga cac ggt tct ttg gga ttt    48
Met Ser His Arg Lys Phe Glu His Pro Arg His Gly Ser Leu Gly Phe
1               5                   10                  15 ctt cca agg aaa aga gca gca cga cac agg ggc aaa gtg aag gct ttt    96
Leu Pro Arg Lys Arg Ala Ala Arg His Arg Gly Lys Val Lys Ala Phe
            20                  25                  30 ccc aaa gat gat aca aca aaa cct tgc agg ttg aca gct ttc ctt ggc   144
Pro Lys Asp Asp Thr Thr Lys Pro Cys Arg Leu Thr Ala Phe Leu Gly
        35                  40                  45 tac aaa gct ggt atg act cat att gtc aga gat gtt gaa aaa cca ggg   192
Tyr Lys Ala Gly Met Thr His Ile Val Arg Asp Val Glu Lys Pro Gly
    50                  55                  60 tca aaa ctc cat aag aaa gaa aca tgc gaa ctg gtt acc ata att gaa   240
Ser Lys Leu His Lys Lys Glu Thr Cys Glu Leu Val Thr Ile Ile Glu
```

```
                    65                  70                  75                  80
acg cct cct atg att gtt gtt ggg gtt gtt ggc tat gtg aaa aca cca      288
Thr Pro Pro Met Ile Val Val Gly Val Val Gly Tyr Val Lys Thr Pro
                     85                  90                  95 cgt ggc ctt cgc tgc ctt agc acg gtc tgg gct caa cat ctt agt gaa      336
Arg Gly Leu Arg Cys Leu Ser Thr Val Trp Ala Gln His Leu Ser Glu
            100                 105                 110 gag att aaa agg aga ttc tac aag aac tgg tgc atg tcc aaa aag aag      384
Glu Ile Lys Arg Arg Phe Tyr Lys Asn Trp Cys Met Ser Lys Lys Lys
        115                 120                 125 gcc ttt gca aag tac tcg aag aag tat gaa act gat gat ggt aag aag      432
Ala Phe Ala Lys Tyr Ser Lys Lys Tyr Glu Thr Asp Asp Gly Lys Lys
    130                 135                 140 gat att aat gcg caa ttg gag aag atg aag aag tat tgt tgt gtc att      480
Asp Ile Asn Ala Gln Leu Glu Lys Met Lys Lys Tyr Cys Cys Val Ile
145                 150                 155                 160 cgt gtt ttg gcc cat act cag att aga aaa atg aaa ggt ctc aag caa      528
Arg Val Leu Ala His Thr Gln Ile Arg Lys Met Lys Gly Leu Lys Gln
                165                 170                 175 aag aag gca cat ctg atg gag att cag gtt aat ggt ggg gat gtt tcc      576
Lys Lys Ala His Leu Met Glu Ile Gln Val Asn Gly Gly Asp Val Ser
            180                 185                 190 cag aag gtt gat tat gct tat ggc ttc ttt gag aag cag att cct gtt      624
Gln Lys Val Asp Tyr Ala Tyr Gly Phe Phe Glu Lys Gln Ile Pro Val
        195                 200                 205 gat gct att ttc caa aag gat gag atg atc gat att att ggt gtg acc      672
Asp Ala Ile Phe Gln Lys Asp Glu Met Ile Asp Ile Ile Gly Val Thr
    210                 215                 220 aaa ggt aag ggt tat gag ggt gtg gtg act cgt tgg ggt gta acc cgt      720
Lys Gly Lys Gly Tyr Glu Gly Val Val Thr Arg Trp Gly Val Thr Arg
225                 230                 235                 240 ctc cca cgt aag acc cat cgt ggt ctt aga aag gtg gct tgt att ggt      768
Leu Pro Arg Lys Thr His Arg Gly Leu Arg Lys Val Ala Cys Ile Gly
                245                 250                 255 gct tgg cat cca gca cgg gtg tca tac act gta gct agg gct ggg cag      816
Ala Trp His Pro Ala Arg Val Ser Tyr Thr Val Ala Arg Ala Gly Gln
            260                 265                 270 aat ggt tat cac cat cgc act gag ctg aac aag aaa gtc tac agg ctg      864
Asn Gly Tyr His His Arg Thr Glu Leu Asn Lys Lys Val Tyr Arg Leu
        275                 280                 285 ggc aag gct ggt cag gag tct cat tct gca ata act gag ttt gac agg      912
Gly Lys Ala Gly Gln Glu Ser His Ser Ala Ile Thr Glu Phe Asp Arg
    290                 295                 300 act gag aag gat atc acg cca atg ggt gga ttt cct cat tat ggt att      960
Thr Glu Lys Asp Ile Thr Pro Met Gly Gly Phe Pro His Tyr Gly Ile
305                 310                 315                 320 gtg aaa gaa gac ttt ctg ttg att aag ggc tgc tgt gtt gga cca aag     1008
Val Lys Glu Asp Phe Leu Leu Ile Lys Gly Cys Cys Val Gly Pro Lys
                325                 330                 335 aag cgt gtt gtg act ctg agg cag tct ctg ttg aat cag aca tct agg     1056
Lys Arg Val Val Thr Leu Arg Gln Ser Leu Leu Asn Gln Thr Ser Arg
            340                 345                 350 gtt gca ttg gag gag atc aag ctc aagttcattg acacatcctc caagtttggc    1110
Val Ala Leu Glu Glu Ile Lys Leu
        355                 360 catggacgct tccagactac acaggagaag                                    1140

<210> SEQ ID NO 43
<211> LENGTH: 360
<212> TYPE: PRT
```

-continued

<213> ORGANISM: Nicotiana tabacum

<400> SEQUENCE: 43

```
Met Ser His Arg Lys Phe Glu His Pro Arg His Gly Ser Leu Gly Phe
 1               5                  10                  15
Leu Pro Arg Lys Arg Ala Ala Arg His Arg Gly Lys Val Lys Ala Phe
             20                  25                  30
Pro Lys Asp Asp Thr Thr Lys Pro Cys Arg Leu Thr Ala Phe Leu Gly
         35                  40                  45
Tyr Lys Ala Gly Met Thr His Ile Val Arg Asp Val Glu Lys Pro Gly
     50                  55                  60
Ser Lys Leu His Lys Lys Glu Thr Cys Glu Leu Val Thr Ile Ile Glu
 65                  70                  75                  80
Thr Pro Pro Met Ile Val Val Gly Val Val Gly Tyr Val Lys Thr Pro
                 85                  90                  95
Arg Gly Leu Arg Cys Leu Ser Thr Val Trp Ala Gln His Leu Ser Glu
            100                 105                 110
Glu Ile Lys Arg Arg Phe Tyr Lys Asn Trp Cys Met Ser Lys Lys Lys
        115                 120                 125
Ala Phe Ala Lys Tyr Ser Lys Lys Tyr Glu Thr Asp Asp Gly Lys Lys
    130                 135                 140
Asp Ile Asn Ala Gln Leu Glu Lys Met Lys Lys Tyr Cys Cys Val Ile
145                 150                 155                 160
Arg Val Leu Ala His Thr Gln Ile Arg Lys Met Lys Gly Leu Lys Gln
                165                 170                 175
Lys Lys Ala His Leu Met Glu Ile Gln Val Asn Gly Gly Asp Val Ser
            180                 185                 190
Gln Lys Val Asp Tyr Ala Tyr Gly Phe Phe Glu Lys Gln Ile Pro Val
        195                 200                 205
Asp Ala Ile Phe Gln Lys Asp Glu Met Ile Asp Ile Ile Gly Val Thr
    210                 215                 220
Lys Gly Lys Gly Tyr Glu Gly Val Val Thr Arg Trp Gly Val Thr Arg
225                 230                 235                 240
Leu Pro Arg Lys Thr His Arg Gly Leu Arg Lys Val Ala Cys Ile Gly
                245                 250                 255
Ala Trp His Pro Ala Arg Val Ser Tyr Thr Val Ala Arg Ala Gly Gln
            260                 265                 270
Asn Gly Tyr His His Arg Thr Glu Leu Asn Lys Lys Val Tyr Arg Leu
        275                 280                 285
Gly Lys Ala Gly Gln Glu Ser His Ser Ala Ile Thr Glu Phe Asp Arg
    290                 295                 300
Thr Glu Lys Asp Ile Thr Pro Met Gly Gly Phe Pro His Tyr Gly Ile
305                 310                 315                 320
Val Lys Glu Asp Phe Leu Leu Ile Lys Gly Cys Cys Val Gly Pro Lys
                325                 330                 335
Lys Arg Val Val Thr Leu Arg Gln Ser Leu Leu Asn Gln Thr Ser Arg
            340                 345                 350
Val Ala Leu Glu Glu Ile Lys Leu
        355                 360
```

<210> SEQ ID NO 44
<211> LENGTH: 1080
<212> TYPE: DNA
<213> ORGANISM: Nicotiana tabacum

<400> SEQUENCE: 44

-continued

```
gagcttgatc tcctccaatg caaccctaga tgtctgattc aacagagact gcctcagagt      60
cacaacacgc ttctttggtc caacacagca gcccttaatc aacagaaagt cttctttcac     120
aataccataa tgaggaaatc cacccattgg cgtgatatcc ttctcagtcc tgtcaaactc     180
agttattgca gaatgagact cctgaccagc cttgcccagc ctgtagactt tcttgttcag     240
ctcagtgcga tggtgataac cattctgccc agccctagct acagtgtatg acacccgtgc     300
tggatgccaa gcaccaatac aagccacctt tctaagacca cgatgggtct tacgtgggag     360
acgggttaca ccccaacgag tcaccacacc ctcataaccc ttacctttgg tcacaccaat     420
aatatcgatc atctcatcct tttggaaaat agcatcaaca ggaatctgct tctcaaagaa     480
gccataagca taatcaacct tctgggaaac atccccacca ttaacctgaa tctccatcag     540
atgtgccttc ttttgcttga gacctttcat ttttctaatc tgagtatggg ccaaaacacg     600
aatgacacaa caatacttct tcatcttctc caattgcgca ttaatatcct tcttaccatc     660
atcagtttca tacttcttcg agtactttgc aaaggccttc tttttggaca tgcaccagtt     720
cttgtagaat ctccttttaa tctcttcact aagatgttga gcccagaccg tgctaaggca     780
gcgaaggcca cgtggtgttt tcacatagcc aacaacccca acaacaatca taggaggcgt     840
ttcaattatg gtaaccagtt cgcatgtttc tttcttatgg agttttgacc ctggtttttc     900
aacatctctg acaatatgag tcataccagc tttgtagcca aggaaagctg tcaacctgca     960
aggttttgtt gtatcatctt tgggaaaagc cttcactttg ccctgtgtc gtgctgctct    1020 tttccttgga agaaatccca aagaaccgtg tcttgggtgc tcaaacttgc gatgcgacat    1080
```